US009132398B2

(12) United States Patent
Zhou et al.

(10) Patent No.: US 9,132,398 B2
(45) Date of Patent: Sep. 15, 2015

(54) INTEGRATED MICROFLUIDIC DEVICE AND METHODS

(75) Inventors: Peng Zhou, Newtown, PA (US); Lincoln C. Young, Ithaca, NY (US); Todd Roswech, Ithaca, NY (US); Gwendolyn Spizz, Ithaca, NY (US); Zongyuan Chen, Claymont, DE (US); Benjamin W. Thomas, Ithaca, NY (US); Travis Lee, Ithaca, NY (US)

(73) Assignee: RHEONIX, INC., Ithaca, NY (US)

( * ) Notice: Subject to any disclaimer, the term of this patent is extended or adjusted under 35 U.S.C. 154(b) by 1657 days.

(21) Appl. No.: 12/249,872

(22) Filed: Oct. 10, 2008

(65) Prior Publication Data

US 2012/0115738 A1 May 10, 2012

Related U.S. Application Data

(60) Provisional application No. 60/979,515, filed on Oct. 12, 2007.

(51) Int. Cl.
*C12M 1/34* (2006.01)
*C12M 3/00* (2006.01)
(Continued)

(52) U.S. Cl.
CPC ........... *B01F 13/0059* (2013.01); *B01F 5/0683* (2013.01); *B01F 5/0688* (2013.01);
(Continued)

(58) Field of Classification Search
CPC ............... B01L 7/52; B01L 2300/0636; B01J 2219/00659; B01J 2219/00722; C40B 40/06
USPC .................................. 435/6.12, 287.2; 506/9
See application file for complete search history.

(56) References Cited

U.S. PATENT DOCUMENTS 4,683,195 A 7/1987 Mullis et al.
4,683,202 A 7/1987 Mullis
(Continued)

FOREIGN PATENT DOCUMENTS

EP 1520621 A2 4/2005
WO WO-02068823 A1 9/2002
(Continued)

OTHER PUBLICATIONS

Patent Cooperation Treaty, International Preliminary Report on Patentability and Written Opinion of the International Searching Authority, dated Apr. 13, 2010, 7 pgs.
(Continued)

*Primary Examiner* — Michael Hobbs
(74) *Attorney, Agent, or Firm* — William Greener; Bond, Schoeneck & King, PLLC

(57) ABSTRACT

A microfluidic device for analyzing a sample of interest is provided. The microfluidic device can comprise a microfluidic device body, wherein the microfluidic device body comprises a sample preparation area, a nucleic acid amplification area, a nucleic acid analysis area, and a network of fluid channels. Each of the sample preparation area, the nucleic acid amplification area and the nucleic acid analysis area are fluidly interconnected to at least one of the other two areas by at least one of the fluid channels. Using the microfluidic device, sample preparation can be combined with amplification of a biologically active molecule, and a suitable biological sample can be provided for analysis and/or detection of a molecule of interest. The small-scale apparatus and methods provided are easier, faster, less expensive, and equally efficacious compared to larger scale equipment for the preparation and analysis of a biological sample.

36 Claims, 51 Drawing Sheets

(51) Int. Cl.

| | |
|---|---|
| ***B01F 13/00*** | (2006.01) |
| ***B01F 5/06*** | (2006.01) |
| ***B01F 11/00*** | (2006.01) |
| ***B01L 3/00*** | (2006.01) |
| *B01L 7/00* | (2006.01) |

(52) U.S. Cl.

CPC ......... *B01F11/0074* (2013.01); *B01L 3/50273* (2013.01); *B01L 7/52* (2013.01); *B01L 2200/027* (2013.01); *B01L 2200/0621* (2013.01); *B01L 2200/10* (2013.01); *B01L 2300/0816* (2013.01); *B01L 2300/185* (2013.01); *B01L 2300/1816* (2013.01); *B01L 2300/1822* (2013.01); *B01L 2300/1827* (2013.01); *B01L 2300/1844* (2013.01); *B01L 2400/0487* (2013.01); *B01L 2400/0638* (2013.01); *B01L 2400/084* (2013.01)

(56) References Cited

U.S. PATENT DOCUMENTS

| | | | | |
|---|---|---|---|---|
| 4,965,188 | A | 10/1990 | Mullis et al. | |
| 5,038,852 | A | 8/1991 | Johnson et al. | |
| 5,130,238 | A | 7/1992 | Malek et al. | |
| 5,234,809 | A | 8/1993 | Boom et al. | |
| 5,270,183 | A | 12/1993 | Corbett et al. | |
| 5,354,668 | A | 10/1994 | Auerbach | |
| 5,427,930 | A | 6/1995 | Birkenmeyer et al. | |
| 5,436,129 | A | 7/1995 | Stapleton | |
| 5,455,166 | A | 10/1995 | Walker | |
| 5,498,392 | A | 3/1996 | Wilding et al. | |
| 5,582,989 | A | 12/1996 | Caskey et al. | |
| 5,587,128 | A | 12/1996 | Wilding et al. | |
| 5,639,428 | A | 6/1997 | Cottingham | |
| 5,716,842 | A | 2/1998 | Baier et al. | |
| 5,716,852 | A | 2/1998 | Yager et al. | |
| 5,720,923 | A | 2/1998 | Haff et al. | |
| 5,724,404 | A | 3/1998 | Garcia et al. | |
| 5,726,026 | A | 3/1998 | Wilding et al. | |
| 5,726,751 | A | 3/1998 | Altendorf et al. | |
| 5,747,349 | A | 5/1998 | van den Engh et al. | |
| 5,748,827 | A | 5/1998 | Holl et al. | |
| 5,856,174 | A | 1/1999 | Lipshutz et al. | |
| 5,863,502 | A | 1/1999 | Southgate et al. | |
| 5,922,591 | A | 7/1999 | Anderson et al. | |
| 5,932,100 | A | 8/1999 | Yager et al. | |
| 5,935,522 | A | 8/1999 | Swerdlow et al. | |
| 5,948,684 | A | 9/1999 | Weigl et al. | |
| 5,955,029 | A | 9/1999 | Wilding et al. | |
| 5,965,410 | A | 10/1999 | Chow et al. | |
| 5,971,158 | A | 10/1999 | Yager et al. | |
| 5,972,710 | A | 10/1999 | Weigl et al. | |
| 5,974,867 | A | 11/1999 | Forster et al. | |
| 5,989,813 | A | 11/1999 | Gerdes | |
| 6,007,775 | A | 12/1999 | Yager | |
| 6,020,187 | A | 2/2000 | Tam | |
| 6,043,080 | A | 3/2000 | Lipshutz et al. | |
| 6,168,948 | B1 | 1/2001 | Anderson et al. | |
| 6,171,850 | B1 | 1/2001 | Nagle et al. | |
| 6,171,865 | B1 | 1/2001 | Weigl et al. | |
| 6,197,595 | B1 | 3/2001 | Anderson et al. | |
| 6,210,882 | B1 | 4/2001 | Landers et al. | |
| 6,326,211 | B1 | 12/2001 | Anderson et al. | |
| 6,335,166 | B1 | 1/2002 | Ammann et al. | |
| 6,387,290 | B1 | 5/2002 | Brody et al. | |
| 6,488,896 | B2 | 12/2002 | Weigl et al. | |
| 6,521,188 | B1 | 2/2003 | Webster | |
| 6,524,830 | B2 | 2/2003 | Kopf-Sill | |
| 6,541,274 | B2 | 4/2003 | Nagle et al. | |
| 6,576,459 | B2 | 6/2003 | Miles et al. | |
| 6,619,311 | B2 | 9/2003 | O'Connor et al. | |
| 6,680,193 | B1 | 1/2004 | Fouillet et al. | |
| 6,743,399 | B1 | 6/2004 | Weigl et al. | |
| 6,787,338 | B2 | 9/2004 | Wittwer et al. | |
| 6,830,936 | B2 | 12/2004 | Anderson et al. | |
| 6,953,675 | B2 | 10/2005 | Leung et al. | |
| 7,025,323 | B2 | 4/2006 | Krulevitch et al. | |
| 7,026,168 | B2 | 4/2006 | Bedingham et al. | |
| 7,087,414 | B2 | 8/2006 | Gerdes et al. | |
| 7,264,950 | B1 | 9/2007 | Lee et al. | |
| 7,297,313 | B1 | 11/2007 | Northrup et al. | |
| 2001/0046701 | A1 | 11/2001 | Schulte et al. | |
| 2002/0022261 | A1 | 2/2002 | Anderson et al. | |
| 2002/0098122 | A1 | 7/2002 | Singh et al. | |
| 2002/0155010 | A1 | 10/2002 | Karp et al. | |
| 2002/0195152 | A1 | 12/2002 | Fernandes et al. | |
| 2003/0008308 | A1 | 1/2003 | Enzelberger et al. | |
| 2003/0032172 | A1 | 2/2003 | Colston et al. | |
| 2003/0138359 | A1 | 7/2003 | Chow et al. | |
| 2003/0175990 | A1 | 9/2003 | Hayenga et al. | |
| 2003/0233827 | A1 | 12/2003 | Kuo et al. | |
| 2004/0081997 | A1 | 4/2004 | Stern | |
| 2004/0086872 | A1 | 5/2004 | Childers et al. | |
| 2004/0110132 | A1 | 6/2004 | Dong | |
| 2004/0132218 | A1 | 7/2004 | Ho | |
| 2004/0209354 | A1 | 10/2004 | Mathies et al. | |
| 2005/0013732 | A1 | 1/2005 | Battrell et al. | |
| 2005/0019792 | A1 | 1/2005 | McBride et al. | |
| 2005/0100946 | A1 | 5/2005 | Lipshutz et al. | |
| 2005/0129585 | A1 | 6/2005 | Kuo | |
| 2005/0202504 | A1 | 9/2005 | Anderson et al. | |
| 2005/0233440 | A1 | 10/2005 | Scurati et al. | |
| 2005/0250199 | A1 | 11/2005 | Anderson et al. | |
| 2006/0073484 | A1 | 4/2006 | Mathies et al. | |
| 2006/0184038 | A1* | 8/2006 | Smith et al. .................. | 600/476 |
| 2006/0246490 | A1 | 11/2006 | Anderson et al. | |
| 2007/0042427 | A1 | 2/2007 | Gerdes et al. | |
| 2007/0117201 | A1 | 5/2007 | Kweon et al. | |
| 2007/0166200 | A1* | 7/2007 | Zhou et al. .................... | 422/100 |
| 2007/0237686 | A1 | 10/2007 | Mathies et al. | |
| 2007/0248958 | A1 | 10/2007 | Jovanovich et al. | |
| 2008/0014576 | A1 | 1/2008 | Jovanovich et al. | |
| 2008/0264842 | A1 | 10/2008 | Hukari | |
| 2009/0325276 | A1* | 12/2009 | Battrell et al. ............. | 435/287.2 |
| 2010/0216657 | A1 | 8/2010 | Hukari | |

FOREIGN PATENT DOCUMENTS

| | | | |
|---|---|---|---|
| WO | 2007106579 | A2 | 9/2007 |
| WO | WO-2007/106579 | A2 | 9/2007 |
| WO | WO-2007106579 | A2 | 9/2007 |

OTHER PUBLICATIONS

Grover, William H. et al. Development and multiplexed control of latching pneumatic valves using microfluidic logical structures.Lab Chip, 2006, 6, 623-631.

Rolfe C. Anderson et al. 1997. Microfluidic Biochemical Analysis System. Transducers '97: 1997 International Conference on Solid-State Sensors and Actuators, Chicago, Jun. 16-19, 1997, 477-480.

Rolfe C. Anderson et al. 2000. A miniature integrated device for automated multistep genetic assays. Nucleic Acids Res. 28 (12): e60 (6 pp).

Paul Bayardelle et al. 2002. Development of oligonucleotide primers for the specific PCR-based detection of the most frequent Enterobacteriaceae species DNA using wec gene templates. Can. J. Microbiol. 48: 113-122.

Lin Chen et al. 2007. Total nucleic acid analysis integrated on microfluidic devices. Lab Chip 7: 1413-1423.

Christopher J. Easley et al. 2006. A fully integrated microfluidic genetic analysis system with sample-in-answer-out capability. Proc. Natl. Acad. Sciences USA 103 (51): 19272-19277.

William H. Grover, et al. 2003. Monolithic membrane valves and diaphragm pumps for practical large-scale integration into glass microfluidic devices. Sensors and Actuators B 89: 315-323.

E.T. Lagally et al. 2001. Single-Molecule DNA Amplification and Analysis in an Integrated Microfluidic Device, Analytical Chemistry 73 (3): 565-570.

Robin Hui Liu et al. 2004. Self-Contained, Fully Integrated Biochip for Sample Preparation, Polymerase Chain Reaction Amplification, and DNA Microarray Detection. Analytical Chemistry 76 (7): 1824-1831.

(56) References Cited

OTHER PUBLICATIONS

Kwang W. Oh et al. 2005. World-to-chip microfluidic interface with built-in valves for multichamber chip-based PCR assays. Lab Chip 5: 845-850.
Takahiro Ohori et al. 1998. Partly disposable three-way microvalve for a medical micro total analysis system, Sensors and Actuators A 64: 57-62.
Xing Yang et al. 1998. A MEMS thermopneumatic silicone rubber membrane. Sensors and Actuators A 64: 101-108.
Chunsun Zhang et al. 2007. Miniaturized PCR chips for nucleic acid amplification and analysis: latest advances and future trends. Nucleic Acids Research 35 (13): 4223-4237.
PCT/US2008/079659 International Search Report. Feb. 10, 2009. 5 pp.
International Searching Authority, European Patent Office, Notification of Transmittal of the International Search Report and the Written Opinion for corresponding PCT Patent Application No. PCT/US2008/079659, with International Search Report and Written Opinion dated Feb. 10, 2009 (14 pgs.).

* cited by examiner

On-Chip Probe Array

| | | | |
|---|---|---|---|
| 11 | 31 | 52 | 16 |
| 16 | 52 | 31 | 11 |
| 52 | 16 | 11 | 31 |
| 31 | 11 | 16 | 52 |

A. B.

INTEGRATED MICROFLUIDIC DEVICE AND METHODS

CROSS-REFERENCE TO RELATED APPLICATIONS

This application claims priority to and the benefit of U.S. provisional patent application Ser. No. 60/979,515, filed Oct. 12, 2007, which is incorporated herein by reference in its entirety.

STATEMENT REGARDING FEDERALLY SPONSORED RESEARCH OR DEVELOPMENT

Not applicable

REFERENCE TO APPENDIX

Not applicable.

1. TECHNICAL FIELD

The present invention relates to the field of microfluidics and the application of microfluidics in the fields of biochemistry and molecular biology. The invention further relates to integrated microfluidic platform apparatuses and associated methods. The invention also relates to microfluidic devices for preparing, amplifying and detecting biological molecules of interest, such as nucleic acids. The invention also relates to methods for preparing, amplifying and detecting biological molecules of interest, such as nucleic acids using microfluidic devices.

2. BACKGROUND OF THE INVENTION

Molecular biology can be broadly defined as the branch of biology that deals with the formation, structure and function of macromolecules such as nucleic acids and proteins and their role in cell replication and the transmission of genetic information, as well as the manipulation of nucleic acids, so that they can be sequenced, mutated, and further manipulated into the genome of an organism to study the biological effects of the mutation.

The conventional practice of biochemistry and molecular biology can require physical process resources on a scale that are frequently inversely proportional to the size of the subject being studied. For example, the apparatus and process chemistry associated with the preparation and purification of a biological sample such as a nucleic acid fragment for prospective analysis may easily require a full scale bio-laboratory with sterile facilities. Furthermore, an environmentally isolated facility of similar scale may typically be required to carry out the known polymerase chain reaction (PCR) process for amplifying the nucleic acid fragment.

2.1 Microfluidic Systems

"Microfluidics" generally refers to systems, devices, and methods for processing small volumes of fluids. Microfluidic systems can integrate a wide variety of operations for manipulating fluids. Such fluids may include chemical or biological samples. These systems also have many application areas, such as biological assays (for, e.g., medical diagnoses, drug discovery and drug delivery), biochemical sensors, or life science research in general as well as environmental analysis, industrial process monitoring and food safety testing.

One type of microfluidic device is a microfluidic chip. Microfluidic chips may include micro-scale features (or "microfeatures"), such as channels, valves, pumps, reactors and/or reservoirs for storing fluids, for routing fluids to and from various locations on the chip, and/or for reacting fluidic reagents.

However, existing microfluidic systems lack adequate mechanisms for allowing controlled manipulation of multiple fluids except via prescribed flow patterns, hence limiting the practicality with which the systems can be utilized in various chemical or biological assays. This is because real-world assays often require repetitive manipulation of different reagents for various analytical purposes.

Moreover, many existing microfluidic devices are restricted for one specific use and cannot be easily adapted or customized for other applications without being completely redesigned. These devices lack modularity, and therefore cannot share common device components that allow one design to perform multiple functions. This lack of flexibility leads to increased production costs as each use requires the production of a different system.

Furthermore, many existing microfluidic systems lack any means for straightforward end-point assays that are able to easily detect interactions or existence of analytes resulting from the assays. By way of example, visual detection of sample color changes after an assay is often used to evaluate the assay results Thus, there exists a need for improved microfluidic systems for processing fluids for analysis of biological or chemical samples, and in particular, in the detection and analysis of biologically active macromolecules derived from such samples such as DNA, RNA, amino acids and proteins. It is desired that the systems are mass producible, inexpensive, and preferably disposable. It is desired that the systems be simple to operate and that many or substantially all of the fluid processing steps be automated. It is desired that the systems be customizable, and be modular such that the system can be easily and rapidly reconfigured to suit various applications in which the detection of macromolecules is desired. It is also desired that the systems be able to provide straightforward and meaningful assay results.

Citation or identification of any reference in Section 2, or in any other section of this application, shall not be considered an admission that such reference is available as prior art to the present invention.

3. SUMMARY OF THE INVENTION

A microfluidic device is provided for analyzing a sample of interest comprising:

a) a microfluidic device body, wherein the microfluidic device body comprises:

i) a sample preparation area, ii) a nucleic acid amplification area, iii) a nucleic acid analysis area, and iv) a plurality of fluid channels interconnected in a network, and wherein each of the sample preparation area, the nucleic acid amplification area and the nucleic acid analysis area are fluidly interconnected to at least one of the other two areas by at least one of the fluid channels in the network.

A microfluidic device is also provided for analyzing a sample of interest comprising:

a) a microfluidic device body, wherein the microfluidic device body comprises:

i) a sample preparation area, ii) a nucleic acid amplification area, and iv) a plurality of fluid channels interconnected in a network, and wherein each of the sample preparation area and the nucleic acid amplification area are fluidly interconnected to the other area by at least one of the fluid channels.

In one embodiment, the microfluidic device can comprise a differential pressure source capable of exerting a positive pressure or a negative pressure with respect to ambient pressure on a selected area of the microfluidic device body.

In another embodiment, the microfluidic device can comprise a differential pressure delivery system operably connected to the differential pressure source and to the microfluidic device body.

In another embodiment, the microfluidic device can comprise at least one diaphragm disposed in or between particular or selected fluid channels for transforming a pressure from the differential pressure source to a desired open or closed position of the diaphragm.

In another embodiment, the sample preparation area comprises:

a sample intake reservoir;

a reservoir for a sample preparation reagent; and sample purification media;

wherein the sample intake reservoir, the reservoir for the sample preparation reagent, and the sample purification media are fluidly interconnected.

In another embodiment, the microfluidic device can comprise a sample purification media reservoir, wherein the sample purification media is disposed in the sample purification media reservoir.

In another embodiment, the sample purification media is disposed in one of the plurality of fluidic channels.

In another embodiment, the sample purification media is disposed in the bottom of the sample purification reservoir.

In another embodiment, the nucleic acid amplification area comprises:

a nucleic acid amplification reactor;

a nucleic acid amplification reagent reservoir; and a nucleic acid amplification product reservoir;

wherein the nucleic acid amplification reactor, the nucleic acid amplification reagent reservoir, and the nucleic acid amplification product reservoir are fluidly interconnected.

In another embodiment, the sample of interest is a fluid material, a gaseous material, a solid material substantially dissolved in a liquid material, an emulsion material, a slurry material, or a fluid material with particles suspended therein.

In another embodiment, the sample of interest comprises a biological material.

In another embodiment, the sample of interest comprises a suspension of cells in a fluid.

In another embodiment, the microfluidic device body comprises a plurality of layers of weak solvent-bonded polystyrene.

In another embodiment, the sample preparation area comprises a sample mixing diaphragm fluidically connected to the sample intake reservoir.

In another embodiment, the nucleic acid extraction media is a silica membrane.

In another embodiment, the microfluidic device body comprises a means for air-drying the sample purification media.

In another embodiment, the sample preparation area comprises a washing reservoir.

In another embodiment, the sample preparation area comprises a waste reservoir.

In another embodiment, the sample preparation area comprises an elution reservoir.

In another embodiment, the sample preparation reagent comprises magnetic beads.

In another embodiment, a sample purification reagent is disposed in the sample purification reservoir.

In another embodiment, the sample purification reagent is magnetic beads.

In another embodiment, the sample preparation reagent is a lysing reagent.

In another embodiment, the nucleic acid amplification reactor is a thermal cycling reactor.

In another embodiment, the bottom of the thermal cycling reactor is a thin layer of polystyrene.

In another embodiment, the bottom of the thermal cycling reactor is heated during thermal cycling by a heater that is not disposed on or in the microfluidic device body.

In another embodiment, the nucleic acid amplification is selected from the group consisting of polymerase chain reaction (PCR), reverse-transcriptase (RT-) PCR, Rapid Amplification of cDNA Ends (RACE), rolling circle amplification, nucleic Acid Sequence Based Amplification (NASBA), Transcript Mediated Amplification (TMA), and Ligase Chain Reaction.

In another embodiment, the nucleic acid analysis area comprises an area for detecting an interaction between the nucleic acid of interest and a probe for the nucleic acid of interest.

A method for detecting a nucleic acid of interest is also provided, comprising the steps of obtaining a sample suspected of containing the nucleic acid of interest; providing a microfluidic device; introducing the sample into the sample preparation area; preparing the sample for nucleic acid amplification; introducing the prepared sample into the nucleic acid amplification area; performing a nucleic acid amplification reaction in the nucleic acid amplification area to amplify the nucleic acid of interest; introducing the amplified nucleic acid of interest into the nucleic acid analysis area; and detecting the amplified nucleic acid of interest.

In one embodiment, the nucleic acid of interest is associated with a disease or disorder of interest.

In another embodiment, the detecting step comprises detecting an interaction between the amplified nucleic acid of interest and a probe for the nucleic acid of interest.

In another embodiment, the detecting step comprises visualizing color intensity, fluorescence intensity, electrical signal intensity or chemiluminescence intensity.

In another embodiment, the detecting step comprises generating an intensity value corresponding to at least one molecule of interest in the sample.

In another embodiment, the intensity value is selected from the group consisting of color intensity value, fluorescence intensity value and chemiluminescence intensity value, current or voltage.

In another embodiment, generating the color intensity value comprises:

analyzing an image corresponding to the sample to generate a plurality of pixels;

providing a plurality of numerical values for respective ones of the plurality of pixels; and producing numerical values to provide a color intensity value.

In another embodiment, the method further comprises computing a threshold value and comparing the color intensity value to the threshold value to detect the molecule of interest.

In another embodiment, the method further comprises storing at least one of the color intensity value and the threshold value in a database.

In another embodiment, the threshold value is computed using at least one negative control sample.

A method for determining presence of or predisposition for a disease or disorder of interest in a subject is also provided. The method comprises obtaining a sample from the subject, wherein the sample is suspected of containing a nucleic acid associated with the disease or disorder of interest; and detecting the nucleic acid associated with the disease or disorder of interest in the sample, wherein the detecting step comprises the steps of obtaining a sample suspected of containing the nucleic acid of interest; providing a microfluidic device; introducing the sample into the sample preparation area; preparing the sample for nucleic acid amplification; introducing the prepared sample into the nucleic acid amplification area; performing a nucleic acid amplification reaction in the nucleic acid amplification area to amplify the nucleic acid of interest; introducing the amplified nucleic acid of interest into the nucleic acid analysis area; and detecting the amplified nucleic acid of interest, wherein detecting the amplified nucleic acid of interest is associated with presence of or predisposition for the disease or disorder of interest.

In one embodiment, the detecting step comprises determining an amount (or level) of the amplified nucleic acid of interest and wherein the method further comprises comparing the amount (or level) with a preselected amount (or level) of the nucleic acid of interest.

In another embodiment, a difference between the amount (or level) with the preselected amount (or level) is indicative of presence or predisposition for the disease or disorder of interest.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1 is a three-dimensional view an embodiment of the microfluidic device ("chip") that has three functional areas, a sample preparation area 101, a nucleic acid amplification area 102 and a nucleic acid analysis area 103 for carrying out an end-point detection assay. Reagent reservoir 111. Reservoirs for analysis area 113. Waste reservoir 114.

FIG. 2 is an isometric exploded view of the microfluidic device of FIG. 1, showing three layers of the microfluidic device (for clarity, the continuous membrane is not shown).

FIG. 3A is a top view of the embodiment of the microfluidic device in FIG. 1, showing the sample preparation area ("nucleic acid (NA) extraction area"), the nucleic acid amplification area (in this embodiment, a "PCR area") and the nucleic acid analysis area ("RDB area"). Also shown is the layout of valves, microfluidic channels, through-holes, and a low density DNA filter on the device. In this embodiment, a reverse dot blot (RDB) end-point detection assay can be performed in the nucleic acid analysis area. Waste; waste reservoir.

FIG. 3B is a top view of the embodiment of the microfluidic device in FIG. 1, showing the sample preparation area 101, the nucleic acid amplification area 102 (comprising a nucleic acid amplification reactor 112) and the nucleic acid analysis area 103, and the layout of valves, microfluidic channels and through-holes on the device. Reservoirs for analysis area 113.

Figure 1:
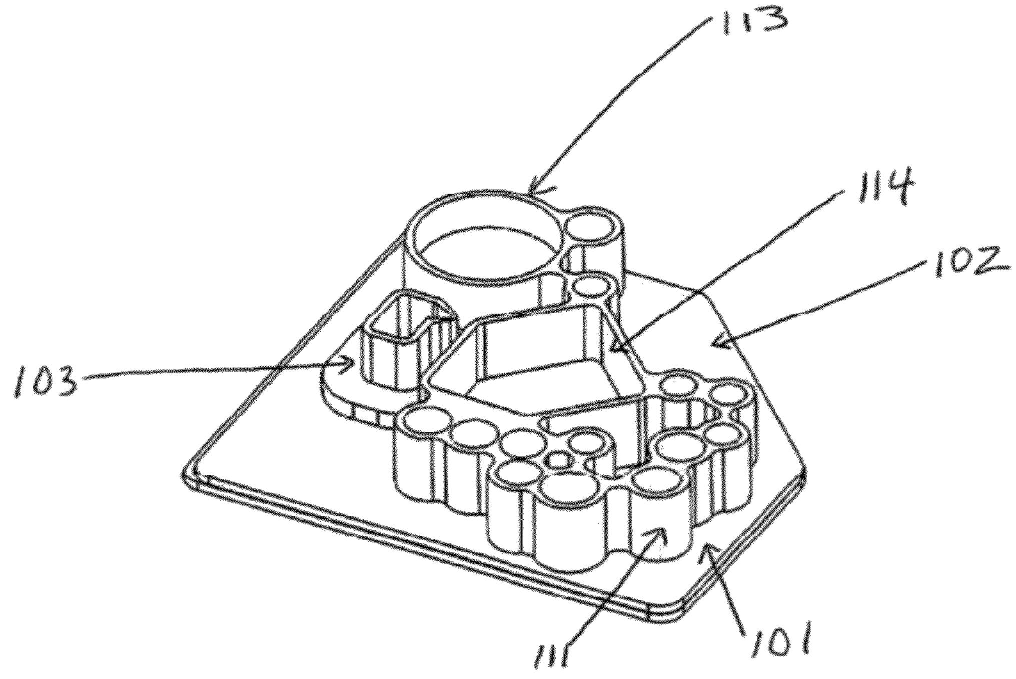
Figure 7:
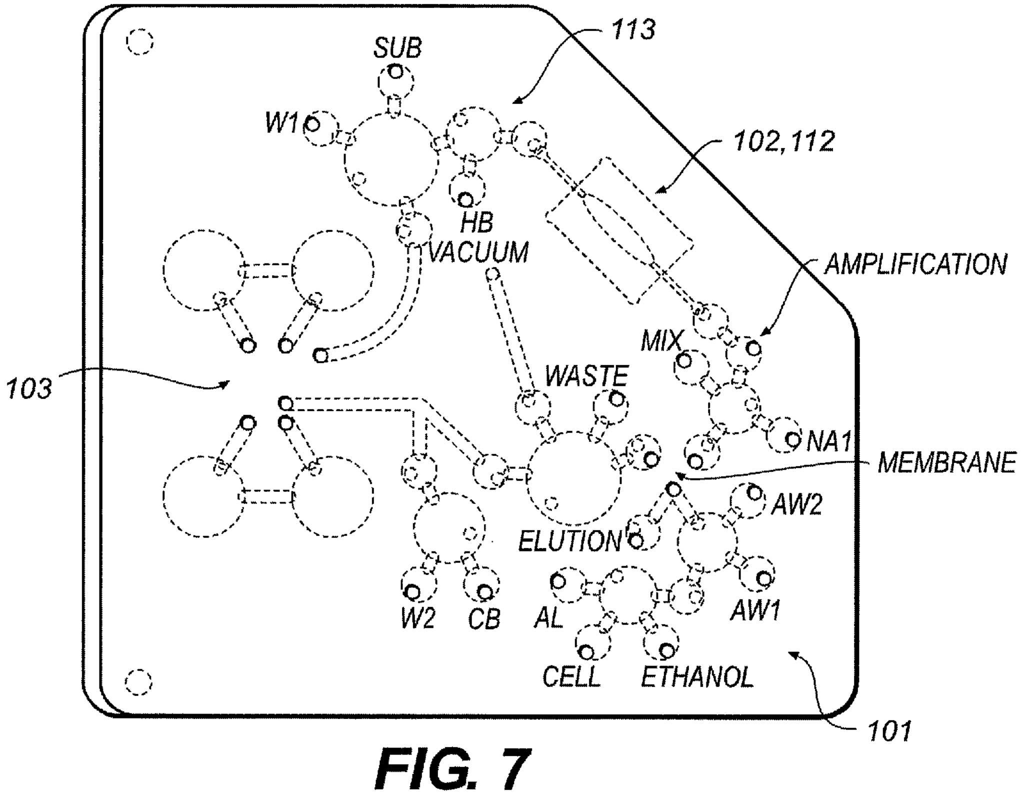

FIG. 7 is a top view of the embodiment of the microfluidic device in FIG. 1, showing a map of the functional areas of the device, and indicating the locations of reagents in reservoirs. Sample preparation area 101. Nucleic acid amplification area 102 (comprising a nucleic acid amplification reactor 112). Nucleic acid analysis area 103, and the layout of valves, microfluidic channels and through-holes on the device. Reservoirs for analysis area 113.

Figure 8:
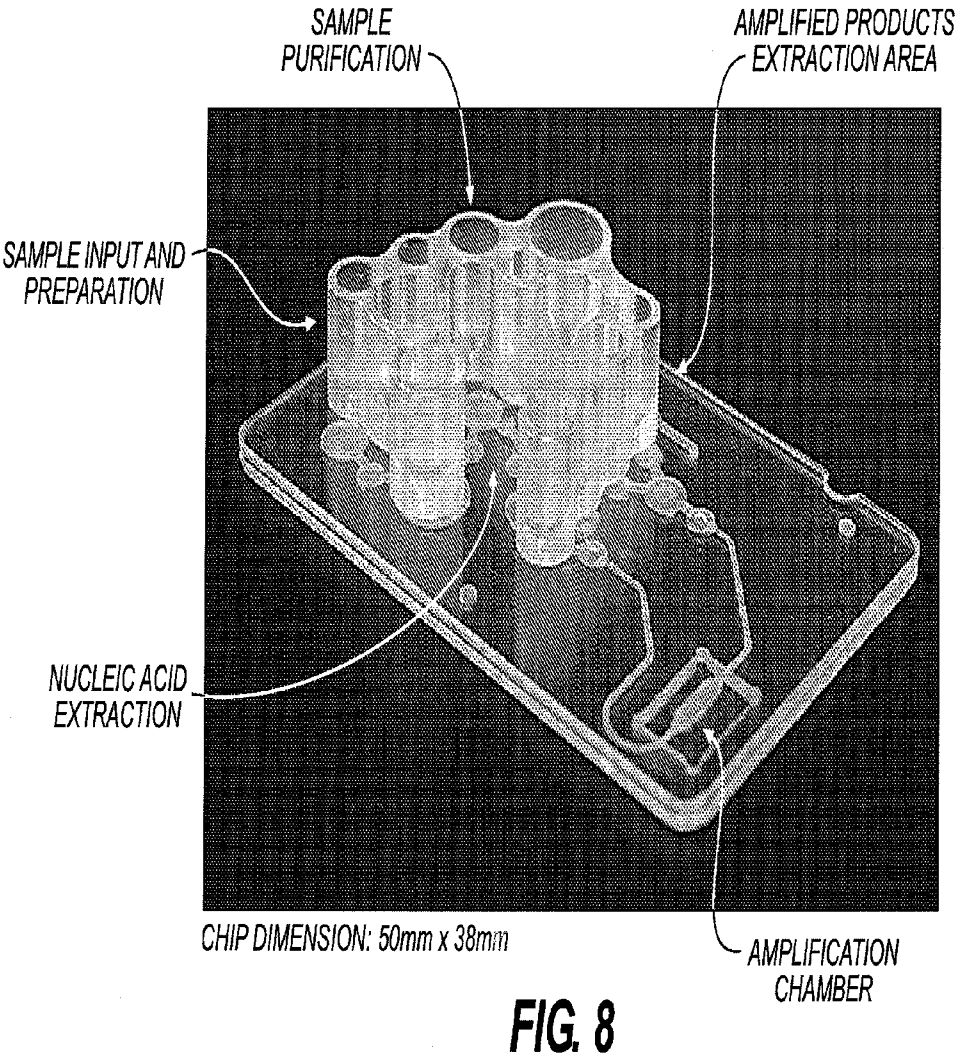

FIG. 8 shows another embodiment of the microfluidic device with two functional areas, the sample preparation area and the nucleic acid amplification area. As indicated by arrows, the sample preparation area comprises reservoirs for sample input and preparation, sample purification and nucleic acid extraction. The nucleic acid amplification area comprises a nucleic acid amplification reactor ("amplification chamber"). This embodiment of the device also comprises a nucleic acid amplification products extraction area ("amplified products extraction area"), which is an area in which amplicons are extracted from the microfluidic device after nucleic acid amplification is complete. This particular embodiment of the device has dimensions of 50 mm×38 mm.

Figure 9:
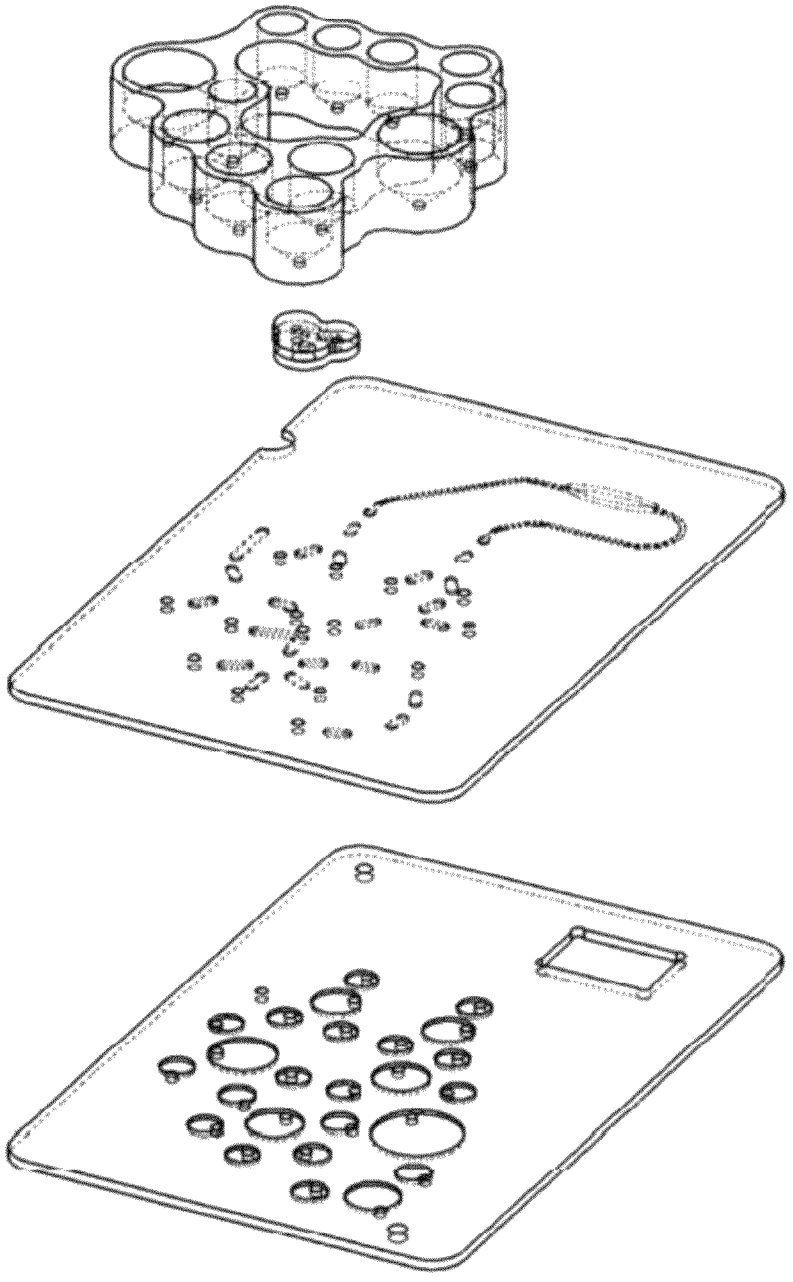

FIG. 9 is an exploded view of the embodiment of the microfluidic device depicted in FIG. 8, showing three layers of the microfluidic device (for clarity, the continuous membrane is not shown).

Figure 10:
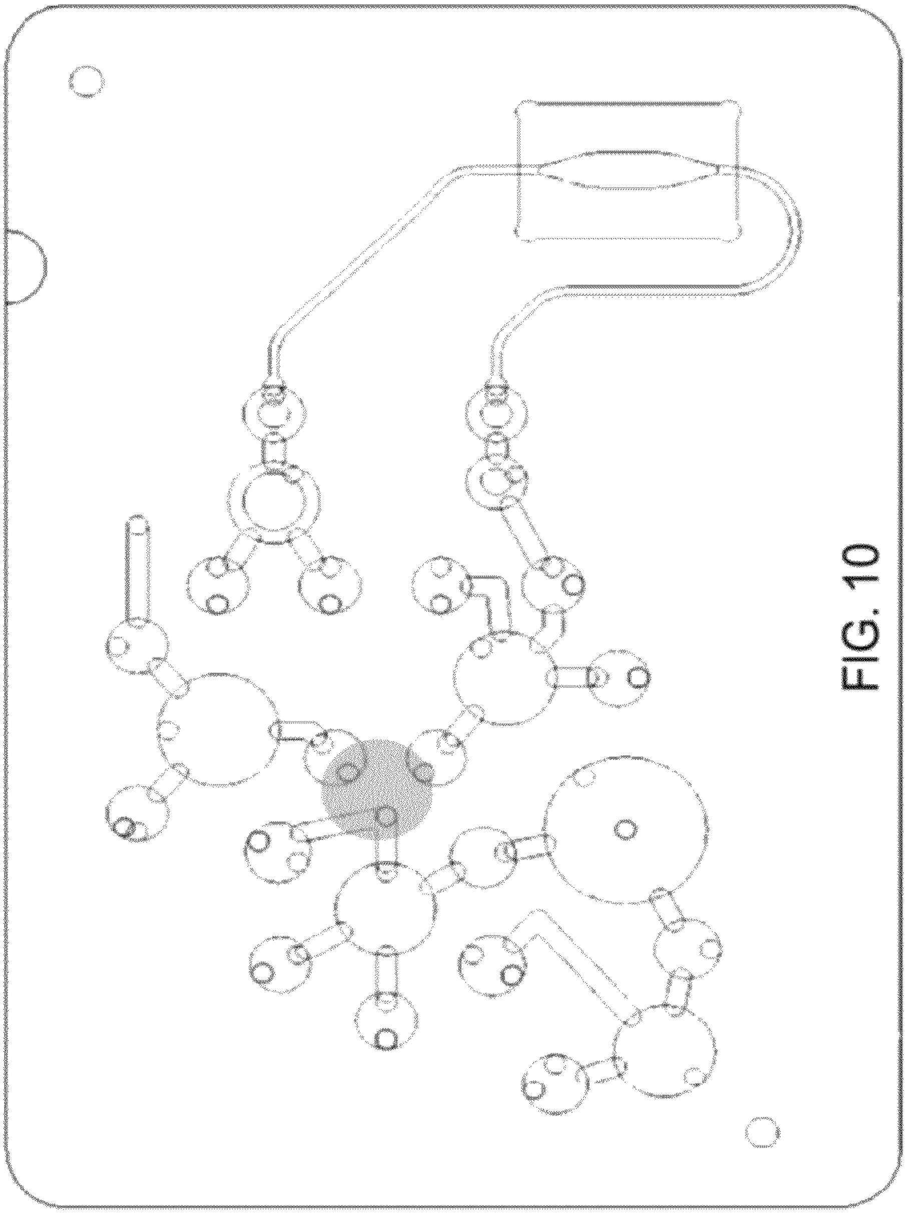

FIG. 10 is a diagram of the top view of the microfluidic device of FIG. 8, showing a map of the pumps, valves, amplification reactor, microfluidic channels and through-holes on particular layers of the device.

Figure 11:
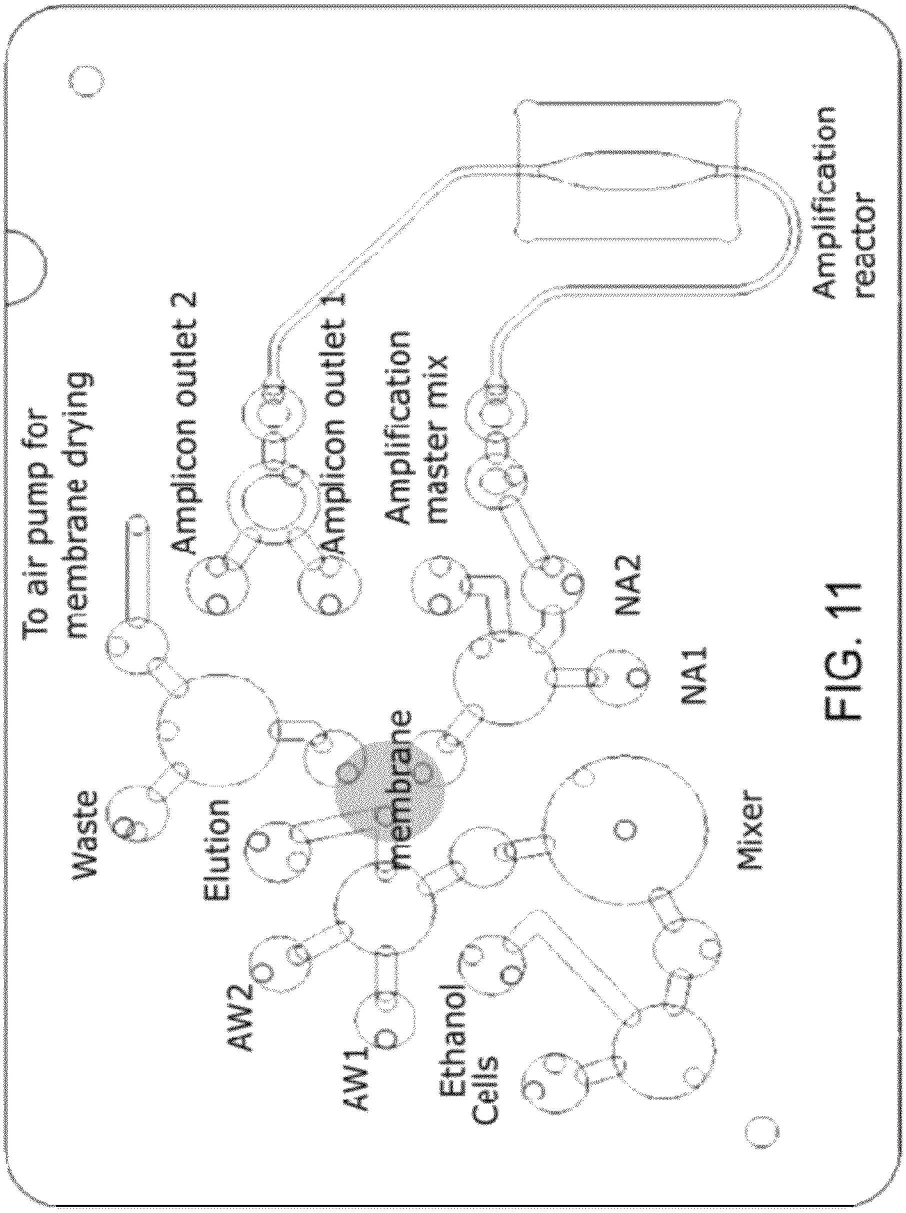

FIG. 11 is a diagram of the top view of the microfluidic device of FIG. 8, showing a map of the functional areas of the device, and indicating the locations of reagents in the plurality of reagent reservoirs (e.g. Cells, Ethanol, Mixer, Waste, Elution, NA1, NA2, AW1, AW2).

FIGS. 12-16. Another embodiment of the microfluidic device ("chip") of the invention that has two functional areas, a sample preparation area and a nucleic acid amplification area, but does not have an on-chip nucleic acid analysis area.

Figure 12:
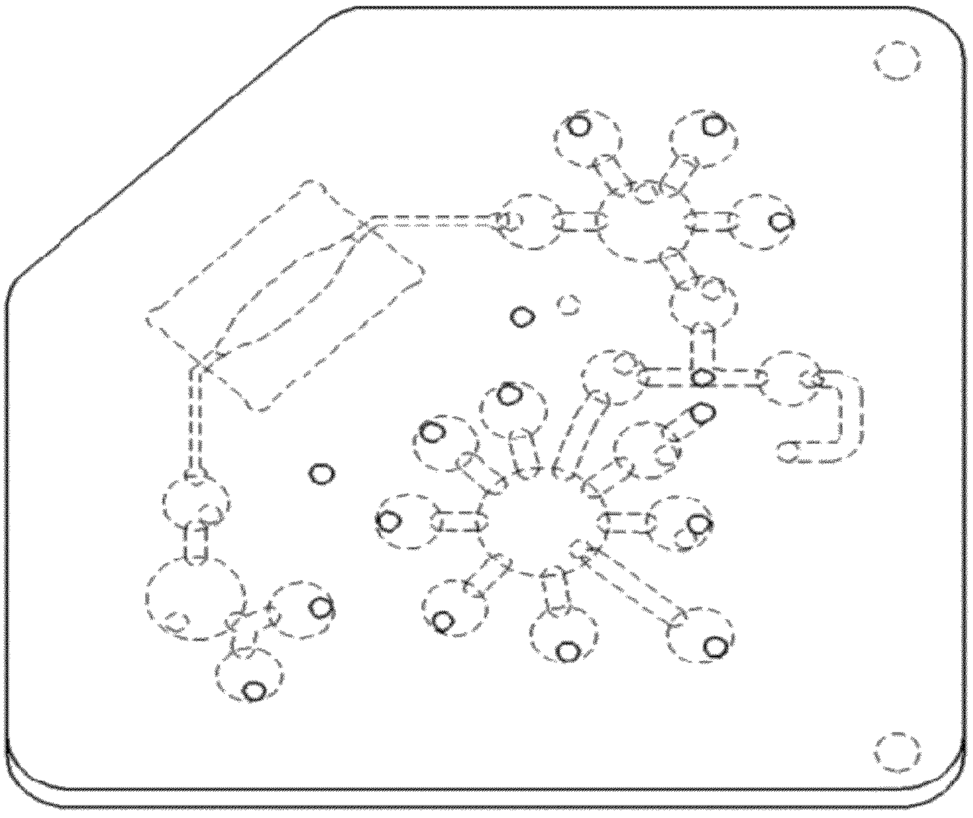

FIG. 12. Top view showing the layout of the valves and channels without showing the reservoirs.

Figure 13:
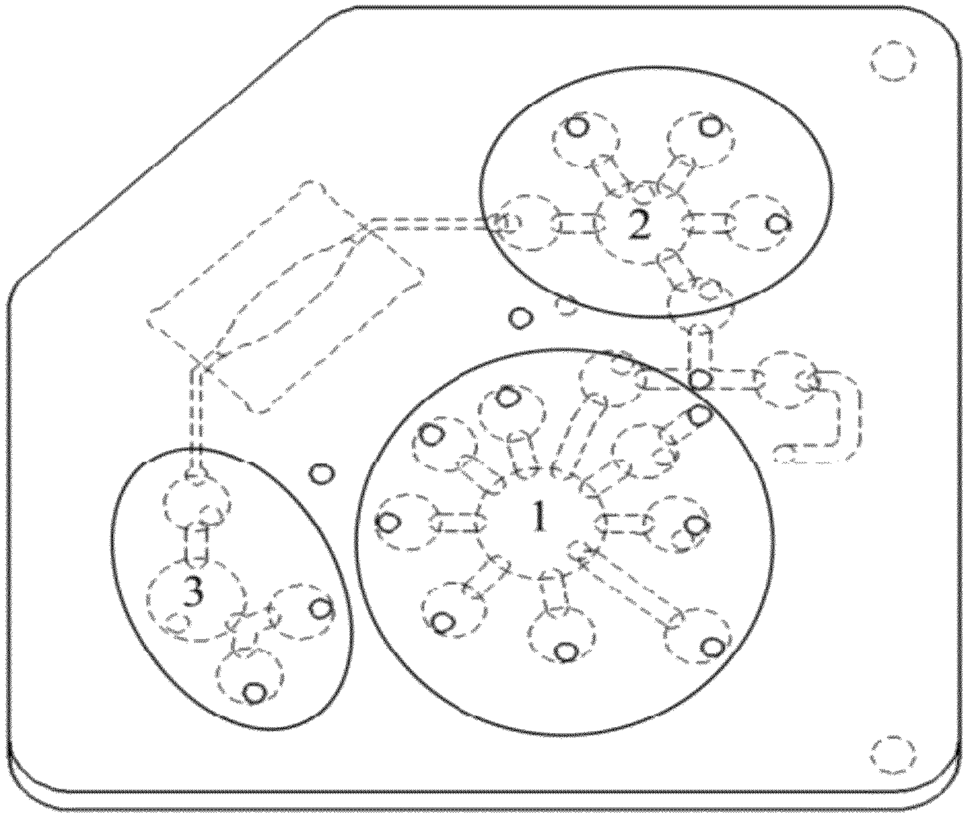

FIG. 13 shows the layout of the embodiment of the microfluidic device shown in FIG. 12, with three groups of bi-directional pumps depicted: for sample preparation, for nucleic acid amplification reagent preparation and for loading.

Figure 14:
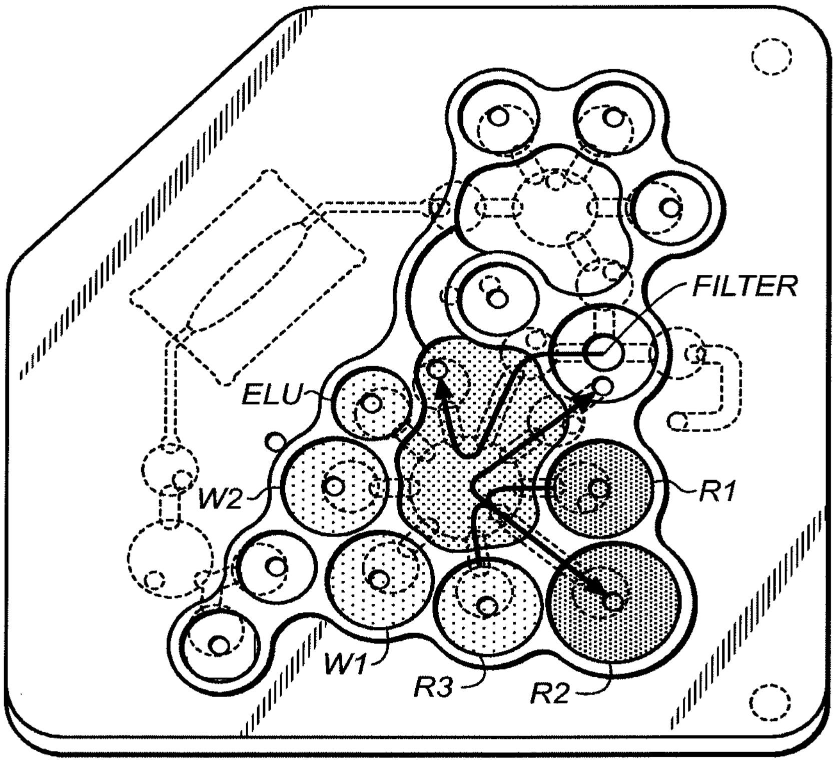
Figure 15:
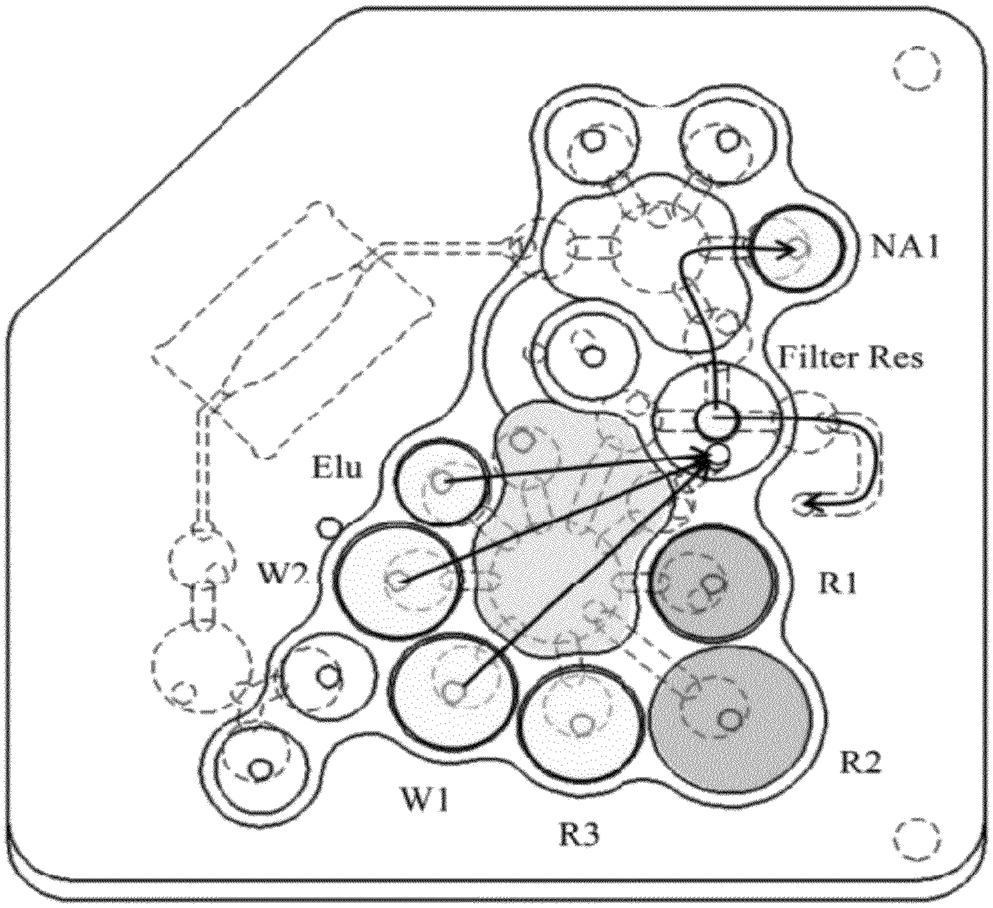
Figure 16:
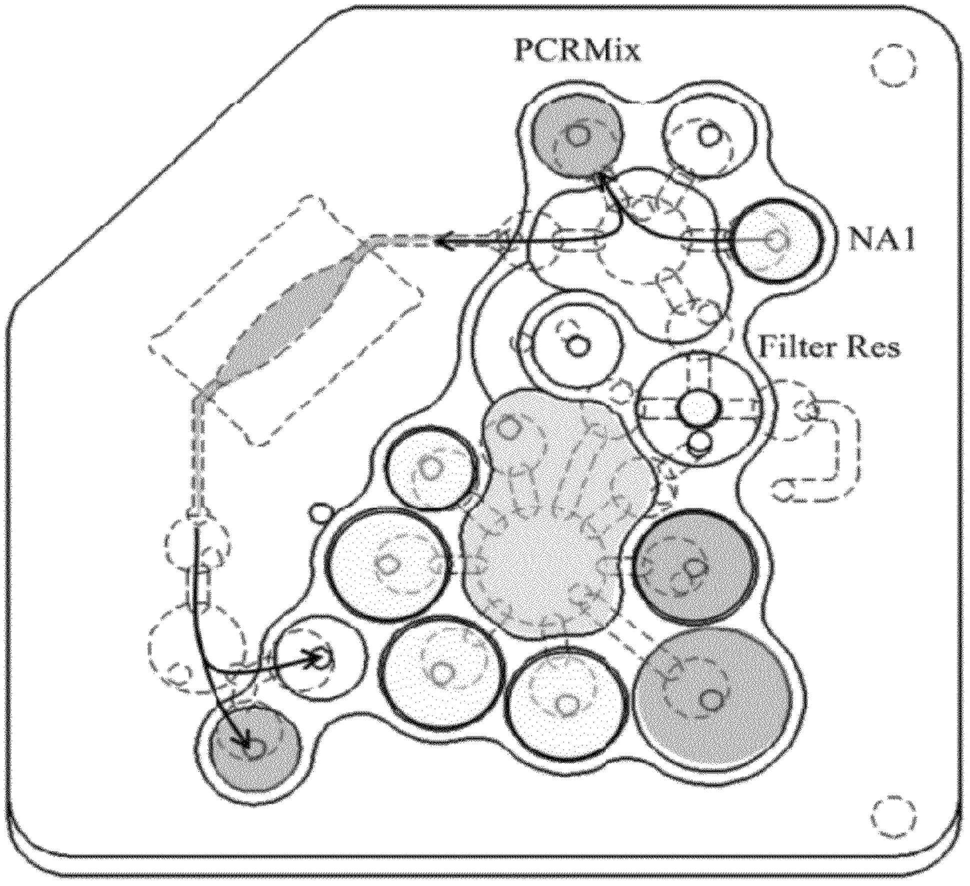

FIGS. 14-16 are diagrams of the operation of the embodiment of the microfluidic device shown in FIG. 12. The arrows show the progression of the *E. coli* sample as it was processed on the device.

Figure 17:
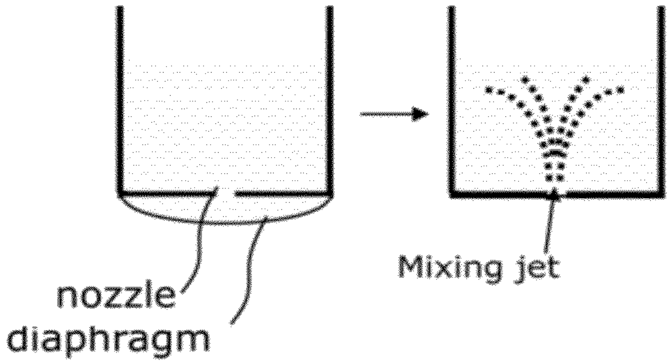

FIG. 17 shows an embodiment of the bottom of a chamber of the device, in which a diaphragm arranged over an opening ("nozzle") of the chamber can be used to produce a mixing jet to mix the contents of the chamber.

Figure 18:
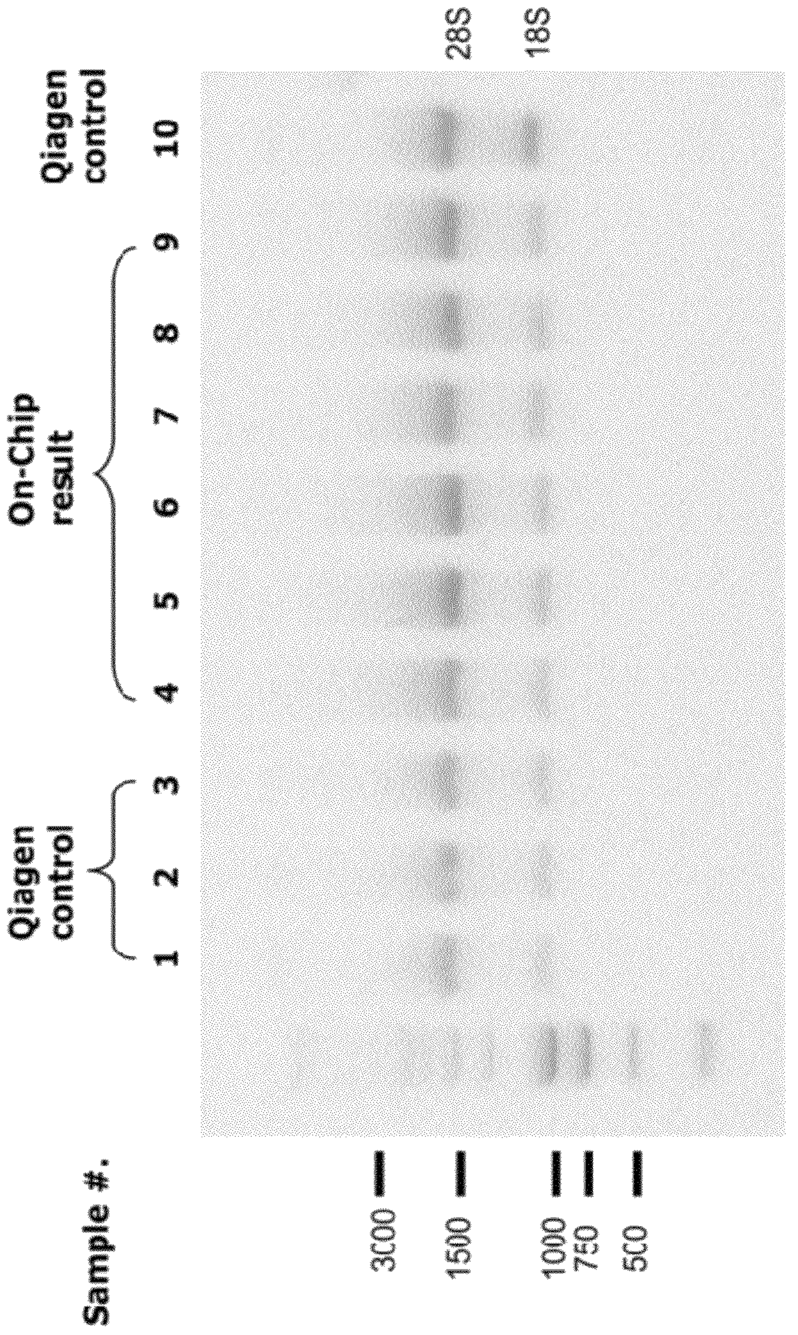

FIG. 18 shows comparative results obtained with a microfluidic device according to an embodiment of the invention and a control (Qiagen RNEasy kit). 1% agarose gels of RNA isolated from HEK293T cells using Qiagen RNeasy extraction/purification methods (lanes 1-3,10) and the microfluidic device (lanes 4-9). Molecular weight markers shown on left.

Figure 19:
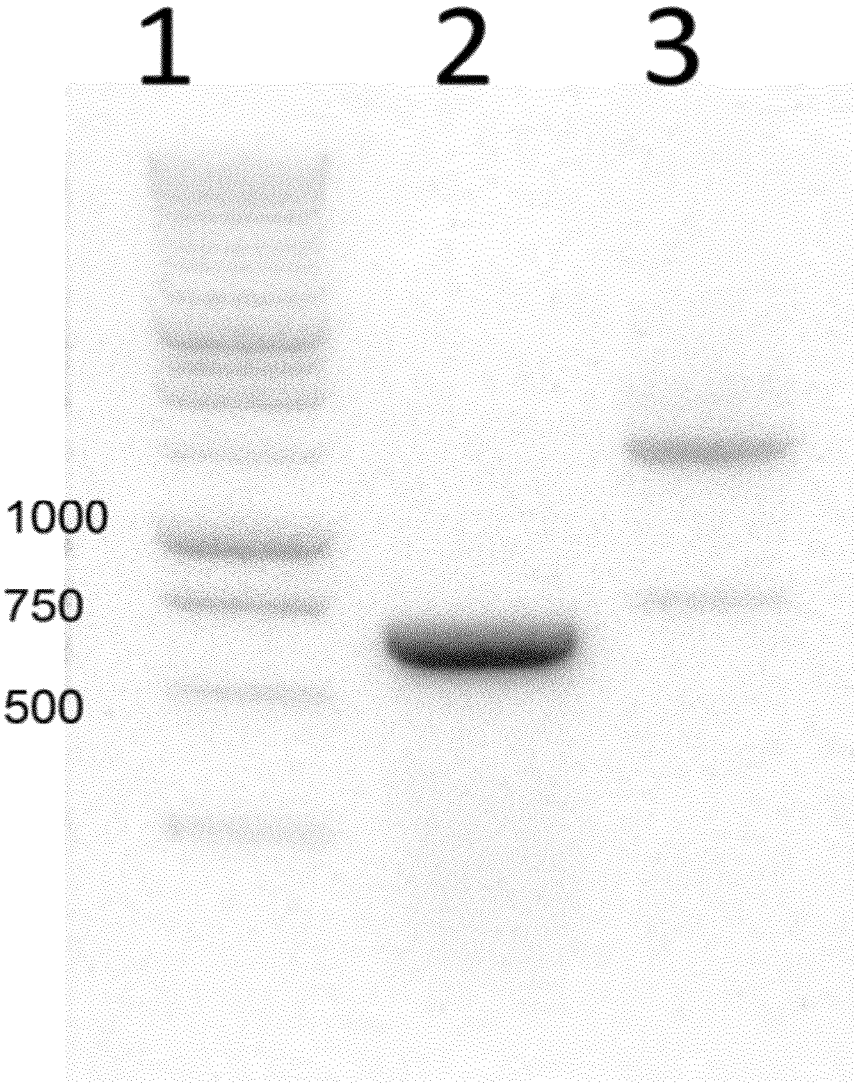

FIG. 19. Lane 1, DNA standards; Lane 2, amplicon product from RT-PCR performed on-chip, Lane 3, input RNA (1 μl).

RNA was generated from HEK 293T cells. Primers recognizing beta-actin were used to generate the cDNA product and to amplify actin cDNA via PCR.

Figure 20:
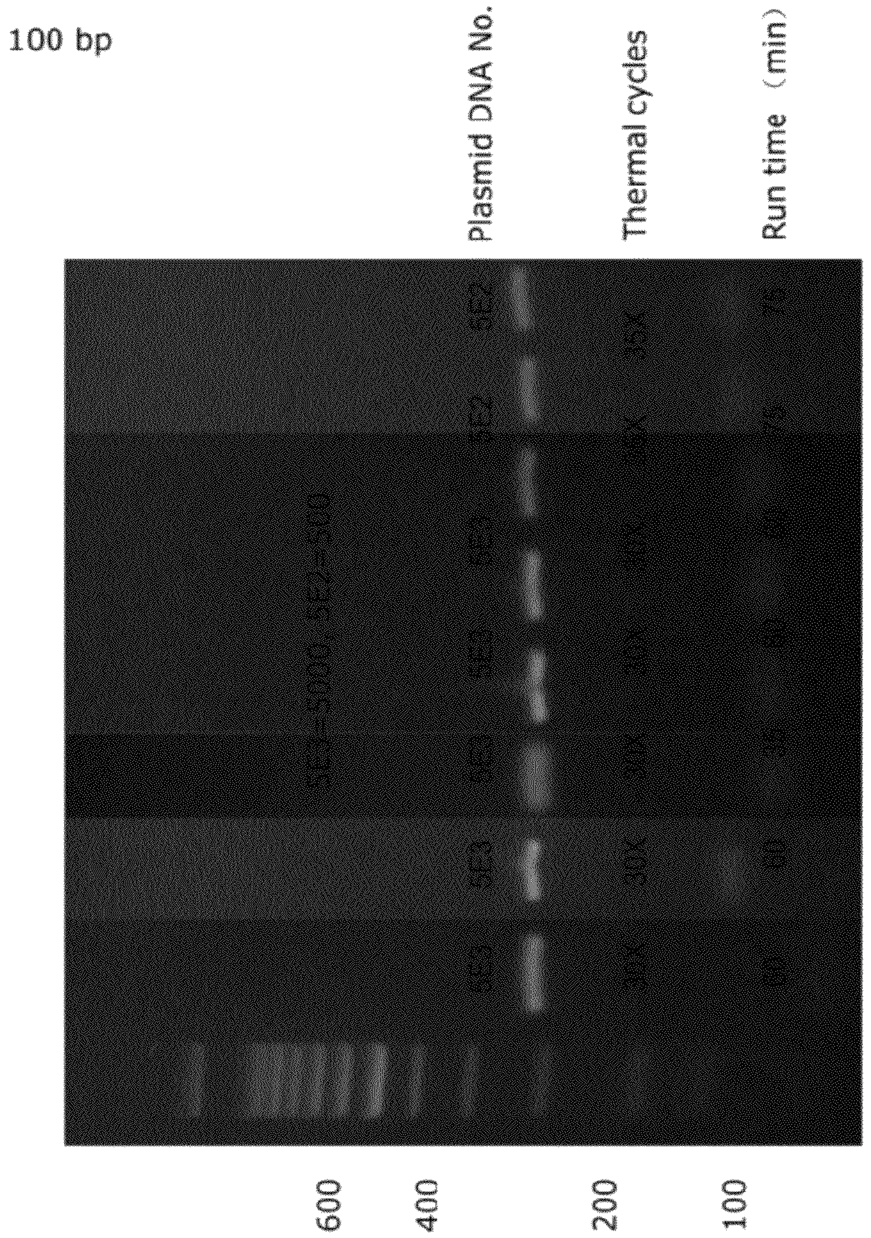

FIG. 20 shows on-chip repeatability for eight PCR runs for varying thermal cycles and run times as shown.

Figure 21:
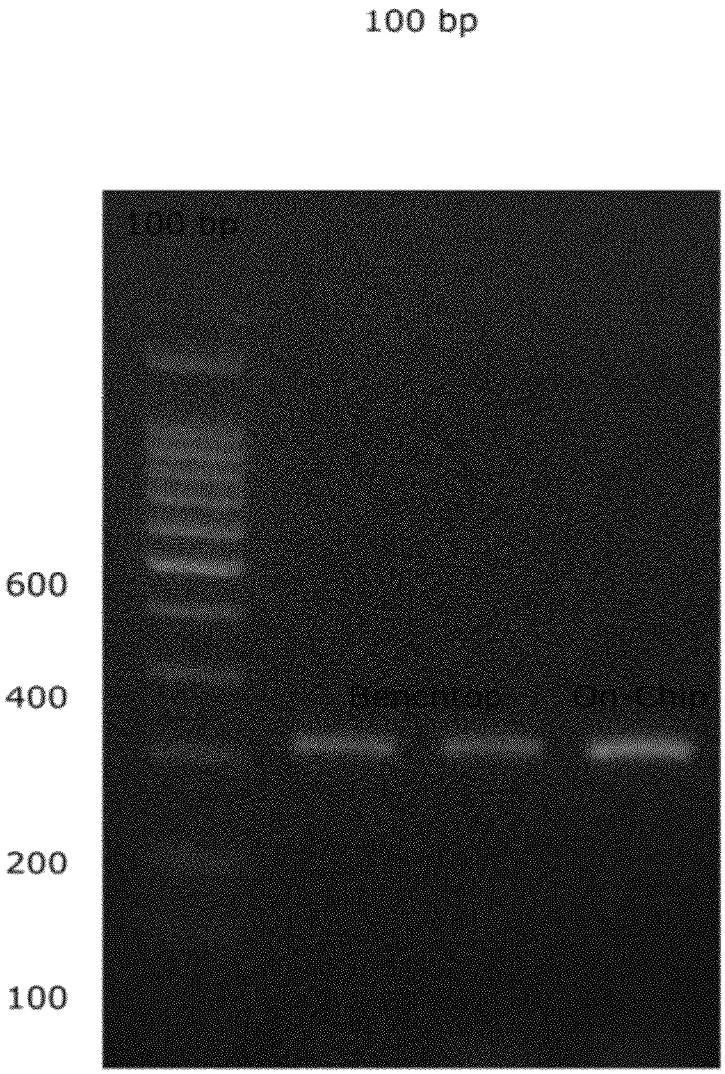

FIG. 21. PCR Comparison. $5\times10^3$ copies of plasmid (prlpGL3) were amplified through 30 cycles of PCR using either a BioRad MJ Mini Thermocycler (lanes 2 and 3) or the microfluidic device (lane 4). Molecular weight markers shown in lane 1.

Figure 22:
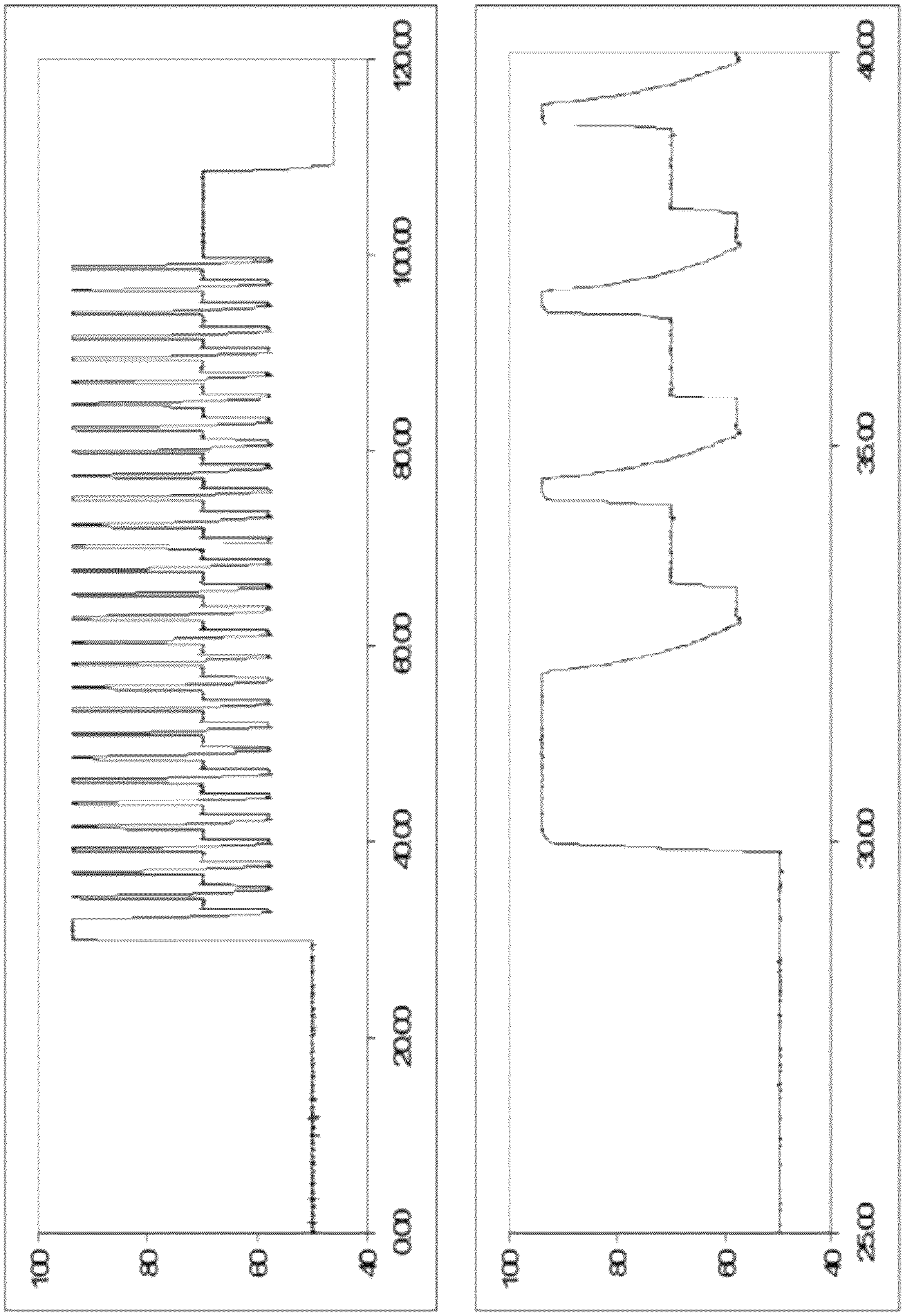

FIG. 22 shows a typical cycle from the PCR thermal cycler used in this experiment in conjunction with the microfluidic device. The graph at the bottom is an expanded view of the first four cycles shown in the top graph.

Figure 23:
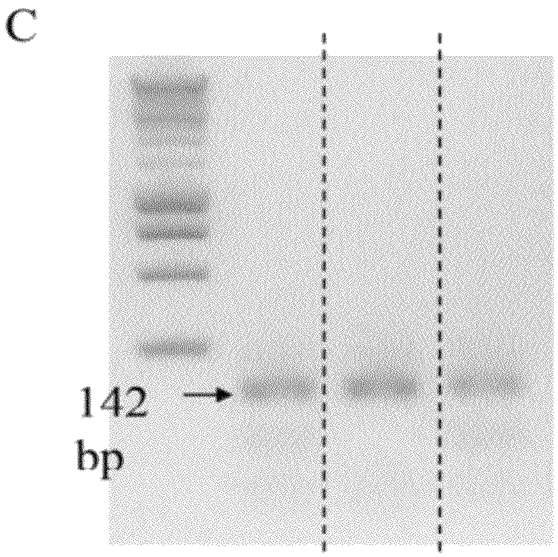

FIG. 23 shows the results of a RT-PCR protocol run on the microfluidic device. HIV RNA was isolated using bench top (bt) and on-chip protocols.

Figure 24:
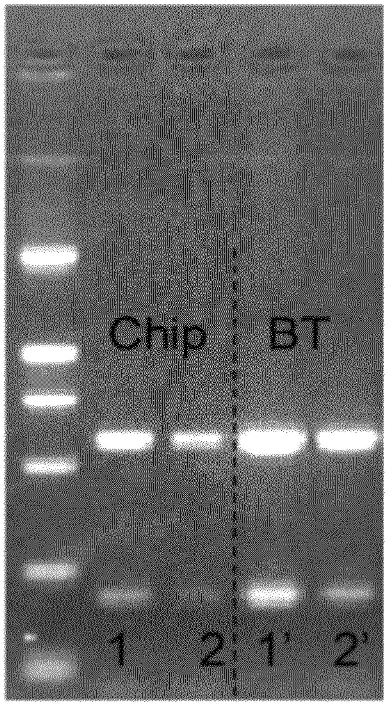

FIG. 24. Detection of β-thalassemia genes in whole blood. After 30 cycles of PCR, two identical samples that were PCR amplified in parallel using either a bench top thermocycler (lanes 4-5) or the microfluidic device (lanes 2-3) were analyzed on agarose gels. Lane 1 represents molecular weight standards.

Figure 25:
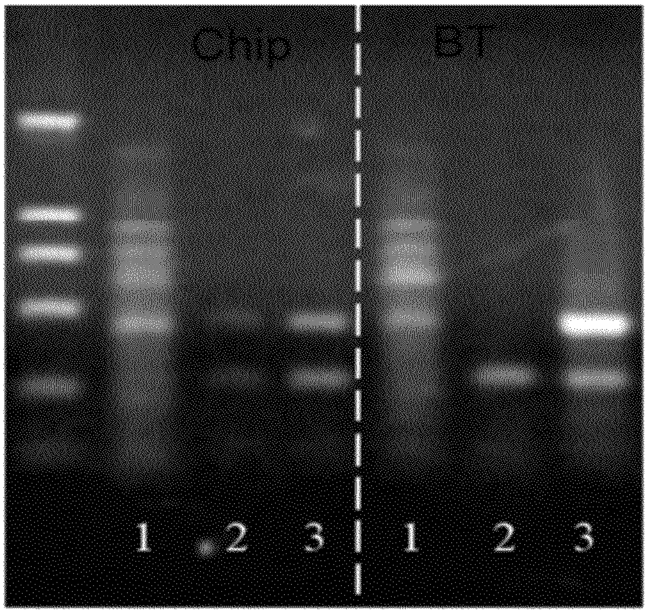

FIG. 25. Results of HPV amplification using either bench top PCR methods or the microfluidic device.

Figure 26:
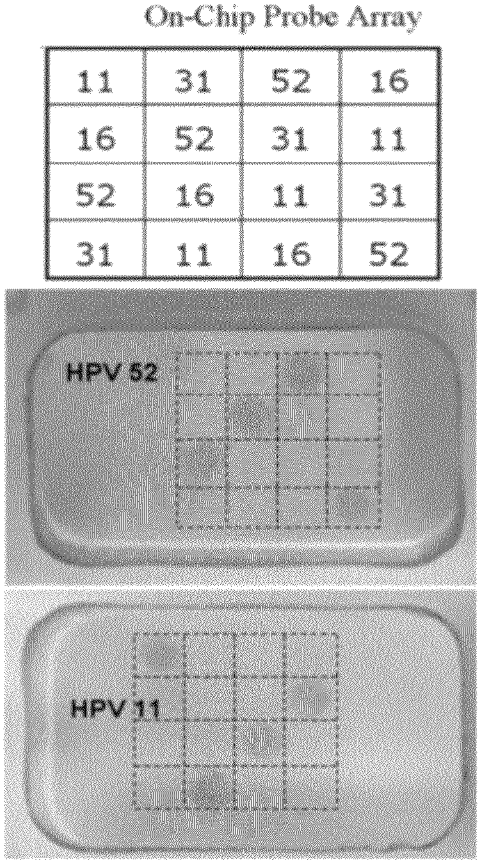

FIG. 26. On-chip probe arrays for HPV serotype detection by reverse dot blot (RDB). HPV-52 (top) and HVP-11 (bottom) were correctly detected.

Figure 27:
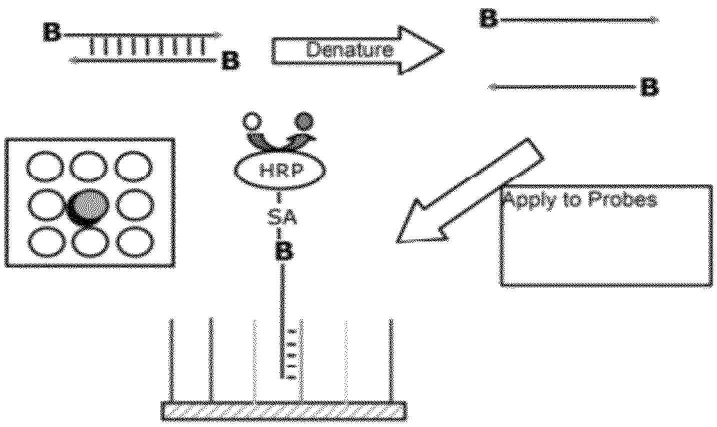

FIG. 27. Schematic diagram of RDB protocol.

Figure 28:
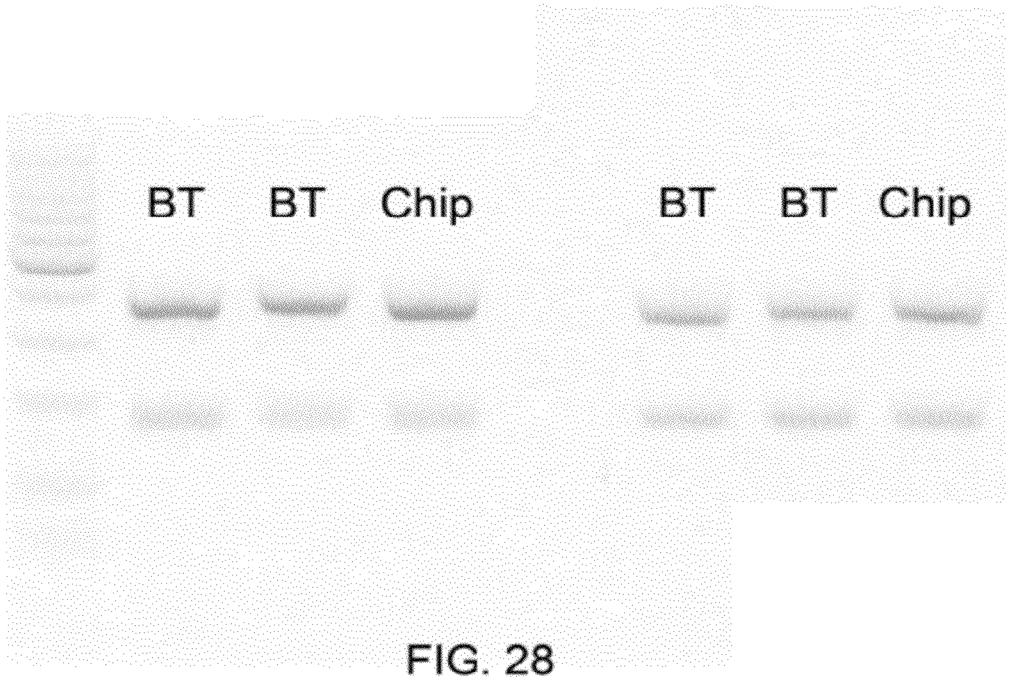

FIG. 28 shows a comparison between two chips processing 1,000 *E. coli* loaded into apple juice. The loaded juice was prepared and the DNA purified on-chip then two 1 μl aliquots were removed and amplified on the bench top and the remaining purified DNA was amplified on-chip. The product was removed and analyzed on gel as shown. Lane 1 and Lane 2 of each chip's product represent the aliquot which was amplified on the bench top and Lane 3 in each case represents the on-chip amplified product.

Figure 29:
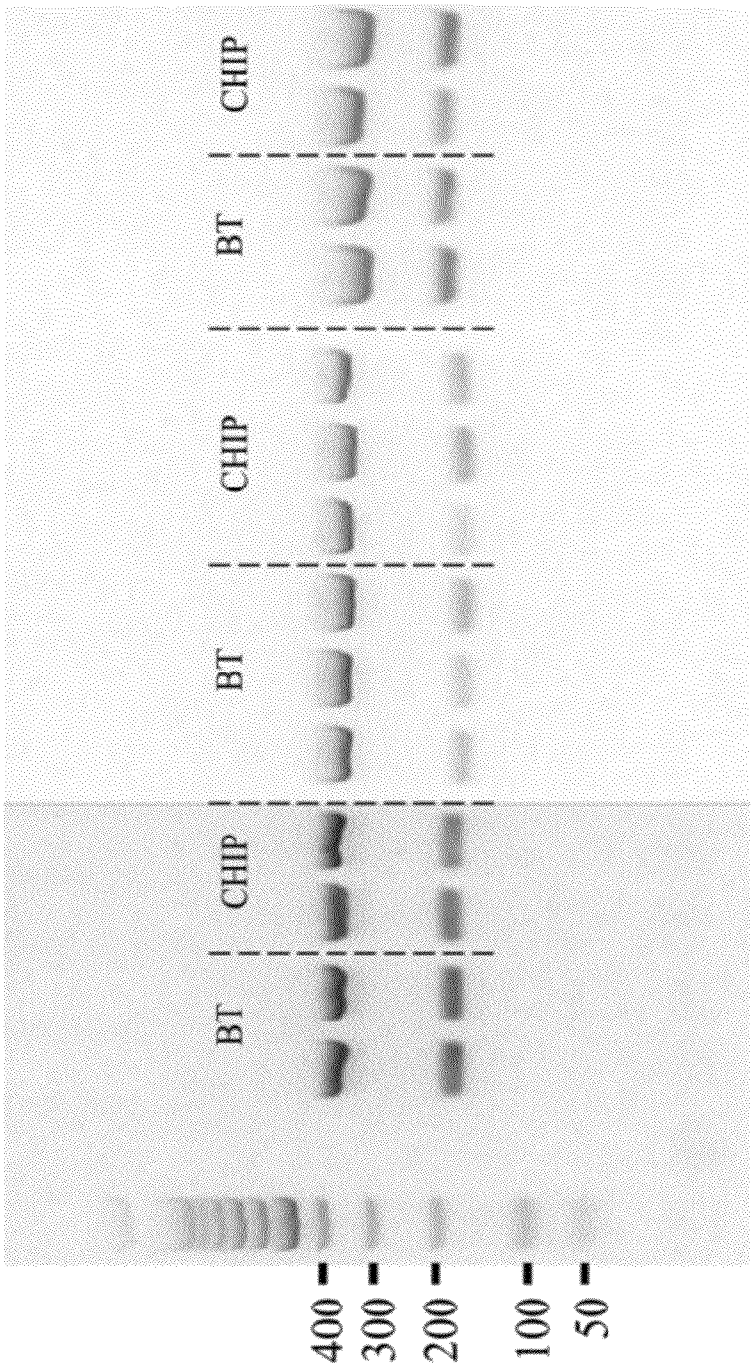

FIG. 29 shows a comparison of bench top and on-chip PCR results using on-chip extracted DNA. *E. coli* loading ranges were from $5\times10^3$/μl.-$1\times10^4$/μl.

Figure 30:
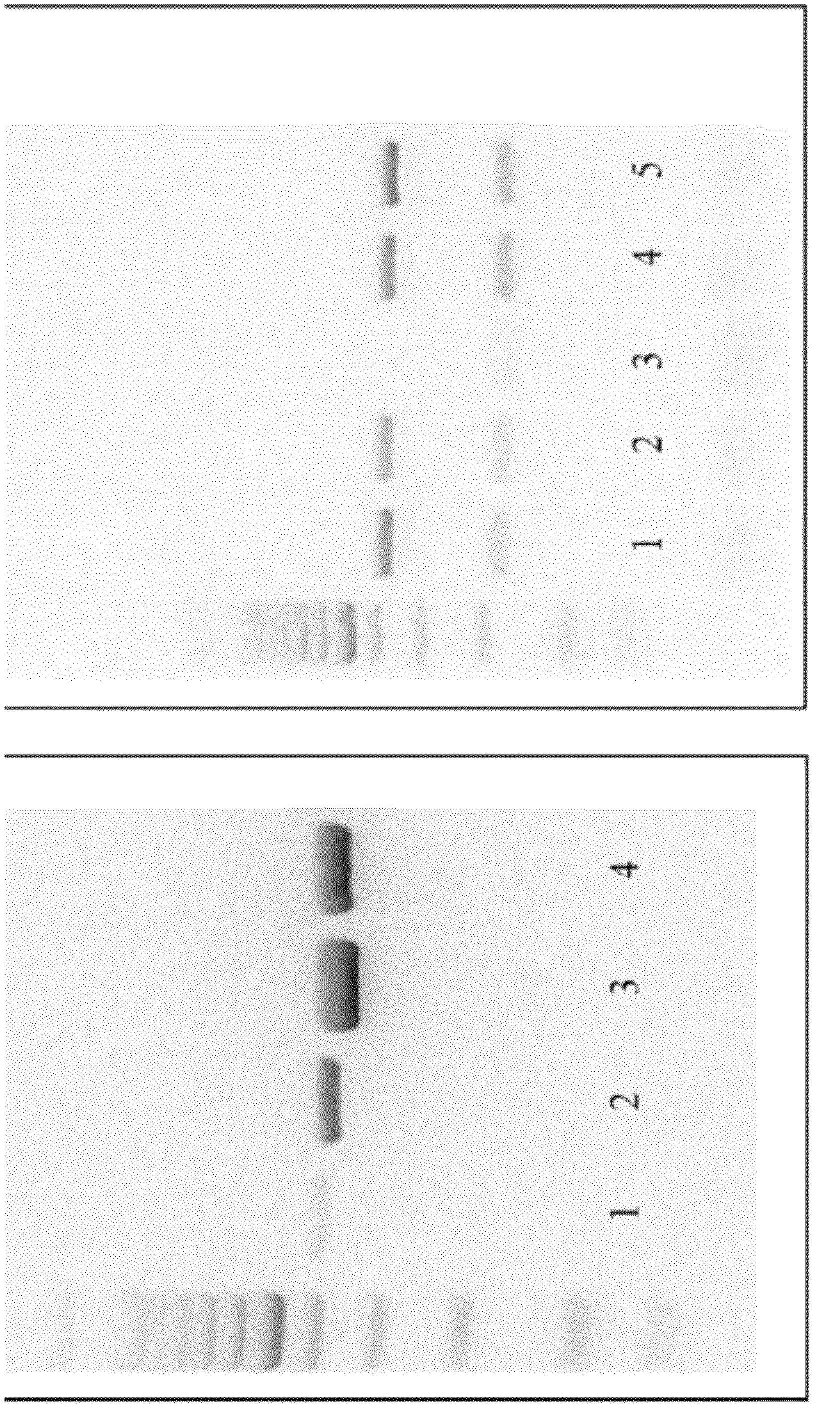

FIG. 30. A. Analysis of 500,000 *E. coli* introduced into apple cider comparing "bench top" PCR analysis (lane 3) and the microfluidic device analysis (lane 4). Lanes 1 and 2 represent the negative and positive controls, respectively. B. Analysis of 100,000 *E. coli* introduced into apple cider comparing "bench top" PCR analysis (lane 3) and the microfluidic device analysis (lane 4). Lanes 1 and 2 represent the negative and positive controls, respectively.

Figure 31:

FIG. 31. Analysis of 500,000 *E. coli* introduced into apple cider comparing "bench top" PCR analysis (lanes 2-3) and the microfluidic device analysis (lanes 4-5). Lane 1 represents the negative control.

Figure 32:
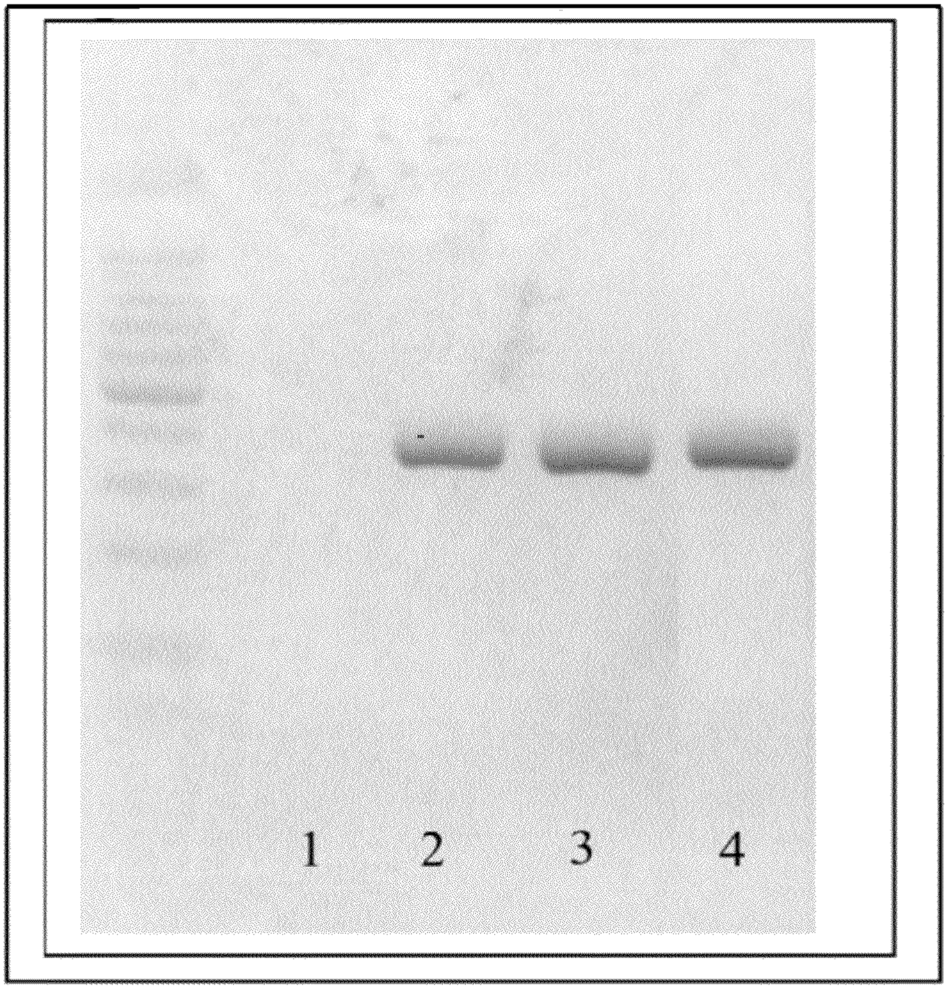

FIG. 32: Analysis of 500,000 *E. coli* introduced into PBS comparing "bench top" PCR analysis (lanes 2-3) and the microfluidic device analysis (lanes 4-5). Lane 1 represents the negative control.

Figure 33:
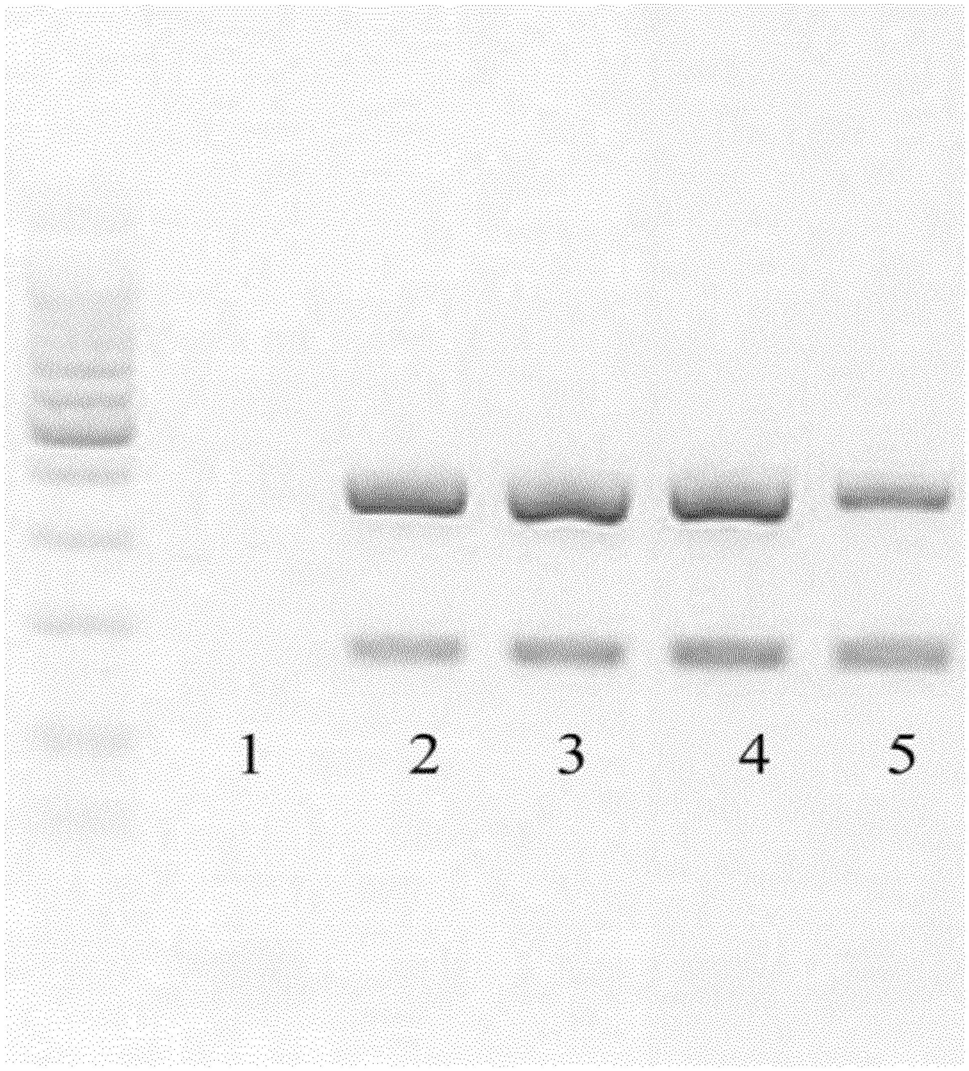

FIG. 33. Analysis of 10,000 *E. coli* introduced into apple juice comparing "bench top" PCR analysis (lanes 2-3) and the microfluidic device analysis (lanes 4-5). Lane 1 represents the negative control.

Figure 34:
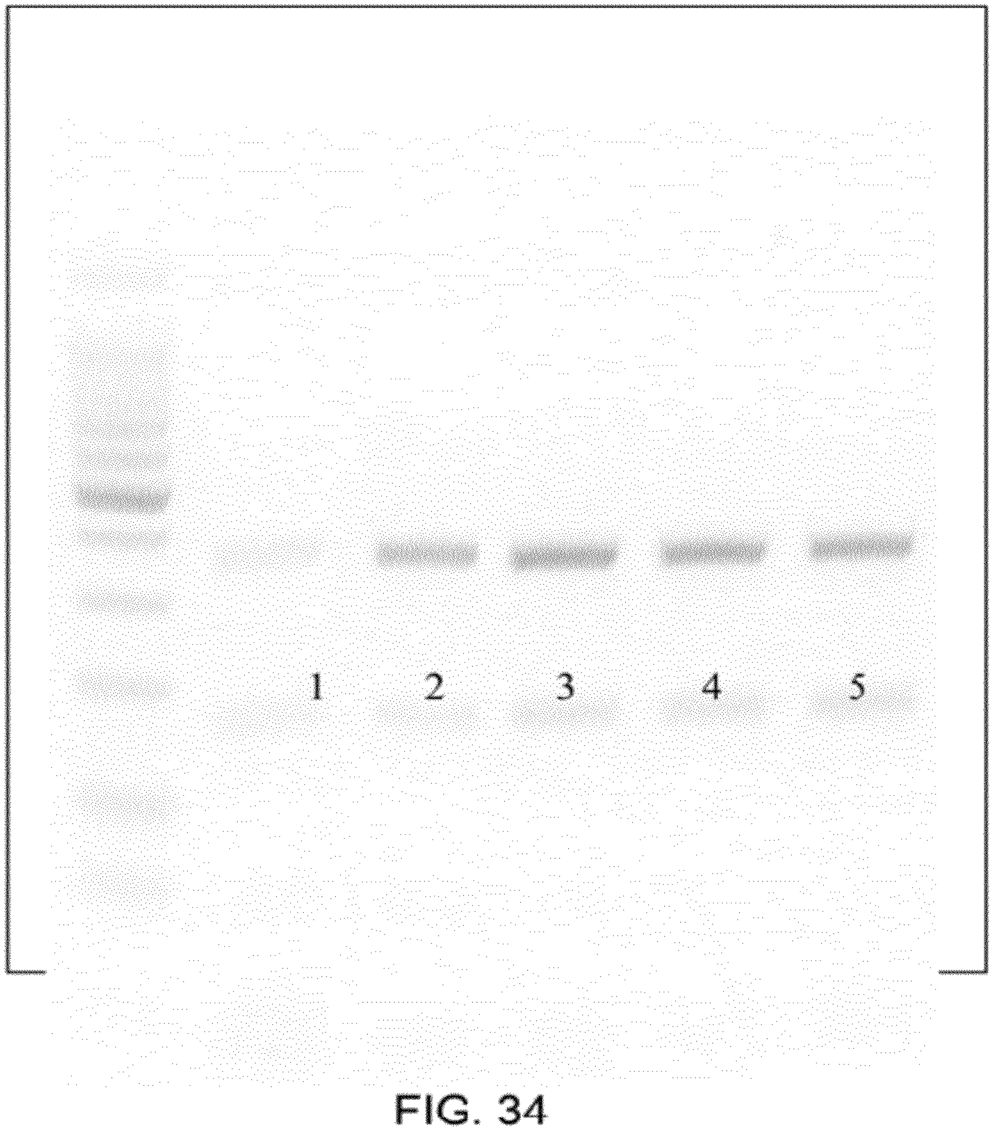

FIG. 34. Analysis of 1,000 *E. coli* introduced into apple juice comparing "bench top" PCR analysis (lanes 2-3) and the microfluidic device analysis (lanes 4-5). Lane 1 represents the negative control.

Figure 35:
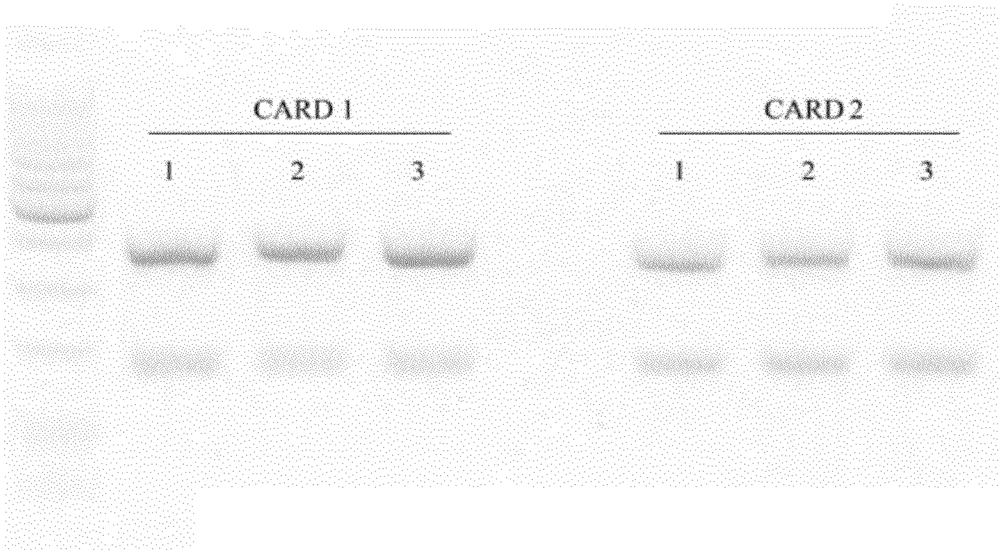

FIG. 35. Comparison of amplicons obtained from two different microfluidic device runs. The results obtained from a complete run of each microfluidic device (lanes 3 for the gel analysis from the products generated from each microfluidic device) were indistinguishable from the results obtained by "bench top" PCR amplification of DNA that was obtained from the same microfluidic device and amplified separately (lanes 1 and 2).

Figure 36:
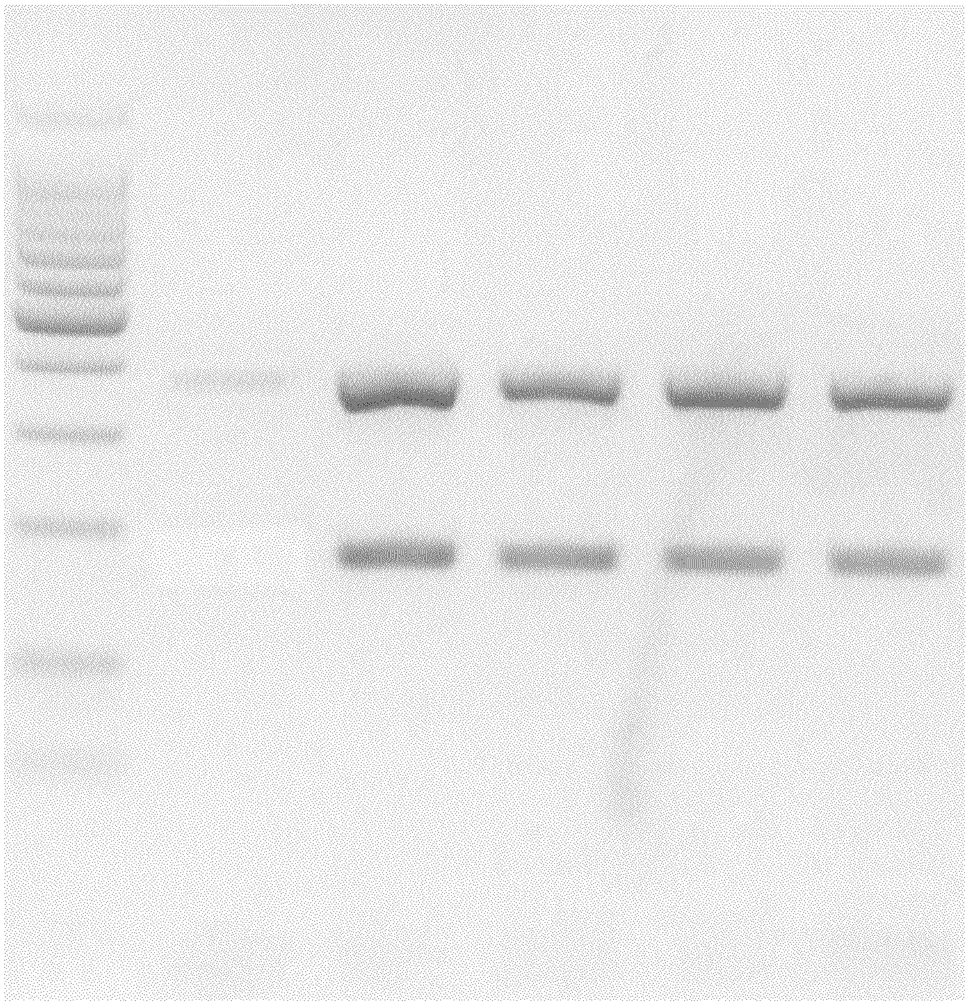

FIG. 36. Analysis of 1,000,000 *E. coli* introduced into skim milk comparing "bench top" PCR analysis (lanes 2-3) and the microfluidic device analysis (lanes 4-5). Lane 1 represents the negative control.

Figure 37:
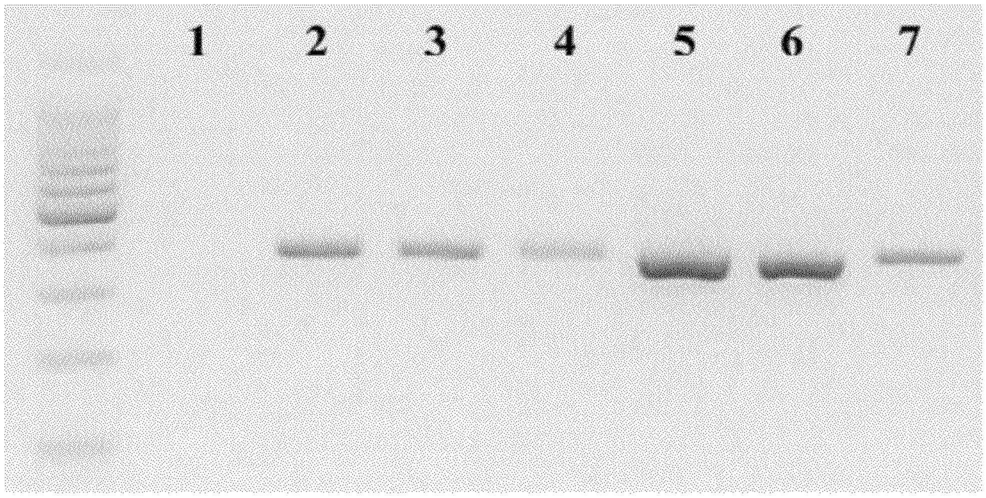

FIG. 37. Results of bench top and on-chip Whatman FTA elution for purification of DNA from *E. coli*. All tests were performed using 1 million (i.e., 1,000K) *E. coli* loadings.

Figure 38:
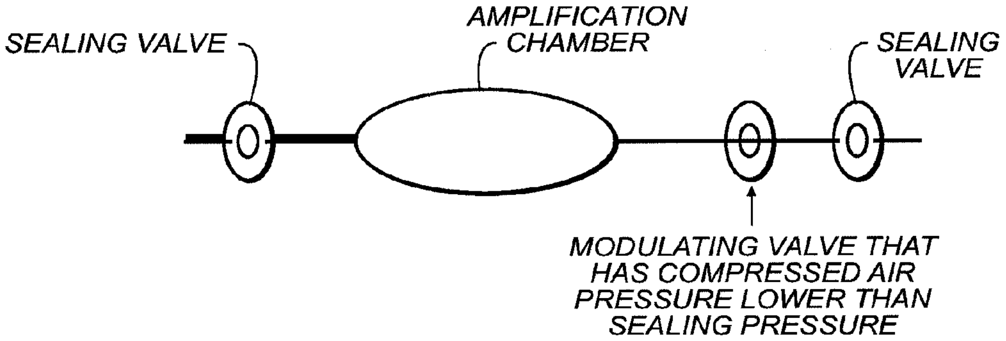

FIG. 38. Schematic diagram of pressure relief device that can be used with a closed nucleic acid amplification reactor in the nucleic acid amplification area of a microfluidic device, e.g., with a PCR reactor.

Figure 39:
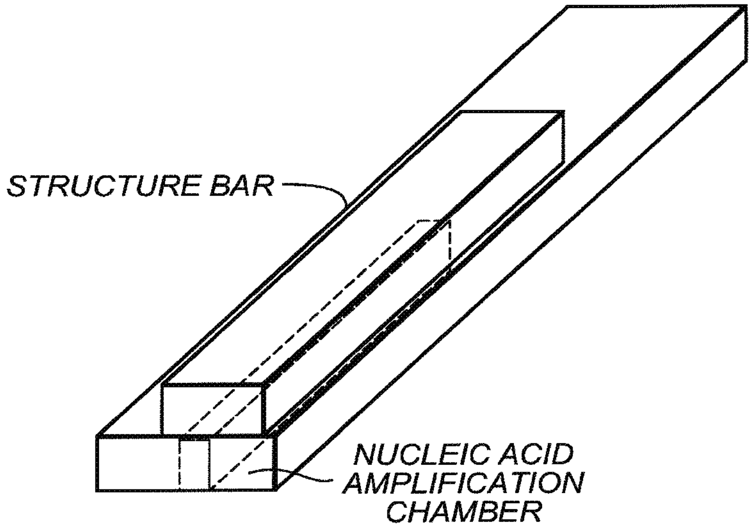

FIG. 39. Schematic diagram of rigid structure that can be bonded on top of a nucleic acid amplification reactor, e.g., a PCR reactor, to prevent the reactor from bowing up as a result of thermal effects at elevated temperatures.

Figure 40:
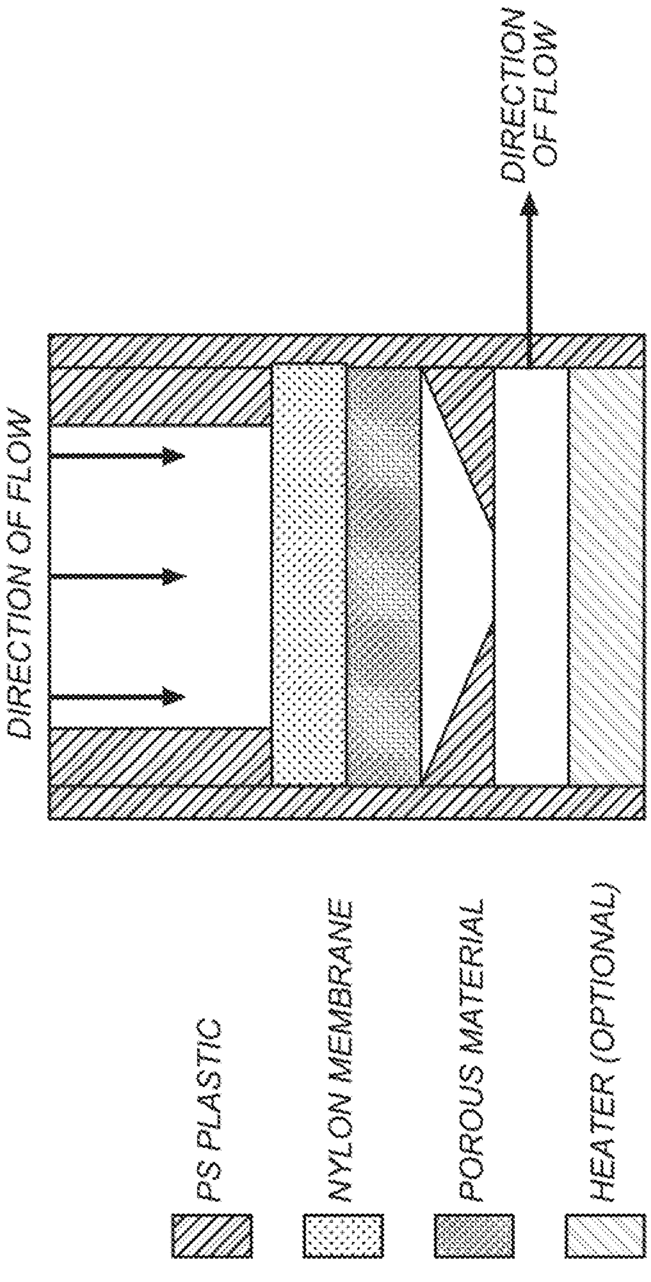
Figure 41:
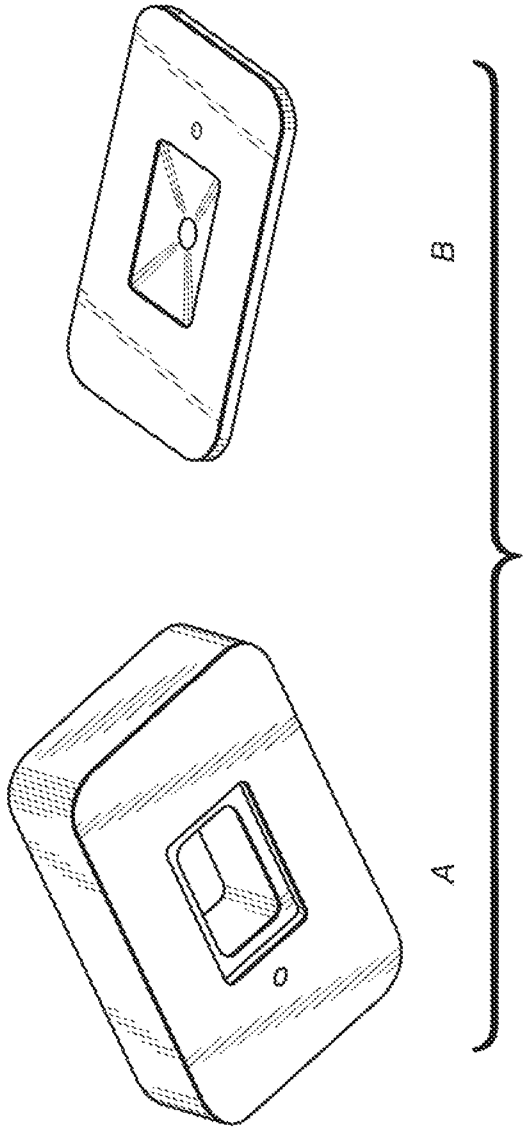

FIGS. 40-41. RDB flow design for arrays of spots in a small area.

FIG. 40. Side view of RDB flow design.

FIGS. 41A-B. Perspective views of an embodiment of an on-chip RDB reservoir (A) and chamfered spacer for RDB reservoir (B).

FIGS. 42-50. Progressive operation of the microfluidic device of FIG. 1.

5. DETAILED DESCRIPTION OF THE INVENTION

The present invention provides a microfluidic device ("chip") and methods based thereon that can combine sample preparation, amplification of a biologically active molecule and can provide a suitable biological sample for analysis and/or detection of a molecule of interest from the originally prepared sample. The small-scale apparatus and methods provided by the invention are easier, faster, less expensive, and equally efficacious compared to larger scale equipment for the preparation and analysis of a biological sample.

The microfluidic device provides the structural and functional capability to automatically process a raw nucleic acid-containing sample and conduct nucleotide (e.g., DNA or RNA) amplification using nucleic acid templates derived from the sample. The device has the advantage of controlling the contamination of reagents, products or samples during processing, as well as low reagent consumption.

Assays conducted on the device are fully automated. The microfluidic device system provided by the invention yields the desired results with virtually no "hands-on" effort other than the introduction of samples or specimens, thereby providing a means to save considerable time and effort on the part of the analyst. Moreover, unskilled individuals can perform sophisticated molecular diagnostics by only having to simply apply the raw sample or specimen to the microfluidic device.

The microfluidic device is suitable for analysis of samples of interest from any biological source such as viruses, bacteria, fungi, prokaryotic cells, eukaryotic cells, archaean cells, etc. which can serve as a potential source for a biological macromolecule of interest, including, but not limited to polynucleotides (e.g., DNA, RNA) proteins, enzymes, or from biological materials such as whole blood, blood serum or plasma, urine, feces, mucous, saliva, vaginal or cheek swabs, cell cultures, cell suspensions, etc. The microfluidic device can be used for a wide variety of detection, diagnostic, monitoring and analytical purposes that involve the detection of biological or biologically derived substances or materials, for example, medical and veterinary diagnostics, food processing, industrial processing, and environmental monitoring. The device can be used as a diagnostic device to detect the presence of an infection, disease or disorder in a biological sample from an individual. Many diseases or disorders are suitable for detection, including, but not limited to β-thalassemia, UTIs (urinary tract infections), STIs (sexually transmitted infections) such as *Neisseria gonorrhoeae, Chlamydia trachomatis*, the causative agent of syphilis, *Treponema pallidum*, bacteria associated with bacterial vaginosis, HPVs such as Herpes simplex virus type 2, papilloma virus, hepatitis B and cytomegalovirus, HIV, yeasts such as *Candida albicans*, and protozoans such as *Trichomonas vaginalis.*

In one embodiment, the microfluidic device for analyzing a sample of interest can comprise a microfluidic device body, wherein the microfluidic device body comprises:

i) a sample preparation area, ii) a nucleic acid amplification area, iii) a nucleic acid analysis area, and iv) a plurality of fluid channels interconnected in a network, and wherein each of the sample preparation area, the nucleic acid amplification area and the nucleic acid analysis area are fluidly interconnected to at least one of the other two areas by at least one of the plurality of fluid channels in the network (FIGS. 1-11).

In another embodiment, the microfluidic device for analyzing a sample of interest can comprise a microfluidic device body, wherein the microfluidic device body comprises:

i) a sample preparation area, ii) a nucleic acid amplification area, and iv) a plurality of fluid channels interconnected in a network, and wherein each of the sample preparation area and the nucleic acid amplification area are fluidly interconnected to the other area by at least one of the fluid channels in the network (FIGS. 1-7).

In another embodiment, the microfluidic device can have two functional areas, a sample preparation area and a nucleic acid amplification area, but can lack an on-chip nucleic acid analysis area (FIGS. 8-16).

For clarity of disclosure, and not by way of limitation, the detailed description of the invention is divided into the subsections set forth below.

5.1 Microfluidic Device Body

The analytic device comprises a microfluidic device body. A microfluidic device body suitable for use according to the invention is described in U.S. patent publications US2006/0076068A1 (Young et al., Apr. 13, 2006), US2007/0166200A1 (Zhou et al., Jul. 19, 2008), and US2007/0166199A1 (Zhou et al., Jul. 19, 2008), which are incorporated herein by reference in their entireties.

The body can comprise a first rigid plastic substrate having upper and lower surfaces, and a substantially rigid plastic membrane, contacting and joined with the upper surface of the first substrate, and having a relaxed state wherein the plastic membrane lies substantially against the upper surface of the first substrate and an actuated state wherein the membrane is moved away from the upper surface of the first substrate. The first rigid plastic substrate can have microfeatures formed therein, and the substantially rigid plastic membrane can be disposed over the microfeature. The membrane has a thickness selected for allowing deformation upon application of appropriate mechanical force. In different embodiments, the membrane can have a thickness of between about 10 μm and about 150 μm, 15 μm and about 75 μm.

The mechanical force is applied by a positive pressure to deform the membrane towards the substrate and can have less than about 50 psi. In one embodiment, the magnitude is between 3 psi and about 25 psi.

The mechanical force that is applied by a negative pressure to deform the membrane away from the substrate can have a magnitude of less than about 14 psi. In one embodiment, the magnitude is between about 3 psi and about 14 psi.

The membrane and the first substrate can be made from substantially the same material or from different materials. Example of materials suitable for use in fabricating the body include thermoplastic materials or linear polymeric materials. In a specific embodiment, the material is polymethyl methacrylate, polystyrene, polycarbonate, or acrylic.

The substantially rigid plastic membrane can have an unbonded region that is not attached to the first substrate. The unbonded region of the membrane can at least partially overlie a first channel and a second channel disjoint from the first channel, both channels being disposed in the first substrate, and in the relaxed state forming a seal between the first and second channels.

The unbonded region of the membrane can also at least partially overlie a valve-seat formed in the first substrate, disconnected from and substantially between the first and second channels.

The valve seat can comprise a ridge substantially perpendicular to a longitudinal axis of the first and second channels.

The unbonded region of the membrane can at least partially overlie a first channel and a second channel disjoint from the first channel, both channels being disposed in the first substrate, and in the actuated state separates from the upper surface of the first substrate to provide a cavity suitable for fluid flow between the first and second channels.

The first substrate can also include a through-hole extending from the upper surface of the first substrate to the lower surface of the first substrate.

The unbonded region of the membrane can be substantially circular, elliptical or rectangular, with rounded corners.

The body can further comprise a second rigid plastic substrate contacting and joined with an upper surface of the membrane.

The first substrate, the second substrate, and the membrane can be made of substantially the same material.

The second substrate can include a chamber lying substantially above the unbonded region of the membrane and sized such that the unbonded region of the membrane can be moved away from the upper surface of the first substrate and remain substantially enclosed by the chamber.

The body can further comprise a pump having a plurality of disconnected unbonded regions, each forming an independently actuatable valve structure and being connected in series by microchannels. The microchannels have varying resistances to fluid flow.

The body can further comprise a supporting structure above the membrane sized, shaped, and positioned to structurally support the membrane when the membrane is in an actuated state.

A stop can be disposed above the membrane that is sized, shaped, and positioned to prevent the membrane from moving beyond a desired distance from the first substrate.

The body can have a plurality of pumps having a shared valve structure. The shared valve structure can include a membrane disposed above three or more microchannels to provide a plurality of fluid ports coupled with the shared valve.

The body comprises at least one reservoir capable of storing one or more of a fluid material, a gaseous material, a solid material that is substantially dissolved in a fluid material, a slurry material, an emulsion material, and a fluid material with particles suspended therein. In specific embodiments, the sample of interest comprises a biological material, e.g., a suspension of cells in a fluid.

The reservoir can be arranged to be substantially vertical. It can be coupled with liquid extraction means for extracting liquid from within the reservoir at or near defined vertical levels. The reservoir can contain a fluid material and particles, and the pump can be coupled to the reservoir so as to circulate fluid through the device in a manner that prevents the particles from settling at either of a top and a bottom of the reservoir. The reservoir can be coupled between a first and a second one of the independently actuatable valve structure.

In another embodiment, the body can comprise a plurality of reservoirs interconnected through a pump mechanism. The pump mechanism can include a shared valve structure for passing fluid from the plurality of reservoirs.

The body can also comprise at least one microfeature. The microfeature can comprise a channel having a geometry for favoring one direction of flow.

The body can comprise a pump having one unbonded region forming an externally actuatable diaphragm structure, interconnected by microchannels to two unbonded regions forming passive valve structures actuatable by fluid flowing through the pump. In another embodiment, the pump can have a plurality of disconnected unbonded regions, each forming an independently actuatable diaphragm structure, with each diaphragm structure partially overlapping at least one other diaphragm structure.

In one embodiment, the body can comprise at least one diaphragm disposed between particular or selected fluid channels for transforming a pressure from the differential pressure source to a desired open or closed position.

In a specific embodiment, the body can comprise a first polystyrene substrate having upper and lower surfaces and microfeatures formed therein, and a polystyrene membrane solvent bonded to the upper surface of the first substrate. The body can have a relaxed state wherein the polystyrene membrane lies substantially against the upper surface of the first substrate and an actuated state wherein the polystyrene membrane is moved away from the upper surface of the first substrate.

The weak solvent bond can be formed by a solvent having little or substantially no bonding effect under room temperature and ambient force conditions, but capable of forming a bonded interface between two mating surfaces under appropriate temperature or force conditions.

In a specific embodiment, the body can comprise a functional fluidic network fabricated in a plurality of layers of weak solvent-bonded polystyrene. For example, a three-layer polystyrene body ("chip") that can be made via the weak solvent lamination process as disclosed in U.S. Patent Application 2006/0078470A1, which is incorporated herein by reference. In a specific embodiment, the chip can be a laminated structure, comprising: a first component having first and second surfaces, wherein at least one of the surfaces includes a microstructure, further wherein the first component is a polymeric material; and a second, polymeric component having first and second surfaces, wherein one of the first and second surface of the second component is fixedly attached to one of the second and first surface of the first component, respectively, by a bonding agent, wherein the bonding agent is a weak solvent with respect to the polymeric components as disclosed U.S. Patent Application 2006/0078470A1.

In one embodiment, the body comprises three areas that can be used to perform an assay of interest (e.g., a nucleic acid detection assay): a sample preparation area, a nucleic acid amplification area and a nucleic acid analysis area. All three areas can be fluidically connected, using methods known in the art, to pumps and valves (see, e.g., U.S. Patent Application 2006/0076068A1, incorporated herein by reference) and to reservoirs and channels (see, e.g., U.S. Patent Application 2007/0166200A1, incorporated herein by reference). The reservoirs and channels can be constructed in the chip by e.g.; the weak solvent bonded process (U.S. Patent Application 2006/0078470A1).

In another embodiment, the device body can have a substantially rigid diaphragm that is actuatable between a relaxed state wherein the diaphragm sits against the surface of a substrate and an actuated state wherein the diaphragm is moved away from the substrate, as disclosed in U.S. Patent Application 2006/0076068A1, incorporated herein by reference. The microfluidic structures formed with this diaphragm can provide easy-to-manufacture and robust systems, as well as readily made components such as valves and pumps.

In one particular embodiment, the device body is a polymeric microfluidic structure in which a substantially rigid plastic membrane is fixedly bonded or laminated to an essentially planar rigid plastic substrate with a weak solvent acting as a bonding agent. In a specific aspect, the substrate includes microfeatures, and the device body includes bond-free segments surrounded and defined by bonded areas between the deformable membrane and the essentially planar substrate surface, resulting in valve structures. In some embodiments, a second substrate is bonded to the upper surface of the membrane and includes a chamber that may be used to apply pneumatic pressure to the unbounded region of the membrane. According to methods consistent with the use of the invention, pneumatic pressure or force is applied to deform the membrane, thus actuating the valve. In some embodiments, a pump comprises a plurality of valve structures interconnected by microchannels. Valves, pumps, reactors and microfluidic reservoirs can be interconnected with microchannels to form circulators, mixers, or other structures with functionality relevant to microfluidic processing and analysis.

In another embodiment, the device body can have a first rigid plastic substrate having upper and lower surfaces, and a substantially rigid plastic membrane, contacting and joined with the upper surface of the first substrate, and having a relaxed state wherein the plastic membrane lies substantially against the upper surface of the first substrate and an actuated state wherein the membrane is moved away from the upper surface of the first substrate. The first rigid plastic substrate may have microfeatures formed in the substrate and the substantially rigid plastic membrane is often disposed over at least one of the microfeatures. The substantially rigid plastic membrane may have a Young's modulus of between about 2 Gpa and about 4 Gpa and have a thickness, or width, selected for allowing deformation upon application of appropriate mechanical force. The membrane may have a thickness of between about 10 μm and about 150 μm, and more specifically between about 15 μm and about 75 μm.

The mechanical pressure to which the membrane will respond may be a positive pressure applied to deform the membrane towards the substrate and may be less than about 50 psi, and may be between 3 psi and about 25 psi. Alternatively, and optionally, the mechanical pressure may be a negative pressure applied to deform the membrane away from the substrate and has a magnitude less than about 14 psi and may have a magnitude of between about 3 psi and about 14 psi.

The membrane and the first substrate can be made from substantially the same material. One of the membrane and the first substrate can be a thermoplastic material, or a linear polymeric material and may be made from one of polymethyl methacrylate, polystyrene, polycarbonate, and acrylic.

The substantially rigid plastic membrane can have an unbonded region being unattached from the first substrate. The unbonded region of the membrane can at least partially overlie a first channel and a second channel disjoint from the first channel, with both channels being disposed in the first substrate. In the relaxed state the membrane can form a seal between the first and second channels. Optionally, the unbonded region of the membrane can at least partially overlie a valve-seat formed in the first substrate, disconnected from and substantially between the first and second channels. The valve seat may include a ridge substantially perpendicular to a longitudinal axis of the first and second channels. Further, the unbonded region of the membrane may at least partially overlie a first channel and a second channel disjoint from the first channel. Both of these channels can be disposed in the first substrate, and in the actuated state the membrane separates from the upper surface of the first substrate to provide a cavity suitable for fluid flow between the first and second channels. Optionally, there may also be a through-hole extending from the upper surface of the first substrate to the lower surface of the first substrate. The unbonded region may have any suitable geometry and the geometry selected will of course depend upon the application at hand. In certain embodiments, the unbonded region may be circular, substantially elliptical, substantially rectangular, with rounded corners, or any geometry appropriate for the application.

In certain embodiments, the device body can include a second rigid plastic substrate contacting and joined with an upper surface of the membrane, and optionally the first substrate, the second substrate, and the membrane are made of substantially a same material, such as polystyrene. The second substrate may include a chamber lying substantially above the unbonded region of the membrane and sized such that the unbonded region of the membrane can be moved away from the upper surface of the first substrate and remain substantially enclosed by the chamber.

The microfluidic device body can additionally comprise a pump that includes a pair or group of disconnected unbonded regions, each forming an independently actuatable valve structure that are connected typically in series by microchannels, or some type of fluid passage. The microchannels may have varying resistances to fluid flow, and to that end may have different sizes, geometries and restrictions. Further optionally, the device can include features, such as channels that have a geometry that favors fluid flow in one particular direction of flow.

In one embodiment, a plurality of pumps may have a shared valve structure, and in particular, the pumps may have a shared valve structure that includes a membrane disposed above three or more microchannels to provide a plurality of fluid ports coupled with the shared valve. Thus, in some embodiments, the pump can comprise any three in-line valve structures. A reservoir can be provided that is capable of storing a fluid material, which may be a liquid, a gas, a solid that is substantially dissolved in a fluid material, a slurry material, an emulsion material, or a fluid material with particles suspended therein. The reservoir may be substantially vertical and can couple with a liquid extraction device for extracting liquid from within the reservoir at or near defined vertical levels. The reservoir may also be arranged to be substantially vertical and contains a fluid and particles. The pump can couple to the reservoir so as to circulate fluid through the device in a manner that prevents the particles from settling at a top or a bottom of the reservoir. The reservoir can couple between a first and a second one of the independently actuatable valve structures and a plurality of reservoirs may be interconnected through the pump. The pump can include or connect to a shared valve structure to allow the pump to pass fluid from the plurality of reservoirs.

In a further embodiment, the device may have a pump having one unbonded region forming an exogenously actuatable diaphragm structure, interconnected by microchannels to two unbonded regions to form passive valve structures that are actuatable by fluid flowing through the pump. In yet another embodiment, the pump may have a plurality of disconnected unbonded regions, each forming an independently actuatable diaphragm structure, with each diaphragm structure partially overlapping at least one other diaphragm structure.

The device may include a stopping mechanism, such as a mechanical stop, disposed above the membrane sized, and shaped and positioned to prevent the membrane from moving beyond a distance from the first substrate.

In another aspect, the body can have a first polystyrene substrate having upper and lower surfaces and microfeatures formed therein, and a polystyrene membrane solvent bonded to the upper surface of the first substrate, and having a relaxed state wherein the polystyrene membrane lies substantially against the upper surface of the first substrate and an actuated state wherein the polystyrene membrane is moved away from the upper surface of the first substrate.

The microfluidic device can also comprise, or be coupled to, a differential pressure delivery source, e.g., one or more mechanical air pumps that supply pressure or vacuum.

In one embodiment, the differential pressure source is capable of exerting a positive pressure or a negative pressure with respect to ambient pressure on a selected area of the microfluidic device body.

The microfluidic device can also comprise, or be coupled to, a differential pressure delivery system, e.g., a controller capable of sequentially activating the valves to operate the valves and pumps formed on the substrate (Zhou et al., U.S. Patent Publication No. 2007/0166199A1). The differential pressure delivery system can comprise a differential pressure source (e.g., one or more air pumps). The differential pressure delivery system can be operably connected to the differential pressure source and to the microfluidic device body.

The differential pressure delivery system allows for mixing materials within the device. For example, a controller can operate a reservoir pump chamber and two other pump chambers, whereby a material may be drawn into the reservoir pump chamber and then partially drawn into respective ones of the two pump chambers and the partially drawn material in one of the two pump chambers may be subsequently returned to the reservoir pump chamber.

The microfluidic device can also comprise a computer and/or computer software for controlling the controller.

5.2 Sample Preparation Area and Sample Preparation Methods

The microfluidic device can comprise a sample preparation area. In one embodiment, the sample preparation area can comprise:

a sample intake reservoir;

a reservoir for a sample preparation reagent; and sample purification media;

wherein the sample intake reservoir, the reservoir for the sample preparation reagent, and the sample purification media are fluidly interconnected (FIG. 1-7).

The sample preparation area can contain, for example, one or more elution or waste reservoirs (FIG. 7). The sample preparation area can also contain one or more reservoirs for cell lysis and/or cell lysis buffers, sample washing and/or washing buffers, sample purification and/or purification media, etc. (FIG. 7).

The sample purification media can be disposed in the sample purification media reservoir. In a specific embodiment, the sample purification media is disposed in the bottom of the sample purification reservoir.

Alternatively, the sample purification media can be disposed in one of the plurality of fluidic channels.

The sample preparation area can comprise a sample inlet for introducing the sample of interest into the sample intake reservoir; wherein the sample inlet is fluidically connected to the sample intake area.

The sample preparation area can also comprise a sample mixing diaphragm fluidically connected to the sample intake reservoir.

The sample preparation area can additionally comprise a sample mixing reservoir, fluidically interconnected to at least one other reservoir on the device body.

In one embodiment, the sample preparation area can comprise a heat source for heat-shocking a biological sample, e.g., a sample of cells or organisms. A live specimen can be exposed to a heat shock to produce, e.g., a particular known species of RNA. Upon later nucleic acid amplification of RNA isolated from the specimen in the microfluidic device, it can be determined whether the original specimen was alive when it was introduced into the microfluidic device by analyzing whether the particular known species of RNA was produced by the heat shock.

In one embodiment, biological material, e.g., cells or tissues, in a sample is lysed in the sample preparation process. In another embodiment, biological material is subjected to extraction. Any biological extraction protocol known in the art can be used with the microfluidic device of the invention including but not limited to chemical, mechanical, electrical, sonic, thermal, etc.

Any nucleic acid extraction and purification media known in the art can be used for isolating a nucleic acid of interest. In one embodiment, a silica membrane can be disposed in a fluidic pathway for isolation of nucleic acids. The porous silica membrane can be fabricated of very fine glass threads with a diameter of less than 1 μm. The nucleic acid recovery yield with such media is closely related to the orientation of the glass threads in the fluidic pathway. To avoid the presence of any shortened fluidic pathway and to ensure the sufficiency of the media for nucleic acid extraction and purification, the size of the membrane can be made substantially greater than the cross-sectional area of the fluidic channel.

In another embodiment, the solid phase extraction method of Boom et al. (U.S. Pat. No. 5,234,809) can be used. Boom et al. discloses a process for isolating nucleic acid from a nucleic acid-containing starting material comprising mixing the starting material, a chaotropic substance and a nucleic acid binding solid phase, separating the solid phase with the nucleic acid bound thereto from the liquid, and washing the solid phase nucleic acid complexes.

Any organic solvent known in the art for washing nucleic acids can be used to wash the nucleic acids absorbed on nucleic acid purification media.

Nucleic acid preparation reagents can be lysing or protease reagents. Lysis of a cell or tissue sample of interest can be performed in one or more reagent reservoirs channels or reactors of the microfluidic device. In one embodiment, on-chip mixing of a cell lysis solution (stored in one reagent reservoir) and its respective viscous or non-viscous reaction reagents (stored in different reservoir(s)), can be effected by continuously delivering the fluid from one reservoir to the other.

Cell lysis can be accomplished by methods known in the art such as fluid manipulation, e.g., gentle mechanical stirring or "fluffing," circulation, chemical lysis or a combination of cell lysis methods.

Magnetic beads may also be used for lysis (see, e.g., Lee J G, Cheong K H, Huh N, Kim S, Choi J W, Ko C: Microchip-based one step DNA extraction and real-time PCR in one chamber for rapid pathogen identification. *Lab Chip* 2006, 6(7):886-895).

Magnetic beads may be used to enhance purification protocols or nucleic acid extraction protocols according to standard methods known in the art. For example, they may be used prior to lysis as a sample preparation reagent, e.g., for preliminary concentration or selection of a particular biological material, cell, tissue, or organism or of a subcomponent thereof.

Cell lysis/homogenization can be achieved on the microfluidic device without the use of laboratory equipment typically needed for these purposes.

For example, the cell lysis solution can be homogenized by pulling the viscous solution stored in a reagent reservoir through a porous disk placed at the bottom of the reagent reservoir by continuously actuating an on-chip pump.

In one embodiment, cell lysis can be accomplished by pulling a solution containing a cell sample back and forth in a narrow channel (e.g., 0.9 mm) on the microfluidic device. Such mechanical lysis can be used to homogenize tissue culture cells.

Cell lysis can also be accomplished by shearing cells.

Other methods well known in the art to accomplish cell lysis include chaotropic denaturization (Boom et al., U.S. Pat. No. 5,234,809), sonication, DC voltage applied across a reservoir or channel (Wang H Y, Bhunia A K, Lu C: A microfluidic flow-through device for high throughput electrical lysis of bacterial cells based on continuous dc voltage. Biosens Bioelectron 2006, 22(5):582-588), microelectromechanical-based piezoelectric microfluidic minisonication (Marentis T C, Kusler B, Yaralioglu G G, Liu S, Haeggstrom E O, Khuri-Yakub B T: Microfluidic sonicator for real-time disruption of eukaryotic cells and bacterial spores for DNA analysis. Ultrasound Med Biol 2005, 31(9):1265-1277) osmotic lysis, lysis by local hydroxide generation, mechanical disruption with nanoscale barbs (Di Carlo D, Jeong K H, Lee L P: Reagentless mechanical cell lysis by nanoscale barbs in microchannels for sample preparation. Lab Chip 2003, 3(4):287-291), freeze-thaw, heat denaturization, lysozyme followed by GuSCN, LIMBS (laser irradiated magnetic bead system; Lee J G, Cheong K H, Huh N, Kim S, Choi J W, Ko C: Microchip-based one step DNA extraction and real-time PCR in one chamber for rapid pathogen identification. Lab Chip 2006, 6(7):886-895), and laser and mechanical vibration applied simultaneously.

In one embodiment, lysis can be performed by continuously actuating an on-chip diaphragm pump beneath a reservoir with the sample and the lysing reagent such that the fluid is drawn into the diaphragm as it is actuated and reinjected into the reservoir while the diaphragm is reversibly actuated.

Many preparation processes for biological samples involve lysis of the sample. Solutions used in the art for lysis are generally viscous solutions, although they can also be non-viscous. During sample preparation, a processed (lysed) biological sample will typically flow through a membrane on which nucleic acids from the lysed sample will bind. Later, several wash buffers, which are usually much lower in viscosity than the lysed biological sample, will be passed through the same membrane.

The sample preparation area can additionally comprise a washing reservoir fluidically interconnected to at least one other reservoir on the device body.

The sample preparation area can additionally comprise a waste reservoir fluidically interconnected to at least one other reservoir on the device body.

The sample preparation area can additionally comprise an elution reservoir fluidically interconnected to at least one other reservoir on the device body.

Nucleic acids can be extracted or purified from the sample using methods known in the art, such as by membrane affinity. In one embodiment, a silica membrane can be used. A lysate of the sample can be pushed, sucked or pulled through the membrane (e.g., using a diaphragm pump downstream of the membrane). Fluid preferably flows in a normal direction (perpendicular) through the silica membrane. In one embodiment, elution buffer can be drawn through the silica membrane to extract the nucleic acids. In another embodiment, methods for extracting nucleic acids known in the art, e.g., those of Boom et al., U.S. Pat. No. 5,234,809 can be used.

Solvent (e.g., ethanol) must usually be removed from the membrane before the nucleic acid is eluted from the silica membrane or other type of nucleic acid purification media. The microfluidic device body can comprise means for air-drying the sample purification media. In one embodiment, the sample preparation area comprises means for air-drying the sample purification media. For example, the device body can be fitted with a port attached to an air pump on the controller. An isolation valve can be provided between the port and the reservoir or chamber of the fluidic network in which the silica membrane is located. While the sample and reagents are being manipulated in the fluidic network to flow over or through the silica membrane, the isolation valve on the chip can be closed to assure that none of the fluids leak into the air pump.

Once the membrane has been properly prepared, the isolation valve can be opened and the vacuum pump activated. This causes an air flow through the membrane, effectively drying it. Alternatively, the membrane can be dried by heating or by heated air flow.

In another embodiment, drying can be modulated by simply pumping or blowing air over or through the membrane using an on-chip pump Molecules of interest, such as nucleic acids, can be removed from the membrane and routed to the nucleic acid amplification area.

The sample preparation area can additionally comprise a reservoir for the nucleic acid extraction membrane fluidically interconnected to other reservoirs in the device. A nucleic acid extraction membrane or filter can be disposed in the reservoir.

The nucleic acid extraction membrane can be disposed, e.g., in the bottom of the reservoir for the nucleic acid extraction membrane.

The microfluidic device can additionally comprise an area for drying (e.g., by blowing, heating or vacuum-drying) the nucleic acid extraction membrane.

All areas of the microfluidic device can comprise reservoirs for storing and dispensing sample processing reagents, which can include, but are not limited to enzymes, elution buffers, washing buffers, waste storage, nucleic acid extraction and purification media, nucleotides, primer sequences, detergents and enzymatic substrates. Reservoirs containing these reagents, as well as the nucleic acid amplification area, can be spatially arranged in different sections of the microfluidic device body and can be fluidically interconnected to each other by a fluidic network.

5.3 Nucleic Acid Amplification Area and Nucleic Acid Amplification Methods

The microfluidic device body comprises a nucleic acid amplification area. The nucleic acid amplification area can comprise:

- a nucleic acid amplification reactor;
- a nucleic acid amplification reagent reservoir; and
- a nucleic acid amplification product reservoir;
- wherein the nucleic acid amplification reactor, the nucleic acid amplification reagent reservoir, and the nucleic acid amplification product reservoir are fluidly interconnected.

The nucleic acid amplification reagents in the reservoirs can be, for example, nucleic acid primers or templates, nucleic acid amplification mixes, nucleic acid amplification enzymes, nucleotides, buffers or other nucleic acid amplification reagents. Such nucleic acid amplification reagents are well known in the art.

The reagent and product reservoirs are connected to the nucleic acid amplification reactor and can have one or more inlets to and from the nucleic acid amplification reactor. The reservoirs can contain valves on the inlet(s) and the exit(s) to effectively seal the nucleic acid reactor during, e.g., thermal cycling. In certain embodiments, the on-chip valves can generate bubbles during pumping cycles. Thus using a set of valves to "push" a nucleic acid amplification reagent into the nucleic acid amplification reservoir can lead to bubbles in the nucleic acid amplification reactor which can be difficult to remove. The closing of the inlet valves and the use of pump at the exit to generate a partial vacuum to fill the nucleic acid amplification chamber (by pulling the reagents instead of pushing them) provides a mechanism to fill the nucleic acid amplification chamber without any bubbles. The nucleic acid amplification reactor can also be filled by simply opening the inlet valve and using the pump at the exit side without first generating a partial vacuum in the reactor to fill the reactor without any bubbles.

Owing to fabrication methods of micro-channels, capillary flow along the corners or edges of a channel can occur. This capillary flow can interfere with the loading of the nucleic acid amplification reactor. By using a dry microfluidic device, fluid preferentially wetting the inner surface of the reactor and trapping air during filling can be avoided.

Bubble formation during nucleic amplification reactions can be a problem in a micro reactor. A tilted nucleic acid amplification chamber can allow the bubbles formed to be collected at one side of the chamber. The hydrophobic properties of polystyrene and nucleic acid amplification reagent mixtures affect the ability of the bubbles to be collected at one end of the nucleic acid amplification chamber. Reagent mixtures can have a variety of surfactants and additives, which aid the movement or formation of bubbles. The surfactants interact with the hydrophobic surfaces of the polystyrene.

In one embodiment, a tilted nucleic acid amplification reactor combined with a modified reservoir can be used to expel all bubbles in the chamber and conduits. This "circulating" method can provide several benefits, which include enhanced mixing (especially reagents of differing densities), reduction of bubbles during filling, ability to remove bubbles after filling, filling the valves with reagent and providing a clear "window" for quantitative PCR (qPCR).

qPCR employs sensitive optical detectors and light sources and therefore a nucleic acid amplification reactor without bubbles that interfere with incoming light is advantageous. In one embodiment, the optical detecting equipment can be located at the lower end of the nucleic acid amplification reactor to ensure that bubbles don't interfere with detection. It has also been observed that filling the valves with liquid helps the valves seal better when compared to valves with no liquid (Air). Circulation pumping can also be done at elevated temperatures to remove any trapped bubbles in the nucleic acid amplification reactor because surface tension of the liquid is inversely related to temperature.

In another embodiment, a wax or oil can be used to seal the nucleic acid amplification reactor. Either coating the chamber during the chip making process or incorporating the oil/wax into the reaction mix (e.g. heat would melt the wax and allow it to form a coating above the reaction when it re-solidifies; alternatively oil would sit on top on the reaction, see, e.g., Current Protocols in Molecular Biology, Unit 15.1, Enzymatic Amplification of DNA by PCR: Standard Procedures and Optimization; Quin Chou, Marion Russell, David E. Birch, Jonathan Raymond and Will Bloch; Prevention of pre-PCR mis-priming and primer dimerization improves low-copy-number amplifications; Nucleic Acids Research, 1992, Vol. 20, No. 7 1717-172)

In another embodiment, nucleic acids extracted in the sample preparation area are conducted (i.e., pushed, pulled, sucked or pumped) to the nucleic acid amplification area. The nucleic acids are mixed in a mixing reservoir with one or more nucleic acid amplification reagents, then the mix is conducted into a nucleic acid amplification reactor where any thermally mediated nucleic acid amplification known in the art can be performed, including but not limited to: polymerase chain reaction (PCR), reverse-transcriptase (RT-) PCR, Rapid Amplification of cDNA Ends (RACE), rolling circle amplification, Nucleic Acid Sequence Based Amplification (NASBA), Transcript Mediated Amplification (TMA), and Ligase Chain Reaction.

In one embodiment, thermal cycling for nucleic acid amplification is performed through the membrane that is used to create the valves and pumps which, given its thinness, does not present a significant thermal barrier while also providing good contact between the heater located on the manifold of the controller and the amplification reactor.

In a specific embodiment, the nucleic acid amplification chamber is a thermal cycling reactor or chamber. The bottom of the thermal cycling chamber can be, for example, a thin layer of polystyrene. The bottom of the thermal cycling chamber can be heated during thermal cycling by a heater that is not disposed on or in (e.g., external to) the microfluidic device body.

In another embodiment, the nucleic acid amplification (e.g., PCR) reactor is fabricated by enclosing a (three-walled) channel structure provided in the substrate of the microfluidic device body with a thin polystyrene film by using a weak solvent bonding or lamination method (US 2006/0078470, incorporated herein by reference in its entirety). The use of weak solvent bonding advantageously enables the use of polystyrene in such an application while preserving the integrity and reliability of the microfeatures disposed therein.

The thin film provides very low thermal resistance thus allowing fast thermal cycles. The film is also flexible, enabling excellent contact with a heater. The chamber is fluidically connected to a single or a plurality of reagent inlet reservoirs and a single or a plurality of outlet reservoirs via on-chip valves and pumps In another embodiment, the nucleic acid amplification reactor is fabricated by laminating a thin polystyrene film, using the weak solvent lamination method to circular, rectangular, square or other aperture shapes formed in the microfluidic device body. The amplification reactor formed between the walled-substrate aperture and a film adjacent the bottom of the aperture allows the amplification reaction to be carried out at elevated temperature under ambient pressure conditions.

The membrane bonded onto the microfluidic device can be used to provide a reactor for nucleotide amplification, e.g., rapid PCR thermocycling. A thin membrane can be provided as the bottom of the nucleic acid amplification reactor to reduce the thermal insulation of the system.

Nucleic acid amplification requires a thermal cycle. This cycle requires the transfer of heat to and from the reagents in the reactor. In some embodiments, the microfluidic device body and nucleic acid amplification are produced from Polystyrene (PS), which has poor thermal conductivity. In order to rapidly change the temperature of the fluid in the reactor, a thin layer of PS material is preferred. During the regular manufacturing of the microfluidic device, a 25 μm thick membrane film is provided sealing the bottom of the thermal cycle reactor.

The microfluidic device can also have a resistive heater assembled onto the device, which when placed on the manifold of the controller contacts electrodes and can power the heater for the thermal cycling.

For nucleic acid amplification, the heater on the manifold of the controller is positioned against this film, providing a low thermal resistance path to heat and cool the reactor.

In another embodiment, a heating element can be disposed beneath the amplification reactor in direct contact with the polystyrene film enclosing the molecular amplification reactor. Alternatively, a thermally conductive material can be disposed between the heater and the film of the reactor bottom. According to the various aspects of the nucleic acid amplification reactor, the reactor can advantageously have a volumetric capacity ranging from a fraction of a microliter to tens of microliters.

In another embodiment, the nucleic acid amplification reactor can be supported with a clamp, assuring contact between the bottom of the chamber and the heater disposed against the film defining the bottom of the chamber. The clamp also acts as a support to the upper wall of the reactor to minimize deformation.

The aforementioned heater may be of various types, such as conventional surface mount electronic resistors, thin film heaters, infrared emitters, radio frequency or other known micro-heaters. In one embodiment, the heater can comprise one or more resistive temperature detectors (RTDs). According to an aspect, two RTDs can be used for heating and one is used for temperature sensing. Alternatively, a single RTD can be used for heating and temperature sensing, thus providing a smaller form factor. The one or more RTDs can be integrated into the chip to form the base of the reactor. The heaters can be controlled via conditional statement control or by other known control techniques. In an advantageous aspect, feedback control is used with the RTD to ensure that the nucleic acid amplification set point temperatures are reached.

In one embodiment, a resistance temperature detector (RTD) can be used as a temperature sensor and a resistive heater to thermocycle the nucleic acid amplification reactor. RTDs are well known in the art and commercially available (e.g., from Omega Engineering Inc., Stamford, Conn.). An RTD is a high precision resistor with a known first derivative relationship between resistance-temperature. Therefore, a change in temperature may be measured by measuring the change in resistance. These sensors are typically made of platinum, either as a wound wire or deposited thin film, with a nominal resistance of 100 Ohms. Since the construction of an RTD is essentially that of a resistor it may be used as such. With appropriate circuitry well known in the art, one may use a single RTD and switch between heating and sensing modes. Alternatively, a combination of RTDs can be used with some operating as dedicated heaters and others as dedicated sensors. These constructions provide a compact heating and temperature sensing solution.

Any nucleic acid amplification protocol known in the art can be used with the microfluidic device of the invention.

Nucleic acid amplification protocols known in the art can be adapted for use with the microfluidic device and methods of the invention, including, but not limited to, polymerase chain reaction (PCR), reverse-transcriptase (RT-) PCR, Rapid Amplification of cDNA Ends (RACE), rolling circle amplification, Nucleic Acid Sequence Based Amplification (NASBA), Transcript Mediated Amplification (TMA), and Ligase Chain Reaction.

Protocols comprising several different reactions can be combined and carried out on the microfluidic device.

For example, an on-chip DNA extraction/PCR protocol can be carried out on the devices shown in FIGS. 8-11 and 12-16, which have two functional areas, a sample preparation area and a nucleic acid amplification area. FIG. 11 shows an exemplary layout (mapping) of the plurality of reagent reservoirs denoted by Cells, Ethanol, Mixer, Waste, Elution, NA1, NA2, AW1, AW2 in the microfluidic device shown in FIG. 10. According to this embodiment, Cells will hold suspended cells and proteinase K; Mixer will hold buffer AL; Ethanol will hold ethanol; AW1 will hold washing buffer AW1; AW2 will hold washing buffer AW2; Elution will hold elution buffer AE; NA1 is nucleic acid reservoir 1; NA2 is nucleic acid reservoir 2; Amplification master mix is the reservoir for the amplification master mix; Amplicon outlet 1 is an amplification outlet reservoir 1; Amplicon outlet 2 is an amplification outlet reservoir 2; Waste is a waste product reservoir. The amplification reactor is also shown, as well as outlets "Amplicon1 outlet" and Amplicon2 outlet" to an off-chip analysis zone. In one embodiment, an on-chip DNA extraction/PCR protocol can be carried out as follows:

1. Add all solutions to their respective reservoirs;
2. Circulate cells between Cells-Mixer several times (e.g., 5 times over 10 min) for cell lysis and mixing with the final pass remaining in the Mixer;
3. Pump ethanol from Ethanol to Mixer;
4. Mix ethanol/cell solution in the Mixer;
5. Pump lysed cell solution through purification media into Waste (according to an exemplary aspect, purification media comprises a silica membrane);
6. Pump washing buffer AW1 through purification media into Waste;
7. Pump washing buffer AW2 through purification media into Waste;
8. Remove alcohol absorbed on purification media (this can be accomplished via a controller-mounted pump drawing air through the purification media);
9. Turn off drying pump;
10. Pump elution buffer AE from Elution through purification media (membrane) into NA1;
11. Pump elution buffer AE from Elution through purification media (membrane) into NA2;
12. Pump amplification reagent from Amplification master mix reservoir into NA2;
13. Pump amplification mixture from NA2 through nucleic acid amplification reactor into Amplicon Outlet 1;
14. thermal cycle the remaining amplification mixture in the nucleic acid amplification reactor;
15. Pump amplified products from the amplification reactor into Amplicon Outlet 2.
16. From Amplicon Outlet 2, the amplified products is pumped to the nucleic acid analysis area for detection.

5.4 Nucleic Acid Analysis Area and Analysis Methods

The microfluidic device can comprise a nucleic acid analysis area. The amplicons which result from the nucleic acid amplification reaction can be detected in the nucleic acid analysis area. Any amplicon detection assay known in the art can be readily adapted to the nucleic acid analysis area. Each of the nucleic acid purification area, the nucleic acid amplification area and the nucleic acid analysis area can be fluidly interconnected to at least one of the other two areas by at least one fluid passage.

In another embodiment, the microfluidic device can comprise a sample preparation area and a nucleic acid amplification area, but lack an on-board nucleic acid analysis area. Instead, the detection of nucleic acids can be performed in an area (or with a detector) separate from the microfluidic device (FIGS. 8-16).

In embodiments of the microfluidic device comprising a nucleic acid analysis area, the nucleic acid analysis area can comprise a reactor (reservoir) or reaction area in which the detection assay is conducted and one or more reservoirs for any of the following: a hybridization buffer, a high stringency wash buffer, a low stringency wash buffer, or a conjugation substrate.

In one embodiment the nucleic acid analysis area comprises an area for detecting an interaction between a nucleic acid of interest and a probe for the nucleic acid of interest.

The invention provides a method for detecting a nucleic acid of interest. In one embodiment, a sample suspected of containing a nucleic acid of interest is obtained. The sample is introduced into the sample preparation area of the microfluidic device and prepared for nucleic acid amplification. The prepared sample is introduced into the nucleic acid amplification reactor and a nucleic acid amplification reaction is run in the nucleic acid amplification area to amplify the nucleic acid of interest is detected. The amplified nucleic acid of interest is then introduced into the nucleic acid analysis area and the amplified nucleic acid of interest. The detecting step can comprise running an end-point detection assay such as detecting an interaction between the amplified nucleic acid of interest and a probe for the nucleic acid of interest, e.g., detecting nucleic acid hybridization using standard methods known in the art.

In one embodiment, the detecting step can comprise visualizing color intensity, fluorescence intensity, electrical signal intensity or chemiluminescence intensity.

In another embodiment, the detecting step can comprise generating an intensity value corresponding to at least one molecule of interest in the sample.

In another embodiment, the intensity value can be selected from the group consisting of color intensity value, fluorescence intensity value and chemiluminescence intensity value, current or voltage.

In another embodiment, generating the color intensity value can comprise analyzing or digitizing an image corresponding to the sample to generate a plurality of pixels; providing a plurality of numerical values for respective ones of the plurality of pixels; and producing numerical values to provide the color intensity value.

In another embodiment, a threshold value can be computed and the color intensity value can be compared to the threshold value to detect the molecule of interest.

In another embodiment, at least one of the color intensity value and the threshold value can be stored in a database. The threshold value can be computed using at least one negative control sample.

Also provided are methods for determining the presence of or the predisposition for a disease or disorder of interest in a subject. In one embodiment, the method can comprise:

a) obtaining a sample from the subject, wherein the sample is suspected of containing a nucleic acid associated with the disease or disorder of interest;

b) detecting the nucleic acid associated with the disease or disorder of interest in the sample, wherein the detecting comprises the steps of:

obtaining a sample suspected of containing the nucleic acid of interest;

providing a microfluidic device of the invention;

introducing the sample into the sample preparation area;

preparing the sample for nucleic acid amplification;

introducing the prepared sample into the nucleic acid amplification area;

performing a nucleic acid amplification reaction in the nucleic acid amplification area to amplify the nucleic acid of interest, introducing the amplified nucleic acid of interest into the nucleic acid analysis area; and detecting the amplified nucleic acid of interest, wherein detecting the amplified nucleic acid of interest is associated with presence of or predisposition for the disease or disorder of interest.

The detecting step comprises determining an amount (or level) of the amplified nucleic acid of interest and wherein the method further comprises comparing the amount (or level) with a preselected amount (or level) of the nucleic acid of interest. In one embodiment, a difference between the amount (or level) with the preselected amount (or level) is indicative of presence or predisposition for the disease or disorder of interest.

Nucleic acid detecting methods that can be performed in the nucleic acid analysis area can include, but are not limited to methods well known in the art such as gel electrophoresis, capillary electrophoresis, visualizing results in situ, electrochemical detection, etc.

In a specific embodiment, the nucleic acid analysis area can comprise a reaction chamber or area for performing a reverse dot-blot assay to detect an amplicon. Such assays are well known in the art. The nucleic acid analysis area can also comprise an area for detecting an interaction in the reverse dot-blot assay, e.g., detecting an interaction on a reverse dot-blot substrate or insert. Alternatively, the substrate or insert can be removed from the microfluidic device and inserted into a separate reader or detector.

In one embodiment, the nucleic acid analysis area can comprise an RDB filter fitted into a reservoir with a frit beneath the filter. The reservoir can be fitted with or without a heater and can have a larger diaphragm for aggressive pumping. Amplicons can be delivered directly from the nucleic acid amplification reactor mixed with the hybridization buffer and pumped through the RDB filter in a direction that is normal to the filter.

A frit can be used to keep the mix passing uniformly through the RDB filter. The conjugate can be later bound to the hybridized amplicon and activated for detection or reading with a commercially available auto reader.

A large diaphragm can be used to “fluff” (i.e., by gentle mechanical agitation) the mix and promote a more rapid rate of nucleic acid hybridization in the nucleic acid analysis area.

Standard bench-top procedures use spotted membranes that are placed into plastic bags and or tubes, which are then placed into a temperature controlled water bath. Some devices have been made to supplement the bench top procedures; these devices have used large metal, plastic, and or glass manifolds with rubber gaskets to provide flow through the membrane. These setups use a solid support with sealing cushions or gaskets. A metal plate with holes has also been used for supporting structure and to allow fluid to pass freely, through the blotting membrane.

The Immunetics MiniSlot® & Miniblotter® System is a commercially available system that uses a “sealing cushion” to sandwich the membrane between parallel micro-channels and a supporting bottom plate. In a specific embodiment, two art-known systems such as the Immunetics system can be used to create two flow directions which are perpendicular to each other, thus creating a grid-like pattern.

The RDB flow design can be designed for arrays of spots in a small area (FIGS. 40-41). A porous solid support can be used below the membrane. The membrane is attached to the reservoir’s perimeter only; this avoids interfering with fluid flow through the membrane while also preventing fluid flow through the perimeter of the membrane. The valves used to pump fluid to/from the RDB reservoir are large and subject to sudden changes in pressure. The large fluid flow is distributed evenly by the chamfered layer and mediated by the porous solid support. The porous solid support not only serves to pass fluid through the membrane slowly, but also distributes the flow through the membrane uniformly (FIG. 40). The membrane is fixed at the perimeter of the reservoir (FIG. 41). The chamfered layer may be replaced by smaller holes, but this alternative requires optimization based on the size and location of the smaller holes. A chamfered through-hole distributes pressure evenly over the membrane and requires little to no optimization. The porous solid support also prevents large deflections in the membrane during pumping and “fluffing.” Fluid flow through the membrane increases hybridization between immobilized oligonucleotides and target DNA in solution. The flow through hybridization process is not diffusion limited and thus hybridization reactions proceed rapidly.

5.5 Additional Components and Layout of the Microfluidic Device

The microfluidic device can additionally comprise a differential pressure delivery system, e.g., a controller, that is located on-board or external to the microfluidic device and that is operatively connected to the microfluidic device or to specific areas on the microfluidic device. In one embodiment, the controller disclosed in US2007/0166199A1 (Zhou et al., Jul. 19, 2008, incorporated herein by reference) can be used. The controller can provide two pressure sources, one positive pressure and the other negative pressure. The positive pressure can be used to seal valves, while the negative pressure is used to open the diaphragms. The arrangement provides that the fluid pressure is never higher in the pump than the valve, preventing leakage of the valve. In one aspect, the solenoid manifold on the controller can contain three pressure vessels. This arrangement prevents “cross talk” between the solenoids and provides that supplied pressure to the valves remains unchanged regardless of the changes in proximate control solenoids.

The controller can comprise, for example, a pneumatic manifold having a plurality of apertures, and a chip manifold having channels disposed therein for routing pneumatic signals from respective ones of the apertures to a plurality of pressure-actuatable membranes (diaphragms) in the microfluidic device ("chip") (see US2007/0166199A1, Zhou et al., Jul. 19, 2008). The channels in the chip drive manifold can route the pneumatic signals in accordance with a configuration of the plurality of pressure-actuatable membranes in the microfluidic chip. The pneumatic signals can be routed to at least one signal line in the microfluidic chip for actuating at least one sensor connected to the signal line. The chip drive manifold can comprise at least one channel or set of channels for routing a pneumatic signal from a single aperture of the pneumatic manifold to a plurality of the pressure-actuatable membranes in the microfluidic chip. The channel(s) routes the pneumatic signal from the aperture to a network of channels branching from the single channel. The network of channels branching from the single channel route the pneumatic signal to respective ones of the plurality of pressure-actuatable membranes.

In other embodiments, the microfluidic device can comprise connection means for vacuum, pressure, electrical, and optical input/output located on the manifold of the controller. Such connection means are well known in the art.

In one embodiment a vented cover plate can be fixedly placed atop the reagent reservoirs to prevent possible environmental contamination.

According to the embodiments described herein, structures and processes enabling automatic sample preparation/purification and amplification are integrated on a single microfluidic device platform. No human input is required.

5.6 Differential Pressure Delivery Source and Pumping Fluids on the Microfluidic Device The microfluidic device can comprise, or be coupled to, a differential pressure delivery source such as a mechanical air pump or set of air pumps.

To overcome the problem of pumping widely different solutions (ie. viscous or non-viscous solutions in one embodiment, pumps can be located "upstream" or "downstream" of a particular microfluidic element such as a silica membrane and either pump can be activated to best pump fluids through such microfluidic element. Each of these can be integrated together on the microfluidic device to provide the varying pressures to pump viscous and non-viscous fluids through the same membrane. A separate air pump can also provide enough air flow to dry the membrane prior to elution of the nucleic acids to the nucleic acid amplification area.

The on-chip pumps can create a two-step pump. In one embodiment, the high viscosity fluid can be pulled through the membrane using a pump downstream of the membrane and the low viscosity fluid can be pushed through the membrane using a different set of pumps upstream of the membrane while the drying process can use a separate air pump to continuously pull air through open valves and through the membrane. The on-chip pumps can also be used to pump the biological sample and wash buffers/reagents to separate locations (e.g., a waste reservoir on the microfluidic device) and the valves can be closed such that the air pump will not draw any samples or reagents while air drying the membrane. This can be an important consideration for biologically sensitive samples.

5.7 On-Chip Mixing of Fluids

The ability to rapidly mix two or more separate fluids is a common feature of fluidic systems. In one embodiment, the microfluidic device can comprise a small nozzle structure fabricated beneath a reservoir that can be used to generate a pulsed jet from the bottom of the reagent reservoir for mixing fluids in the reservoir where the diaphragm below such reservoir draws fluid down and then pushes it back up-through the nozzle. This can be used for "fluffing" the reaction mixture. Such fluffing can be used, e.g., to mix larger volumes and different viscosity solutions within the reagent reservoir.

In one embodiment, fluffing can be achieved by using a large diaphragm below the reservoir on the microfluidic device to provide unique mixing flow pattern by pumping fluid reversibly through the nozzle at the bottom of the reservoir. In one embodiment, a flow scheme created by a nozzle and a reservoir can be used as mixer (FIG. 17). A diaphragm is provided on the device. Attached to that diaphragm is a flow channel and through port. Provided above the through hole is a reservoir. When the diaphragm is actuated, and the reservoir is sufficiently full, a jet of fluid will penetrate up through the fluid contained in the reservoir. When the diaphragm is retracted, fluid is pulled down from the reservoir through the port. Then when the diaphragm is reversed the fluid jet will proceed significantly into the reservoir, but the subsequent back flow will draw fluid from the bottom of the reservoir. This provides an efficient means for mixing.

5.8 Multiple Heater Conditional Synchronization

In order to run multiple microfluidic devices sharing component subsystems using one instrument, multiple heaters can be used. When running multiple microfluidic devices all sharing component subsystems it is desirable that all devices finish cycling at the same time. In order to do this the thermal cycling must be synchronized. In one embodiment, this can be achieved using conditional logic statements in the control software, comparing the temperature set point with a temperature measurement from a sensor.

Each heater can be set to a specific temperature that may or may not be the same as other heaters. The user can then easily create a conditional statement that will cause the control software to run a loop until the desired conditions are met. This loop can contain a simple time delay, or other commands to run while the heater temperature moves toward the set point. Once the condition is met, the program continues and runs the next command.

5.9 Convective Heat Transfer to the Microfluidic device

In certain embodiments of the microfluidic system of the invention, the device is removable and disposable. In these embodiments, a heating system can be used in which the heating element is not directly contacting the device. This simplifies the device/manifold interface. If the heating element is removed from the device, the heat must still be transferred to the area where it is needed. By using forced convection, heat can be transferred from an off-chip heater to a given area of the device through machined channels or tubes. The design constraints for both the heater and the interface are simplified.

A fluid can be heated by placing a resistive element inside a tube and flowing fluid through that tube. A temperature sensing element is placed in the fluid steam to measure the temperature and feed this value back to a control system. The heated fluid can then be routed through channels and ports to the area of the device that requires heating.

5.10 Induction Heating

In another embodiment of the invention, an induction heater can be used for heating operations on the device (e.g., PCR thermocycling or RDB). A key benefit of an induction heater in this application is the localization of heating, efficiency of heat transfer and the lack of any direct connection to the microfluidic device (i.e., no electrical contacts to the microfluidic device are required).

5.11 Pneumatic Cooling

During NA amplification reactions, the heater used for thermocycling must cool down rapidly. Cooling can be achieved by any convective or pneumatic cooling element known in the art. For example, a tube from the output from a small air pump can be used to cool the heater. Pneumatic cooling works at room temperature, 25° C., since operating PCR temperatures are between 50-100° C. The larger the temperature difference between the heating element and the air in contact with the heater, the faster it cools. The effect can be increased by coupling a heat sink or a thermal electric cooler to the system.

5.12 Nucleic Acids

In certain embodiments, the invention provides a method of amplifying and/or isolating nucleic acid molecules of interest (also referred to herein as "nucleic acids of interest," "target nucleic acids," "target polynucleotides"). An isolated nucleic acid molecule (or "isolated nucleic acid") is a nucleic acid molecule (or "nucleic acid") that is separated from other nucleic acid molecules that are present in the natural source of the nucleic acid molecule. Preferably, an "isolated" nucleic acid is free of nucleic acid sequences (e.g., protein encoding sequences) that naturally flank the nucleic acid (i.e., sequences located at the 5' and 3' ends of the nucleic acid) in the genomic DNA of the organism from which the nucleic acid is derived. In other embodiments, the isolated nucleic acid is free of intron sequences.

"Nucleic acids of interest," "target nucleic acids" or "target polynucleotides" refer to molecules of a particular polynucleotide sequence of interest. Such nucleic acids of interest that may be analyzed by the methods of the present invention include, but are not limited to DNA molecules such as genomic DNA molecules, cDNA molecules and fragments thereof, including oligonucleotides, expressed sequence tags ("ESTs"), sequence tag sites ("STSs"), etc. Nucleic acids of interest that may be analyzed by the methods of the invention also include RNA molecules such as, but by no means limited to messenger RNA (mRNA) molecules, ribosomal RNA (rRNA) molecules, cRNA (i.e., RNA molecules prepared from cDNA molecules that are transcribed in vivo) and fragments thereof. In various embodiments, the isolated nucleic acid molecule can contain less than about 5 kb, 4 kb, 3 kb, 2 kb, 1 kb, 0.5 kb or 0.1 kb of nucleotide sequences that naturally flank the nucleic acid molecule in genomic DNA of the cell from which the nucleic acid is derived. Moreover, an isolated nucleic acid molecule, such as a cDNA molecule, can be substantially free of other cellular material, of culture medium when produced by recombinant techniques, or of chemical precursors or other chemicals when chemically synthesized.

The nucleic acids of interest can be DNA or RNA or chimeric mixtures or derivatives or modified versions thereof. The nucleic acid can be modified at the base moiety, sugar moiety, or phosphate backbone, and may include other appending groups or labels.

For example, in some embodiments the nucleic acid can comprise at least one modified base moiety which is selected from the group including but not limited to 5-fluorouracil, 5-bromouracil, 5-chlorouracil, 5-iodouracil, hypoxanthine, xanthine, 4 acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the nucleic acid can comprise at least one modified sugar moiety selected from the group including but not limited to arabinose, 2-fluoroarabinose, xylulose, and hexose.

In yet another embodiment, the nucleic acid can comprise at least one modified phosphate backbone selected from the group including but not limited to a phosphorothioate, a phosphorodithioate, a phosphoramidothioate, a phosphoramidate, a phosphordiamidate, a methylphosphonate, an alkyl phosphotriester, and a formacetal or analog thereof.

Nucleic acids for use as primers, probes, or templates may be obtained commercially or derived by standard methods known in the art, e.g., by use of an automated DNA synthesizer (such as those commercially available from Biosearch Technologies, Inc., Novato, Calif.; Applied Biosystems, Foster City, Calif., etc.) and standard phosphoramidite chemistry; or by cleavage of a larger nucleic acid fragment using non-specific nucleic acid cleaving chemicals or enzymes or site-specific restriction endonucleases.

If the sequence of a nucleic acid of interest from one species is known and the counterpart gene from another species is desired, it is routine in the art to design probes based upon the known sequence. The probes hybridize to nucleic acids from the species from which the sequence is desired, for example, hybridization to nucleic acids from genomic or DNA libraries from the species of interest.

In one embodiment, a nucleic acid molecule is used as a probe that is complementary to, or hybridizable under moderately stringent conditions to, an amplified, isolated nucleic acid of interest.

In another embodiment, a nucleic acid molecule is used as a probe that hybridizes under moderately stringent conditions to, and is at least 95% complementary to, an amplified nucleic acid of interest.

In another embodiment, a nucleic acid molecule is used as a probe that is at least 45% (or 55%, 65%, 75%, 85%, 95%, 98%, or 99%) identical to a nucleotide sequence of interest or a complement thereof.

In another embodiment, a nucleic acid molecule is used as a probe that comprises a fragment of at least 25 (50, 75, 100, 125, 150, 175, 200, 225, 250, 275, 300, 325, 350, 375, 400, 425, 450, 500, 550, 600, 650, 700, 800, 900, 1000, 1200, 1400, 1600, 1800, 2000, 2400, 2600, 2800, 3000, 3200, 3400, 3600, 3800, or 4000) nucleotides of a nucleic acid of interest or a complement thereof.

In another embodiment, a nucleic acid molecule is used as a probe that hybridizes under moderately stringent conditions to an amplified nucleic acid molecule having a nucleotide sequence of interest, or a complement thereof. In other embodiments, a nucleic acid molecule is used as a probe that can be at least 25, 50, 75, 100, 125, 150, 175, 200, 225, 250, 275, 300, 325, 350, 375, 400, 425, 450, 500, 550, 600, 650, 700, 800, 900, 1000, 1200, 1400, 1600, 1800, 2000, 2200, 2400, 2600, 2800, 3000, 3200, 3400, 3600, 3800, or 4000 nucleotides in length and hybridize under moderately stringent conditions to an amplified nucleic acid molecule of interest or a complement thereof.

Nucleic acids that can be used as probes (or templates) for detecting an amplified nucleic acid of interest can be obtained by any method known in the art, e.g., from a plasmid, by polymerase chain reaction (PCR) using synthetic primers hybridizable to the 3' and 5' ends of the nucleotide sequence of interest and/or by cloning from a cDNA or genomic library using an oligonucleotide probe specific for the nucleotide sequence. Genomic clones can be identified by probing a genomic DNA library under appropriate hybridization conditions, e.g., high stringency conditions, low stringency conditions or moderate stringency conditions, depending on the relatedness of the probe to the genomic DNA being probed. For example, if the probe for the nucleotide sequence of interest and the genomic DNA are from the same species, then high stringency hybridization conditions may be used; however, if the probe and the genomic DNA are from different species, then low stringency hybridization conditions may be used. High, low and moderate stringency conditions are all well known in the art.

Amplified nucleic acids of interest can be detectably labeled using standard methods known in the art.

The detectable label can be a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include, $^{32}P$, $^{35}S$, $^{14}C$, $^{15}N$ and $^{125}I$, to name a few. Fluorescent molecules suitable for the present invention include, but are not limited to, fluorescein and its derivatives, rhodamine and its derivatives, texas red, 5'-carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'-carboxy-X-rhodamine ("ROX"), HEX, TET, IRD40 and IRD41. Fluorescent molecules that are suitable for the invention further include: cyamine dyes, including but not limited to Cy2, Cy3, Cy3.5, Cy5, Cy5.5, Cy7 and Fluor X; BODIPY dyes, including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes known to those skilled in the art. Electron rich indicator molecules suitable for the present invention include, but are not limited to, aferritin, hemocyanin, and colloidal gold. Alternatively, an amplified nucleic acid of interest (target polynucleotide) may be labeled by specifically complexing a first group to it. A second group, covalently linked to an indicator molecule and which has an affinity for the first group, can be used to indirectly detect the target polynucleotide. In such an embodiment, compounds suitable for use as a first group include, but are not limited to, biotin and iminobiotin.

The nucleic acids of interest that are amplified and analyzed (e.g., detected) by the methods of the invention can be contacted to a probe or to a plurality of probes under conditions such that polynucleotide molecules having sequences complementary to the probe hybridize thereto. As used herein, a "probe" refers to polynucleotide molecules of a particular sequence to which nucleic acid molecules of interest having a particular sequence (generally a sequence complementary to the probe sequence) are capable of hybridizing so that hybridization of the target polynucleotide molecules to the probe can be detected. The polynucleotide sequences of the probes may be, e.g., DNA sequences, RNA sequences or sequences of a copolymer of DNA and RNA. For example, the polynucleotide sequences of the probes may be full or partial sequences of genomic DNA, cDNA, mRNA or cRNA sequences extracted from cells. The polynucleotide sequences of the probes may also be synthesized, e.g., by oligonucleotide synthesis techniques known to those skilled in the art. The probe sequences can also be synthesized enzymatically in vivo, enzymatically in vitro (e.g., by PCR) or non-enzymatically in vitro.

Preferably, the probes used in the methods of the present invention are immobilized to a solid support or surface such that polynucleotide sequences that are not hybridized or bound to the probe or probes may be washed off and removed without removing the probe or probes and any polynucleotide sequence bound or hybridized thereto. Methods of immobilizing probes to solid supports or surfaces are well known in the art. In one particular embodiment, the probes will comprise an array of distinct polynucleotide sequences bound to a solid (or semi-solid) support or surface such as a glass surface or a nylon or nitrocellulose membrane. Most preferably, the array is an addressable array wherein each different probe is located at a specific known location on the support or surface such that the identity of a particular probe can be determined from its location on the support or surface. In a specific embodiment, the method described in Section 6.10 can be used to immobilize nucleic acid probes to a solid support or surface.

Although the probes used in the invention can comprise any type of polynucleotide, in preferred embodiments the probes comprise oligonucleotide sequences (i.e., polynucleotide sequences that are between about 4 and about 200 bases in length, and are more preferably between about 15 and about 150 bases in length). In one embodiment, shorter oligonucleotide sequences are used that are between about 4 and about 40 bases in length, and are more preferably between about 15 and about 30 bases in length. However, a more preferred embodiment of the invention uses longer oligonucleotide probes that are between about 40 and about 80 bases in length, with oligonucleotide sequences between about 50 and about 70 bases in length (e.g., oligonucleotide sequences of about 60 bases in length) being particularly preferred.

5.13 Kits

In an additional aspect, the invention provides a kit that can comprise, in one or more containers, a microfluidic device of the invention with one or more of the following: a controller, visualization or detection apparatus, one or more nucleic acid primers, sample preparation, nucleic acid amplification and/or nucleic acid detection or analysis reagents, buffers, and washing agents, or instructions for using the device. The reagents in containers can be in any form, e.g., lyophilized, or in solution (e.g., a distilled water or buffered solution), etc. The kit can be used, according to the methods of the invention, for the detection or measurement of a molecule of interest. The kit can also be used for production or synthesis of a molecule of interest.

A controller can also be supplied as part of the kit or as an adjunct to the kit. The controller is typically purchased once (upfront) by the consumer for use with one or more kits that are purchased on a per-assay basis.

The following examples are offered by way of illustration and not by way of limitation.

6. EXAMPLES

6.1 Example 1

Microfluidic Device Embodiment with Three Functional Areas

This example describes an embodiment of the microfluidic device ("chip") that has three functional areas, a sample preparation area, a nucleic acid amplification area and a nucleic acid analysis area is an area for carrying out amplification product assays (FIGS. 1-7) and an exemplary method for using the device.

Figure 2:
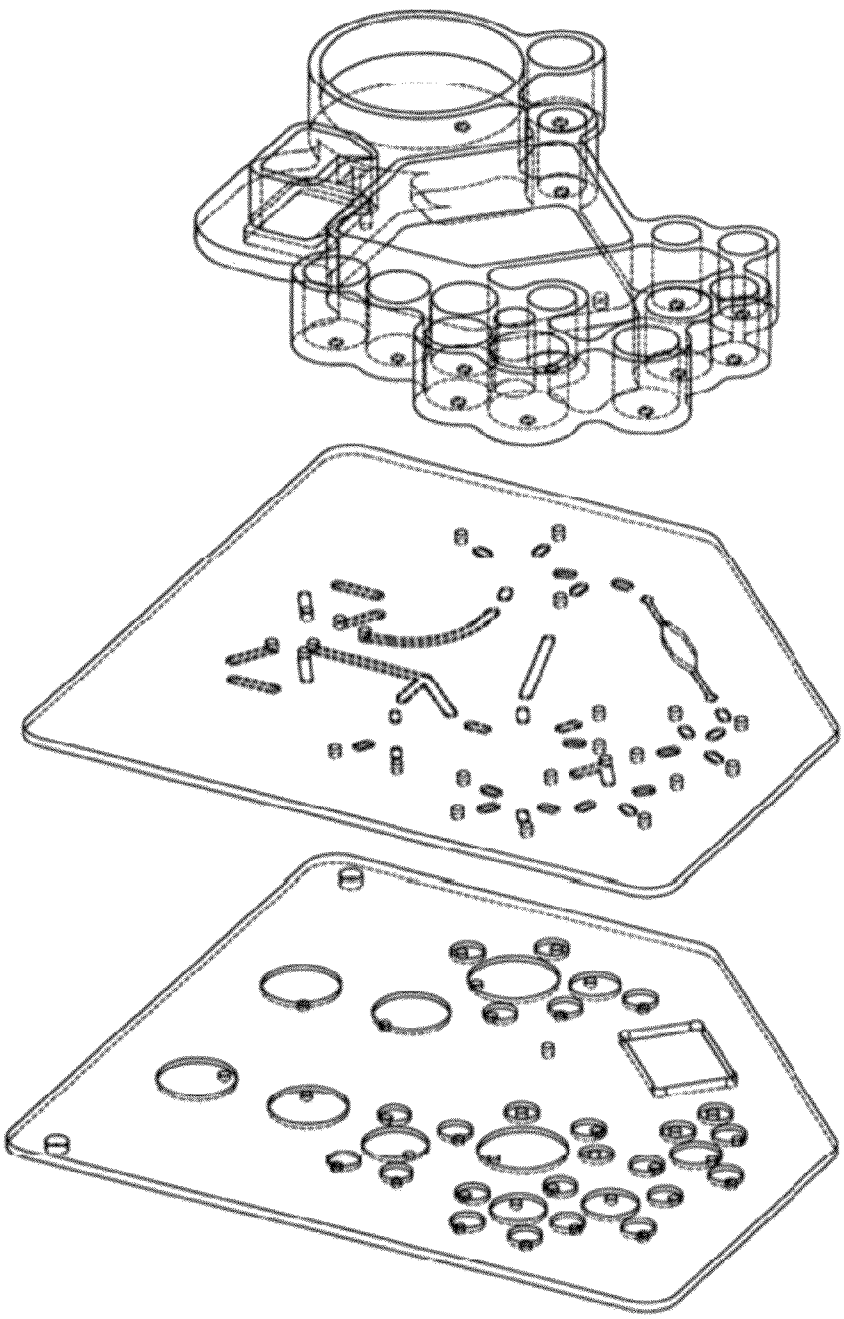

FIG. 2 is an isometric exploded view of the embodiment of the microfluidic device in FIG. 1, showing the valve map.

Figure 3A:
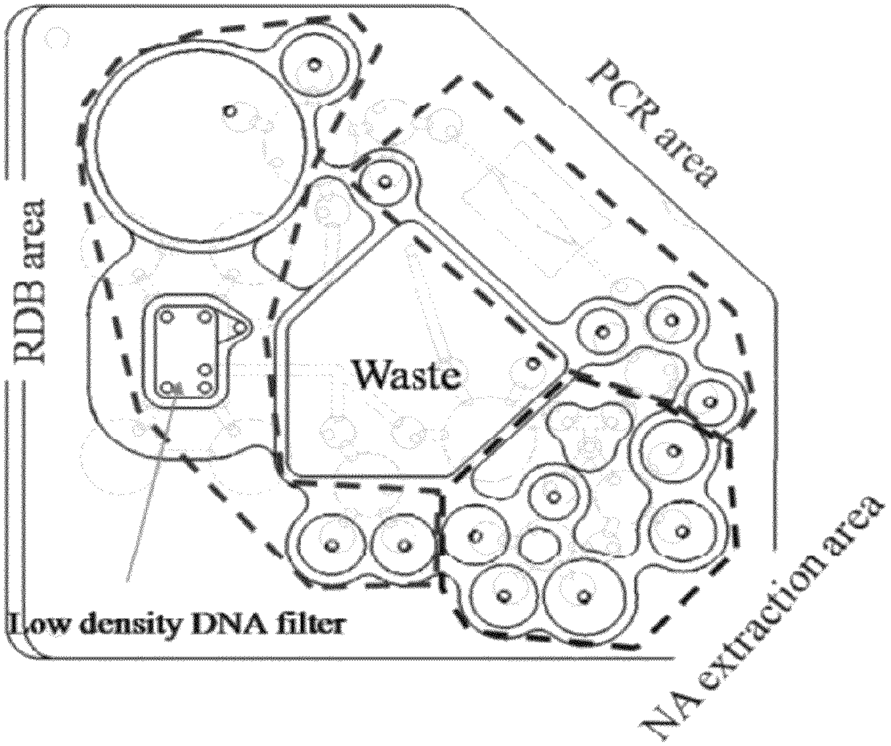
Figure 42:
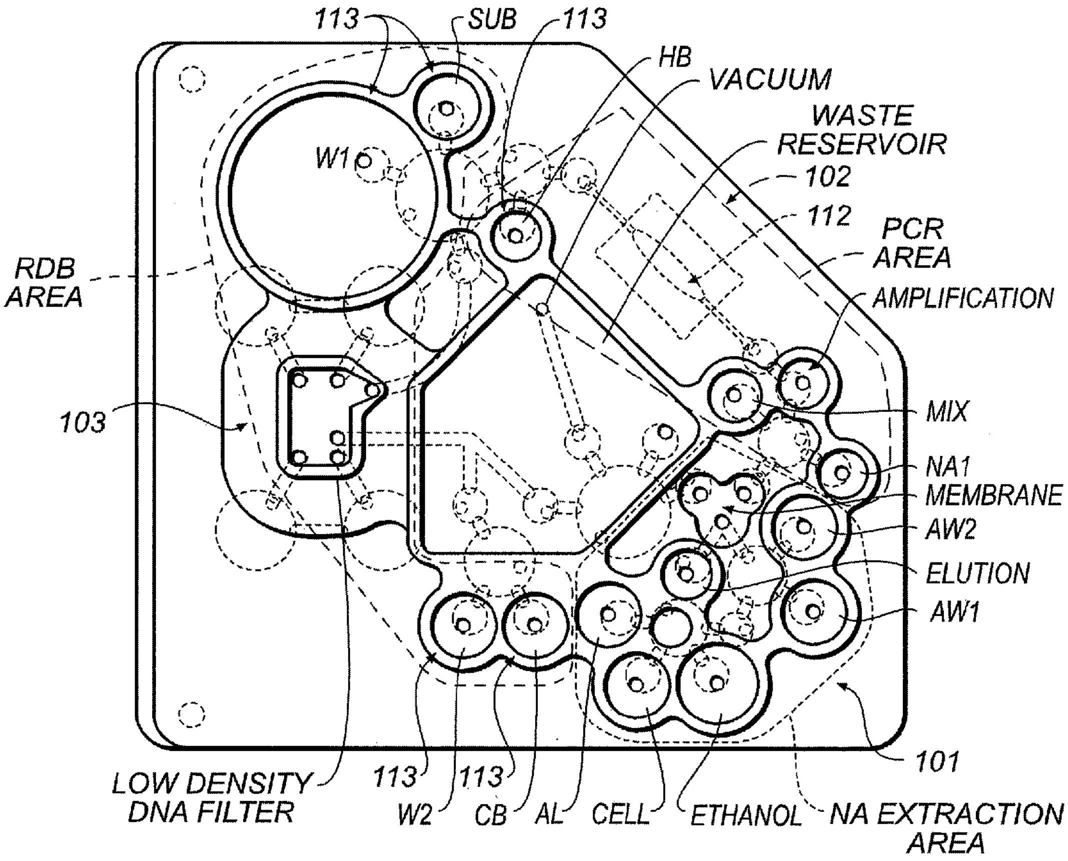
Figure 43:
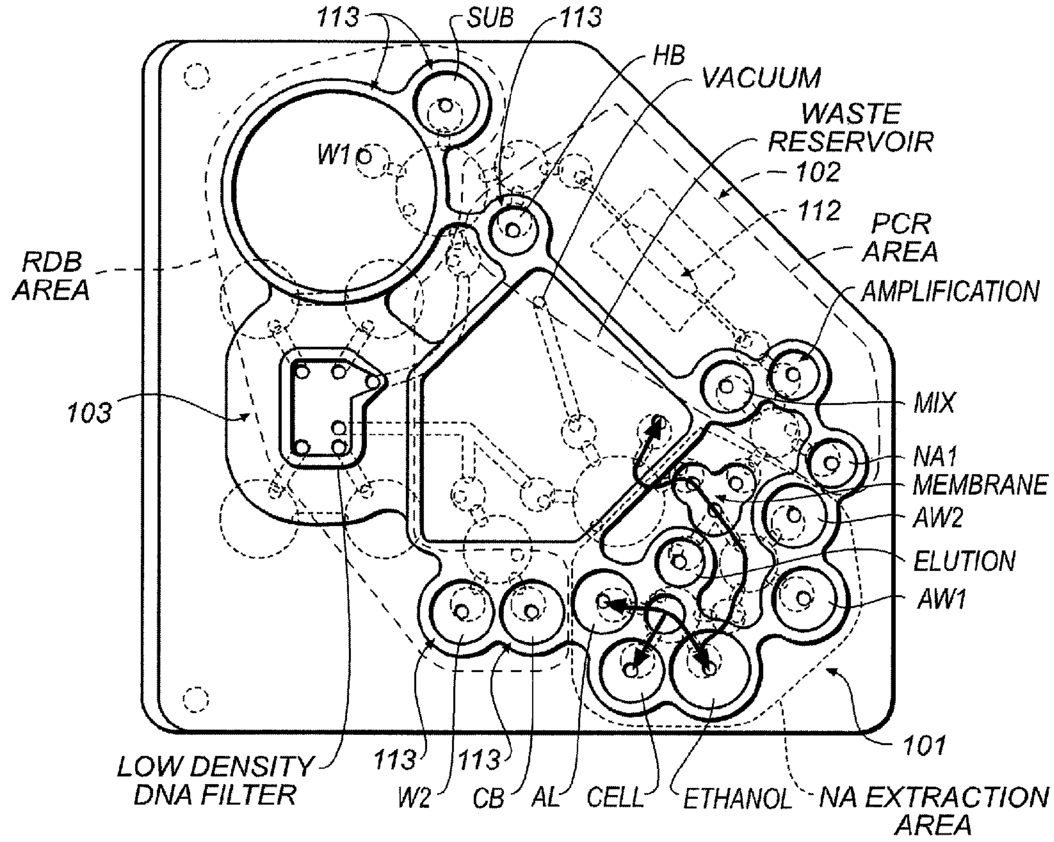

FIGS. 3A and 42 show a top view of the embodiment of the microfluidic device in FIG. 1, showing the sample preparation area ("nucleic acid (NA) extraction area"), the nucleic acid amplification area (in this embodiment, a "PCR area") and the nucleic acid analysis area ("RDB area"). Also shown is the layout of valves, microfluidic channels, through-holes, and a low density DNA filter on the device. In this embodiment, a reverse dot blot (RDB) end-point detection assay can be performed in the nucleic acid analysis area. Waste; waste reservoir.

Figure 3B:
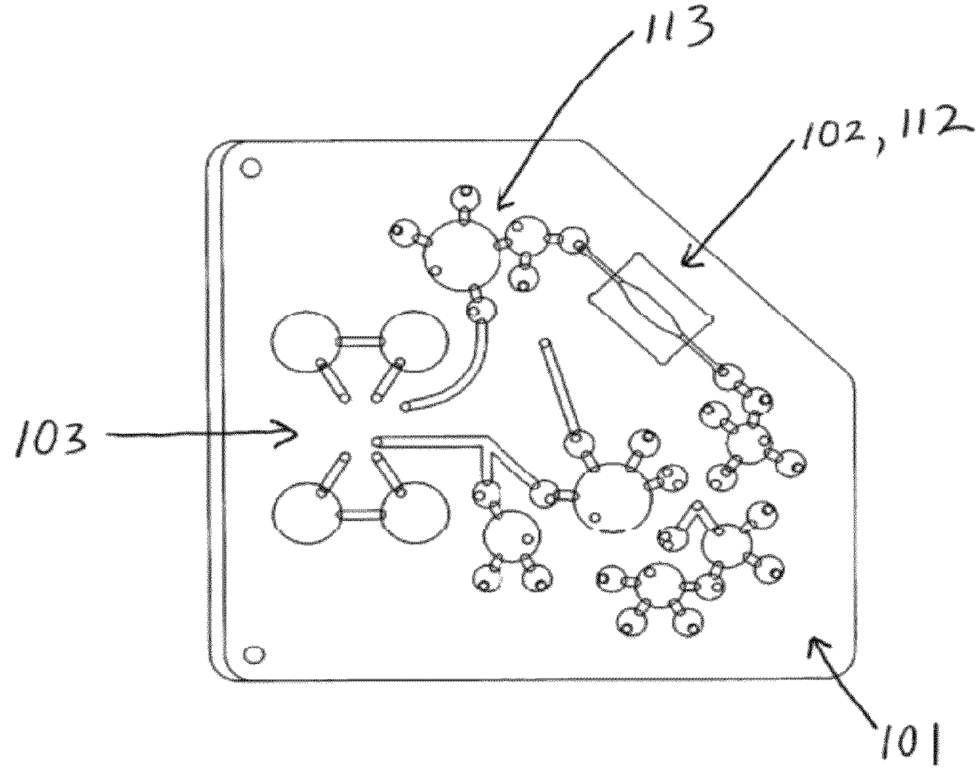

FIGS. 3B and 42 show a top view of the embodiment of the microfluidic device in FIG. 1, showing the sample preparation area 101, the nucleic acid amplification area 102 (comprising a nucleic acid amplification reactor 112) and the nucleic acid analysis area 103, and the layout of valves, microfluidic channels and through-holes on the device. Reservoirs for analysis area 113.

Figure 4:
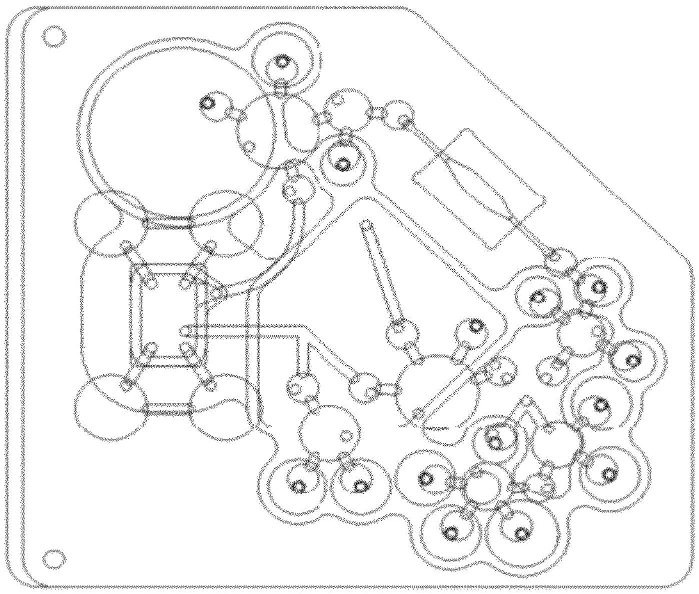
FIG. 4 is a top view of the embodiment of the microfluidic device in FIG. 1, showing the functional layout of the device, including reservoirs, nucleic acid amplification reactor (or chamber), valves, microfluidic channels and through-holes on particular layers of the device.

FIGS. 4 and 42 show a functional map of the embodiment of the microfluidic device in FIG. 1, showing the functions and reservoirs (e.g., reagents) associated with various reservoirs. W1, Wash Buffer 1. W2, Wash Buffer 2. HB, Hybridization Buffer. CB, Conjugation Buffer. Sub, Substrate Buffer.

Figure 5:
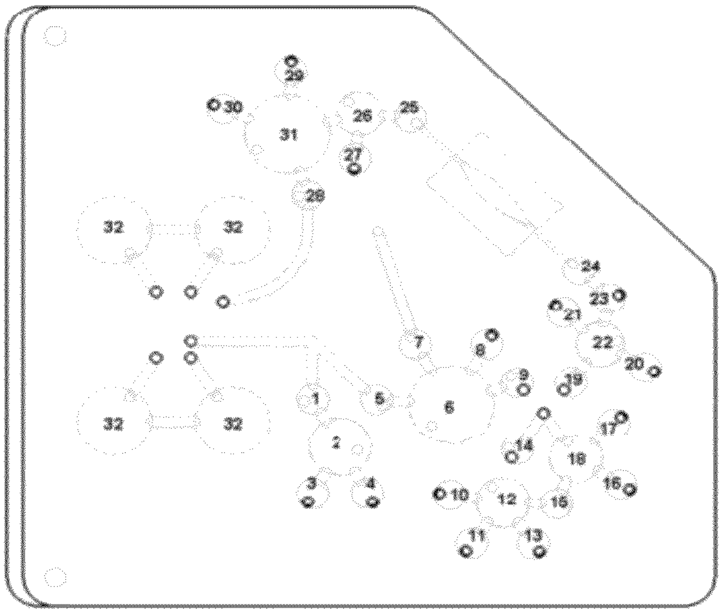
FIG. 5 is a top view of the embodiment of the microfluidic device in FIG. 1, showing a map of the valves on the device.

FIGS. 5-7 and 43-50 are diagrams that show the progressive operation of the microfluidic device of FIG. 1. Dotted lines indicate the flow of a sample as it is processed through the device. In FIG. 5, cells are mixed with buffer AL and Proteinase K for 5-10 minutes at room temperature by pumping back and forth from R1 to R2 several times The contents of R2 is mixed with ethanol by pumping back and forth from R2 to R3 several times. The mixed sample is transferred from R3 through the nucleic acid extraction media and to the waste reservoir via pumping. AW1 and AW2 is transferred through the nucleic acid extraction media and to the waste reservoir via pumping. The nucleic acid extraction media is dried by turning the air pump on for 5-10 minutes and blowing or drawing air through the nucleic acid extraction media.

Figure 6:
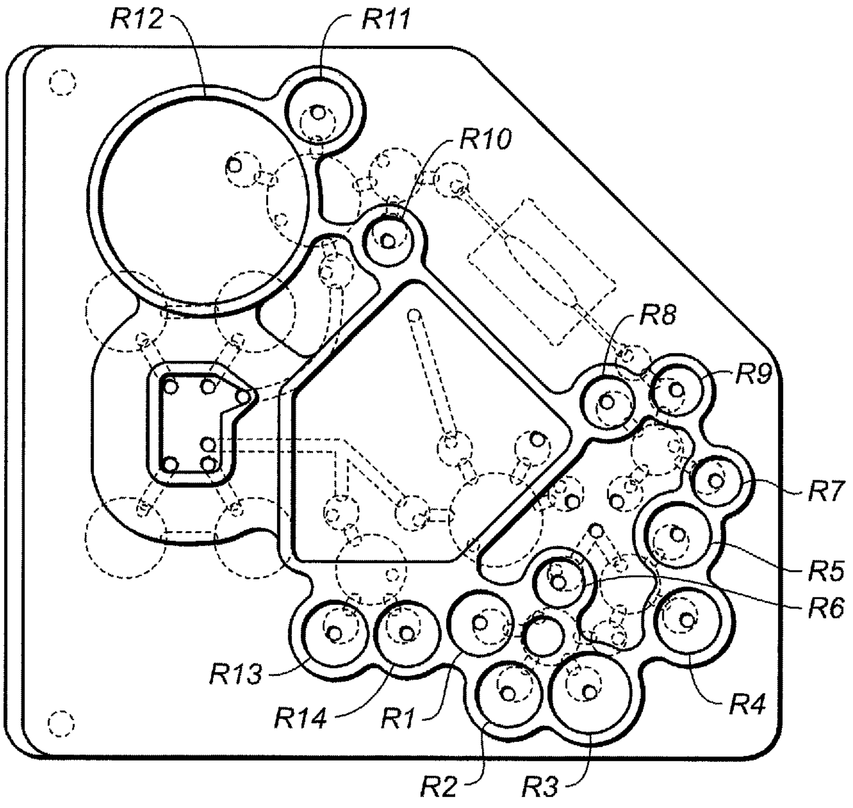
FIG. 6 is a top view of the embodiment of the microfluidic device in FIG. 1, showing a map of the reservoirs on the device.
Figure 44:
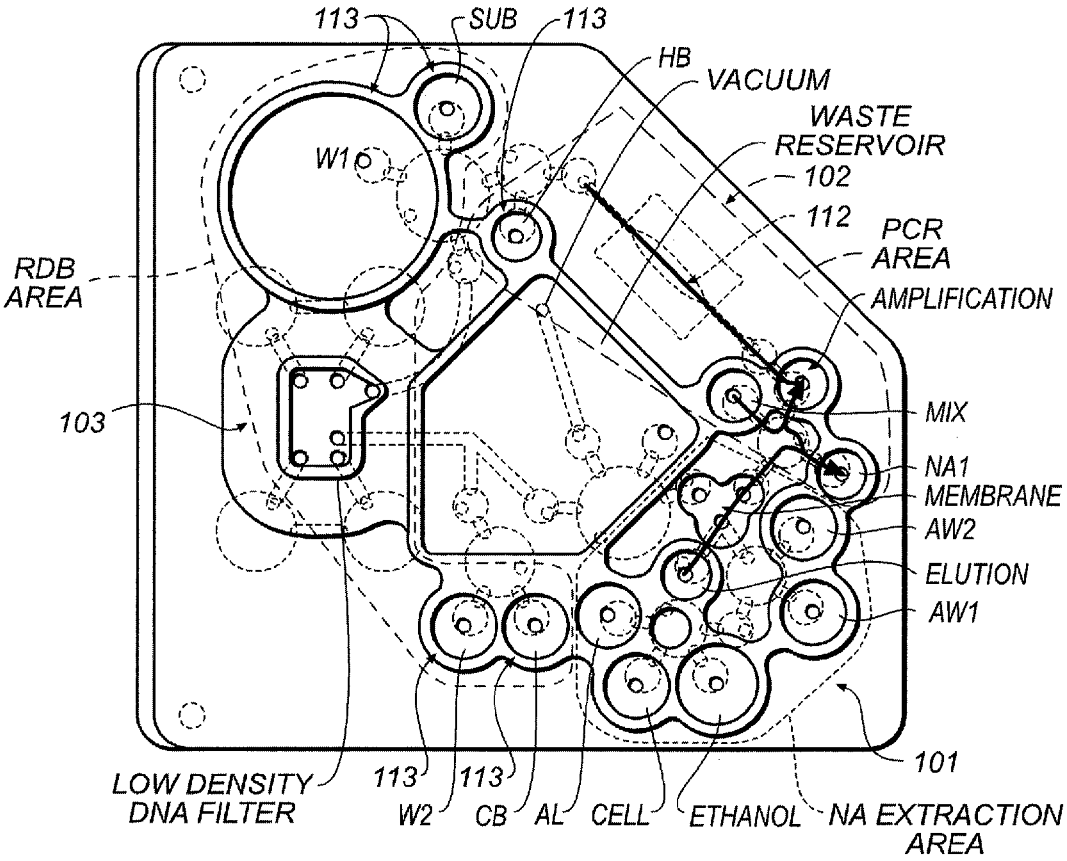

In FIGS. 6 and 44, nucleic acids (e.g., DNA or RNA) are eluted to reservoir NA1 by pumping elution buffer through the nucleic acid extraction media to reservoir NA1. Amplification mix is mixed with eluted nucleic acids by pumping alternately from R8 and R7 to R9. Amplification mix is pumped with the nucleic acids into the thermal cycle reactor, where a nucleic acid amplification reaction is performed.

Figure 45:
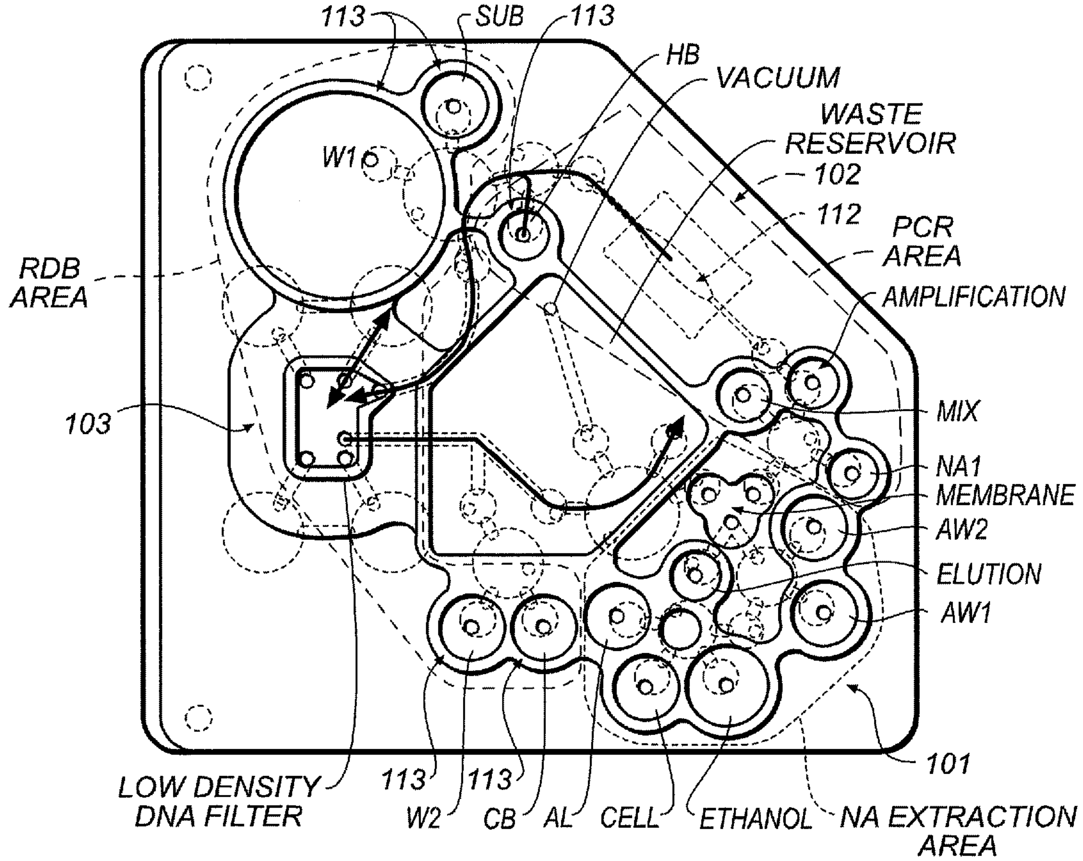
Figure 46:
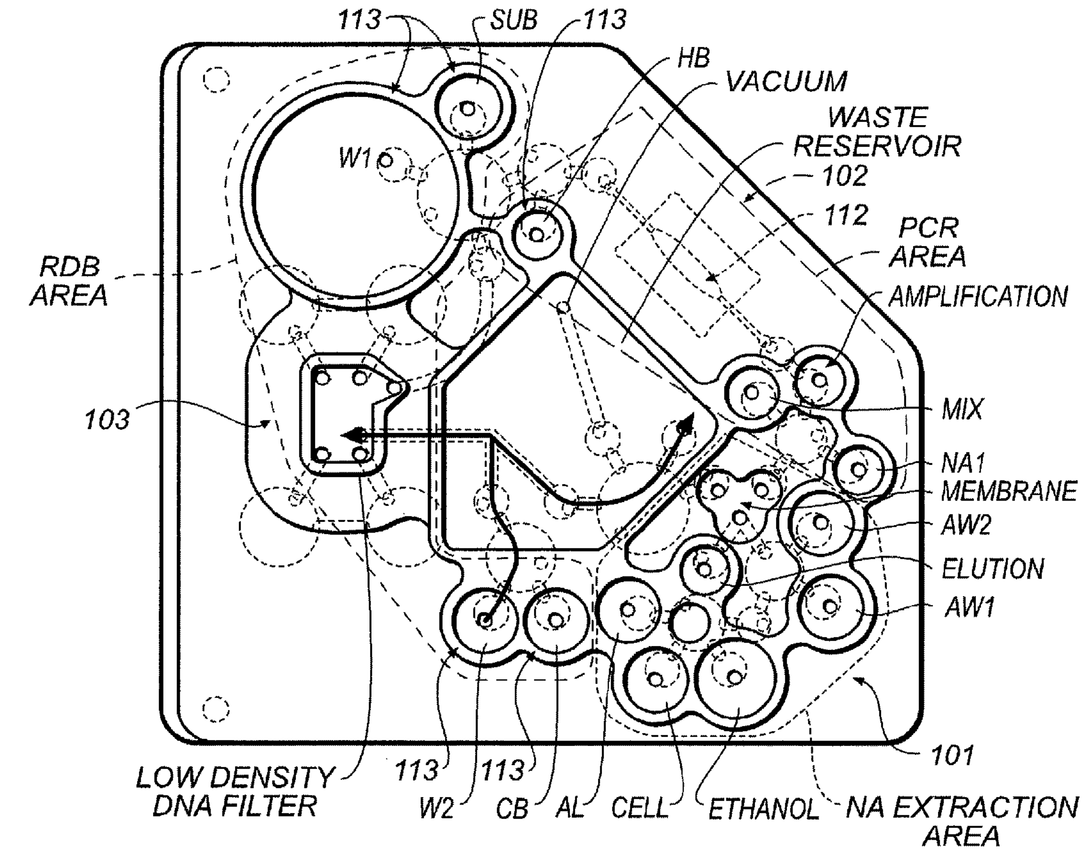
Figure 47:
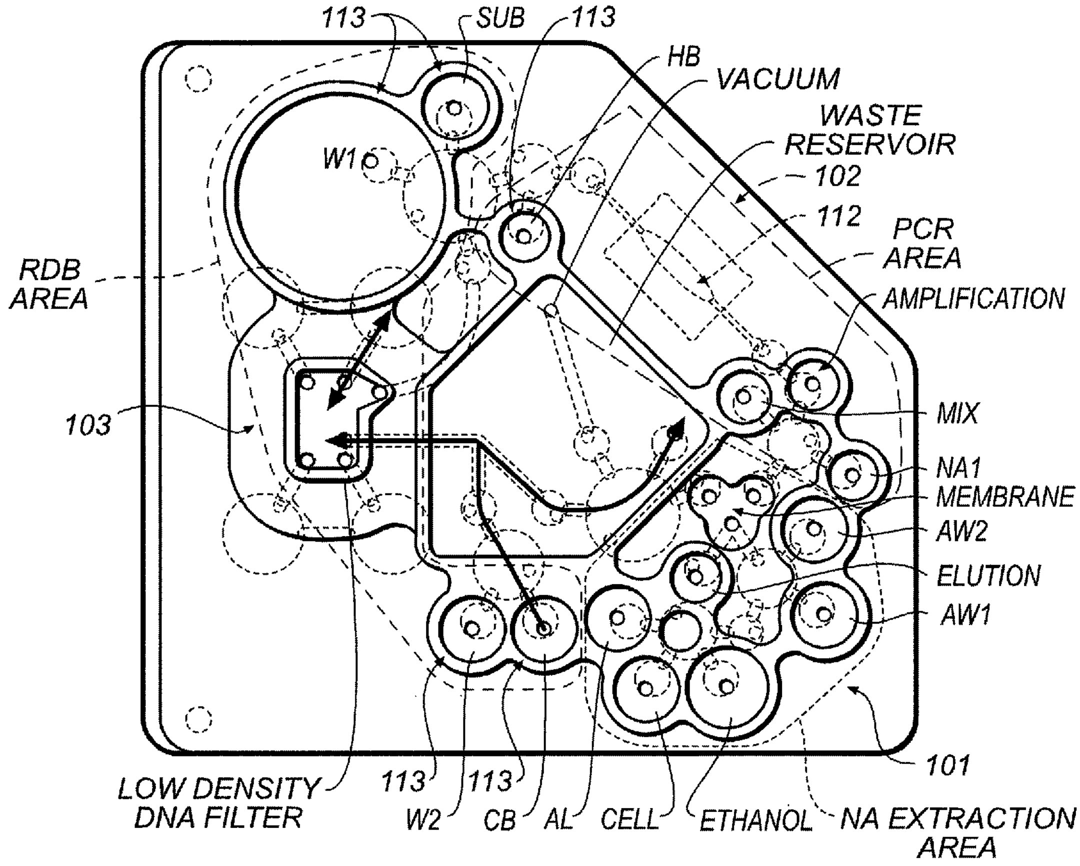
Figure 48:
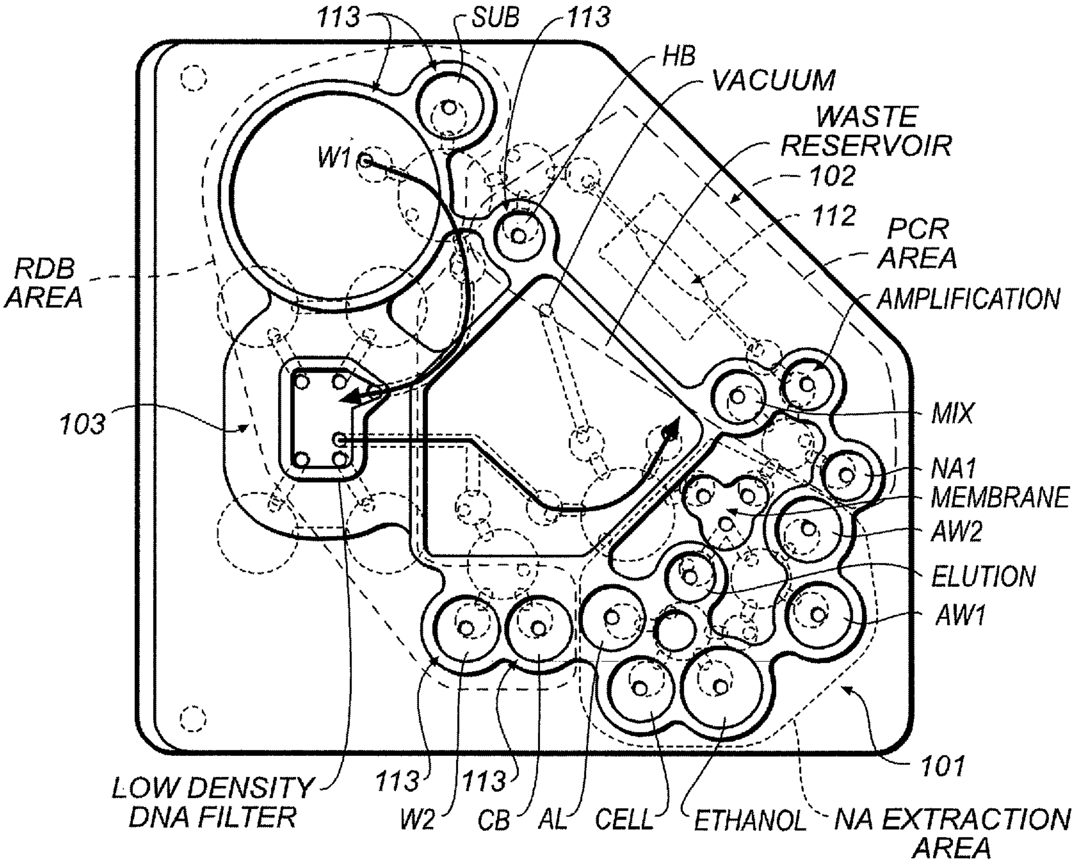
Figure 49:
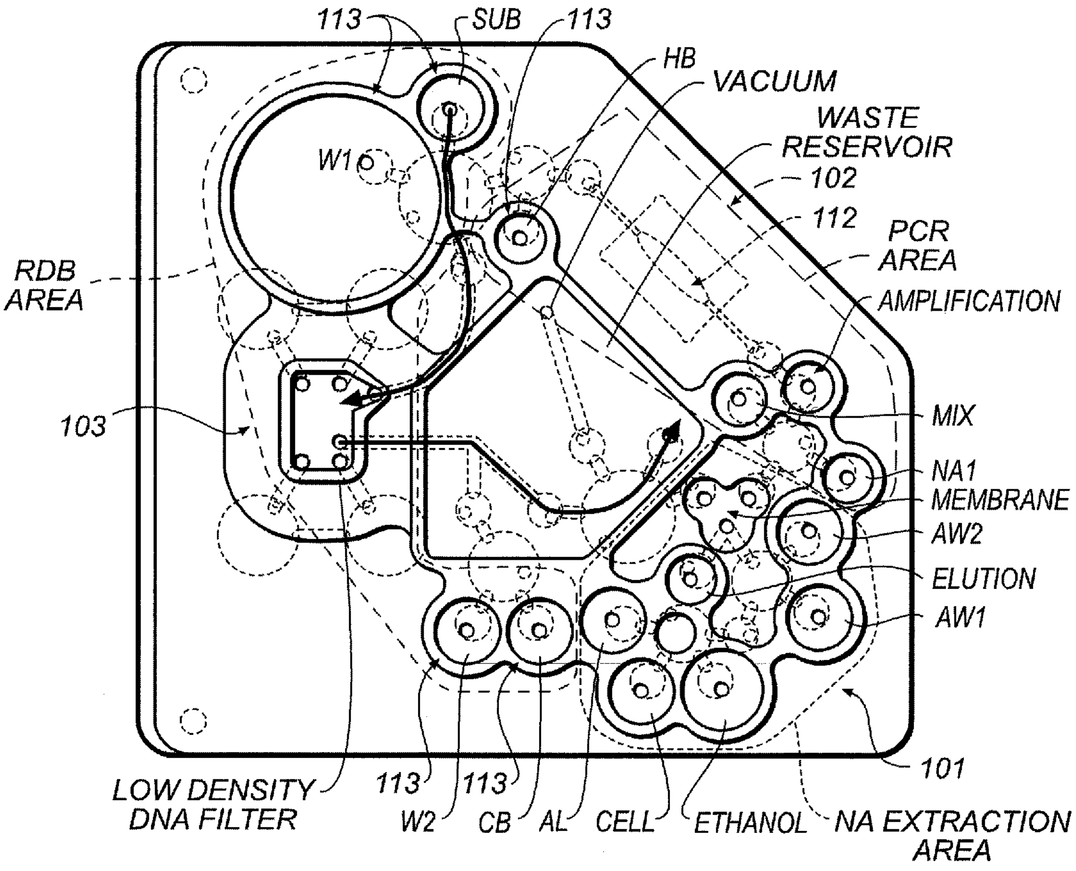
Figure 50:
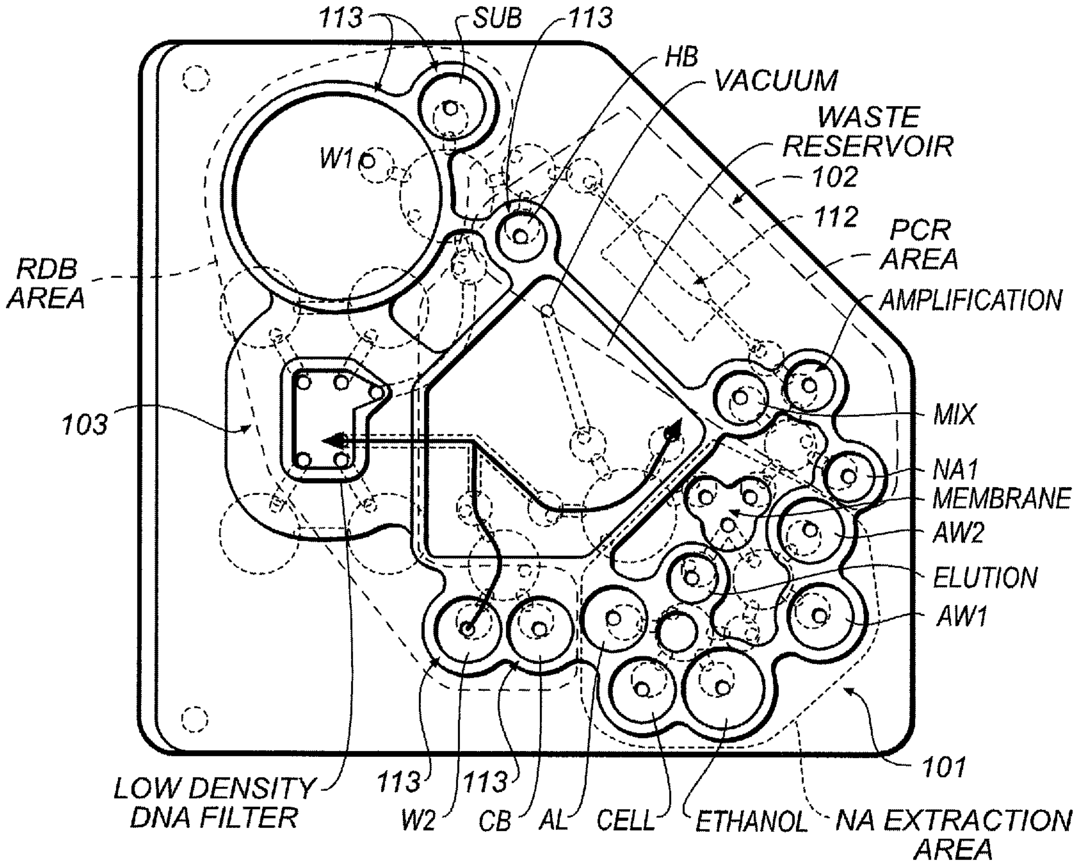

In FIGS. 7 and 45, 150 μl hybridization buffer is pumped into the nucleic acid analysis (e.g., Reverse Dot Blot or RDB) reservoir. Incubation is performed for 5 minutes. About 8-10 μl of the amplification product is heat denatured at 95° C. for 5 minutes. The amplification product is pumped into the nucleic acid analysis (RDB) Reservoir (FIG. 45). Solution is mixed by "fluffing" which is repetitive open/close operations of valve 32. The solution is incubated for 5 minutes and its contents emptied to waste (FIG. 46). The membrane is washed twice by pumping 150 μl buffer W2 into the reservoir, incubating for 1.5 minutes, and removing to waste. 150 μl conjugation buffer is pumped into the nucleic acid analysis (RDB) reservoir. The solution is mixed by repetitive open/close operations of valve 32 (FIG. 47). The solution is incubated for 3 minutes and the reservoir contents are emptied to the waste reservoir (FIG. 48). The membrane is washed 4-5 times by pumping 150 μl buffer W1 into the reservoir, incubating for 1 minute, and removing buffer to waste (FIG. 49). 100 μl of the substrate is pumped to the reservoir, incubated for 5-10 minutes, and the reservoir contents are emptied to the waste reservoir (FIG. 50). The membrane is washed twice by pumping 150 μl buffer W2 into the reservoir, incubating for 1.5 minutes, and removing the buffer to the waste reservoir.

6.2 Example 2

Microfluidic Device Embodiment with Two Functional Areas

This example describes another embodiment of the microfluidic device ("chip") that has two functional areas (FIGS. 8-11) and a method for using it.

FIG. 8 shows another embodiment of the microfluidic device with two functional areas, the sample preparation area and the nucleic acid amplification area. As indicated by arrows, the sample preparation area comprises reservoirs for sample input and preparation, sample purification and nucleic acid extraction. The nucleic acid amplification area comprises a nucleic acid amplification reactor ("amplification chamber"). This embodiment of the device also comprises a nucleic acid amplification products extraction area ("amplified products extraction area"), which is an area in which amplicons are extracted from the microfluidic device after nucleic acid amplification is complete. This particular embodiment of the device has dimensions of 50 mm×38 mm.

FIG. 9 is an exploded view of the microfluidic device of FIG. 8, showing its three layers (for clarity, the device is shown without the membrane).

FIG. 10 is a top view of the microfluidic device of FIG. 8, showing a map of the reservoirs, channels, valves and pumps of the device.

FIG. 11 is another top view of the microfluidic device of FIG. 8, showing a map of the pumps, valves and channels on the device.

In this embodiment of the microfluidic device, the reservoirs are as follows (FIG. 11):

Cells—suspended cells and Proteinase K
Mixer—buffer AL
Ethanol—Ethanol
AW1—Washing buffer AW1
AW2—Washing buffer AW2
Elution—Elution buffer AE
NA1—Nucleic acid reservoir 1
NA2—Nucleic acid reservoir 2
Amplification master mix—Amplification reagent reservoir
Amplicon outlet 1—Amplification outlet reservoir 1
Amplicon outlet 2—Amplification outlet reservoir 2
Amplification reactor An example of the progression of sample preparation during the operation of the embodiment of the microfluidic device shown in FIG. 11 is as follows:

1. Circulated cell lysis, 10-15 min.
2. Mix with ethanol
3. Transmit lysed cell solution to Si membrane/waste
4. Transmit AW1 and AW2 to Si membrane/waste
5. Vacuum on for 5-10 min for drying
6. Elution 1 and 2
7. Mix with PCR master
8. Load PCR reactor
9. PCR reaction
10. Discharge PCR product

6.3 Example 3

Microfluidic Device Embodiment with Two Functional Areas

This example describes another embodiment of the microfluidic device ("chip") that has two functional areas, a sample preparation area and a nucleic acid amplification area, but does not have an on-chip nucleic acid analysis area (FIGS. 12-16).

The device has body dimensions of 50 mm×38 mm and comprises three sandwiched layers that are bonded by a weak solvent bonding method of U.S. Patent Application 2006/0078470A1. The device further comprises a plurality of reservoirs disposed on a top surface of the device and in fluid connection with various valves and network of fluid channels. The device also comprises a nucleic acid amplification reactor that forms part of the functional fluidic network.

FIG. 13 shows the layout of the embodiment of the microfluidic device shown in FIG. 12, with three groups of bi-directional pumps depicted: for sample preparation, for PCR reagent preparation and for loading. Fluid can be transferred between reservoirs sharing the same pump diaphragm. The group of reservoirs circled "2" and "3" adjoining the nucleic acid amplification area are groups of reservoirs fluidically interconnected with the amplification area. The group of reservoirs circled "1" is a group of reservoirs in the sample preparation area. According to this embodiment, there are three groups of pumps. Fluid can be transferred between reservoirs sharing the same pump diaphragm. In this embodiment, seven of the pumps in group one, three of the pumps in group two, and two of the pumps in group three are used. In this embodiment, the pumps are bi-directional. Multiple source reservoirs may be combined into one destination reservoir simultaneously to create better mixing effects.

In one example of a method based on this embodiment (FIG. 14), cells are incubated with cell lysis buffer and Proteinase K at room temp for 5-10 min in reservoir R1. The cell lysis mixture is mixed with EtOH/DNA binding buffer from reservoir R2 by pumping R1 and R2 alternatively into R3. The mixed sample is transferred from reservoir R3 to the filter reservoir and the solution is pulled through a purification membrane (e.g., a silica membrane) that is located at the bottom of the reservoir.

The DNA that has bonded with the filter is washed with washing buffer 1 and the waste is transferred to the waste reservoir (FIG. 15). The bonded DNA is then washed with washing buffer 2 and the waste is transferred to the waste reservoir. The air pump is turned on for a few minutes to dry the membrane. Elution buffer is pumped to the filter reservoir, incubated and eluted to nucleic acid reservoir NA1. At this stage, some DNA can be aliquoted for bench top runs and the remaining is used for an on-chip run.

DNA template is transferred from NA1 to Nucleic Acid Amplification Mix and mixed (FIG. 16). Nucleic Acid Amplification master mix is pulled with DNA template into the reactor, where a thermal cycling protocol is performed. Nucleic acid amplification product is pumped into the product reservoir. At this stage, some DNA can be aliquoted for bench top runs and the remaining is used for an on-chip run.

6.4 Example 4

Amplification of Total RNA Using Microfluidic Device

This example describes the results of amplification of total RNA generated from HEK 293T cells using the embodiment of the microfluidic device shown in FIGS. 8-11. Total RNA was prepared on-chip and analyzed by gel electrophoresis using the following protocol:

0.1 N NaOH were run through all chambers of chip and repeated several times.

The chip was rinsed with water extensively by pumping water through all chambers, air dried, and the columns were assembled.

2 tubes of HEK 293T cells were thawed and centrifuged using routine methods, and the supernatant was removed.

600 μl of RLT/Bme (prep 2.0 ml RLT with 20 μl Bme) was added to each pellet, resuspended and the pellets were combined.

The resuspended pellet was homogenized by passing it through a Qiashredder column (2 sequential runs), using standard methods.

The volume was brought up to 1.5 ml with RLT-Bme and transferred to a 5 ml culture tube.

1.5 ml of 70% EtOH was added to the tube and mixed by inverting.

3×200 μl aliquots into were removed and placed into separate tubes.

To these tubes were added 500 μl of 1:1 RLT-Bme:70% EtOH and mixed well. These tube correspond to samples 1-3 of FIG. 13 (Qiagen control).

A standard off-chip column protocol (Qiagen RNeasy Mini Kit, Cat No. 74107) for Samples 1-3, and 10 was followed. RNA was eluted into 30 μl water (not prewarmed).

200 μl of the remaining original sample volume not used in Samples 1-3 were loaded directly into individual sample inlet columns on-chip by pipetting and using the pump to pull through the column to waste. The remaining sample volume was processed off chip along with Samples 1-3 and denoted sample 10 (Qiagen control).

The on-chip columns were washed with RW1, 2×22 μl.

The on-chip columns were washed with RPE, 4×22 μl.

The columns were allowed to dry for approximately 20 min.

Following drying of columns, 30 μl of room temperature water was added to chip samples 4-6 (by pipetting directly on column) and the samples were incubated for 10 min. The pure RNA was collected using on-chip pumping.

30 μl of warmed water was added to chip samples 7-9 (by pipetting directly on the column) and the samples were incubated for 10 min. The pure RNA was collected using on-chip pumping.

Another 10 μl of room temperature water was added to each column while pumping.

Pure RNA was transferred to a 1.5 ml tube to which another 20 μl water was added to account for lost volume from the chip.

Absorbance was read at 260 and 280 nm; 5 μl in total of 200 μl water (40× dilution).

5 μl of each sample was analyzed by using standard agarose gel electrophoresis; 1% agarose/TAE gel; 100 Volts, 30 min.

As seen in FIG. 18, the on-chip RNA preparation yielded similar quantity/quality of RNA compared to a standard Qiagen method (RNeasy Mini Kit, Cat No. 74107). This experiment also confirmed that during the on-chip nucleic acid preparation the on-chip diaphragm pump performs smoothly in handling high viscosity materials.

FIG. 19 shows the result of a RT-PCR amplification conducted on the microfluidic device ("chip") shown in FIGS. 8-11. The Invitrogen SuperScript™ One-Step RT-PCR with Platinum® Taq System was used for a PCR conducted in the nucleic acid amplification area. Total RNA generated from HEK 293T cells was prepared on-chip as described above, and used for template RNA. Primers recognizing β-actin were used to generate the cDNA and to amplify actin cDNA via PCR (RT-PCR). The forward primer was: ACG TTG CTA TCC AGG CTG TGC TAT [SEQ ID NO: 1] (present in Exon 3). The reverse primer was: ACT CCT GCT TGC TGA TCC ACA TCT [SEQ ID NO: 2] (present in Exon 5. The expected product was obtained, i.e., a cDNA amplicon of 687.

RNA was generated from HEK 293T cells. Primers recognizing beta-actin were used to generate the cDNA product and to amplify actin cDNA via PCR (FIG. 19). Lane 1, DNA standards; Lane 2, amplicon product from RT-PCR performed on-chip, Lane 3, input RNA (1 μl).

FIG. 20 shows the on-chip repeatability for eight PCR runs for varying thermal cycles and run times as shown.

FIG. 21 shows comparative results between the microfluidic device and a conventional bench top PCR platform. For 5000 plasmid copies over 30 thermal cycles, the on-chip results were obtained in one hour compared to 1.75 hours for the bench top run.

FIG. 22 shows a typical cycle from the PCR thermal cycler used in this experiment in conjunction with the microfluidic device. The graph at the bottom is an expanded view of several of the first four cycles shown in the top graph.

FIG. 23 shows the results of a RT-PCR protocol run on the microfluidic device. Briefly, HIV RNA was isolated using bench top (bt) and on-chip protocols as follows. 20,000 (Bt1) and 2,500 (Bt2) copies of Armored RNA were used for bench top and on-chip RNA isolation. Bench top elute volume was 50 μl; theoretical 100% yield is 400 copies RNA/μl. On-chip elute volume was 20 μl; theoretical 100% yield is 125 copies RNA/μl. A 1 ml elute volume was used for RT-PCR.

A standard RT-PCR protocol known in the art was run using reverse transcript for 30 minutes at 50° C. followed by 15 minutes at 95° C. then the PCR protocol was run for 40 cycles using 45 seconds at 95° C. then 45 seconds at 58° C. and 60 seconds at 72° C. Isolation yields were estimated from gel images after RT-PCR.

As shown in FIG. 23, the RNA obtained from the on-chip run yielded at least a comparable amount of RNA as the same protocol performed on the bench top under identical experimental conditions using the Qiagen RNAEasy kit. Lane 1: molecular weight standards. Lane 2: Bt1-RNA. Lane 3: Bt2-RNA. Lane 4: Chip-RNA.

6.5 Example 5

Methods for Detecting PCR Products Using a Microfluidic Device

The following data demonstrate that a user can utilize the microfluidic device to rapidly and easily perform PCR with virtually no intervention. All necessary steps, including the lysis of cells, extraction and purification of DNA or RNA, and PCR or RT-PCR of the nucleic acids can be achieved on a single microfluidic device system. Furthermore, a system has also been designed that is capable of denaturing the PCR amplicons and detecting the PCR products via hybridization on an array of oligonucleotide probes by reverse dot blot (RDB) analysis.

The embodiment of the microfluidic device used in this example had two functional areas. The embodiment shown in FIGS. 8-11 was actually used, but the microfluidic device shown in FIGS. 12-16 could also be used. The microfluidic device had an inexpensive three-layered polystyrene-based lamination system that once assembled and laminated by a proprietary process, creates pumps, valves, microfluidic channels, reagent reservoirs, DNA/RNA extraction/purification components, and thermocycling capabilities. In addition, the design of the system enables a bidirectional flow of fluids that is very useful for certain assay steps such as cell lysis. Finally, there is no fluidic contact between the microfluidic device and the controller, thus reducing the possibility of contamination.

The configuration of the various microchannels, pumps and valves, can be easily changed, and the format of the microfluidic device is sufficiently versatile to permit the analysis of a broad spectrum of specimens. Briefly, with reference to the embodiment shown in FIGS. 12-16 (although the embodiment in FIG. 8-11 could also be used) a sample progresses through the following steps as it is subjected to nucleic acid amplification analysis on the microfluidic device system (FIGS. 14-16).

1. The raw clinical sample is introduced into reservoir R1, which contains cell lysis buffer and Proteinase K.
2. Contents of R1 are mixed with ethanol and nucleic acid binding buffers contained in reservoir R3 by pumping R1 and R3 alternatively into reservoir R2.
3. The mixed sample (now in R2) is transferred to the filter reservoir (Filter Res) and pulled through a silica membrane located at the bottom of the reservoir, to bind the extracted nucleic acids to silica.
4. The silica-bound nucleic acids are washed with buffer contained in W1, with the waste transferred to the waste reservoir.
5. The silica-bound nucleic acids are washed with buffer contained in W2, with the waste transferred to the waste reservoir.
6. The air pump is turned on to dry the silica membrane.
7. Elution buffer (from reservoir Elu) is pumped to the Filter reservoir and incubated, followed by elution of 25 μL of purified nucleic acid into reservoir NA1.
8. The purified nucleic acid from NA1 is transferred to the nucleic acid amplification Mix reservoir and the template mixed with the nucleic acid amplification reagents in 1:9 ratio (i.e., primer pairs and all other nucleic acid amplification reaction components).
9. The nucleic acid amplification master mix and nucleic acid template is pulled into nucleic acid amplification reactor.
10. Nucleic acid amplification thermal cycling is performed within nucleic acid amplification reactor.
11. The final nucleic acid amplification products are pumped into the product reservoir (PCR Prod).

RNA Isolation and Purification

To determine if the microfluidic device can efficiently extract and purify RNA in a manner similar to "bench top" methods, RNA was isolated from human embryonic kidney cells (HEK 293-T) by subjecting equal quantities (500,000 cells) of cells to extraction using both the microfluidic device and the bench top both using the Qiagen RNeasy protocol. Agarose gel electrophoresis of multiple replicates of each of the two protocols indicates that the microfluidic device performed equivalently to the "bench top" methodology (FIG. 18).

PCR Comparison Using a Bench Top Thermocycler and the Microfluidic Device System To demonstrate that effective thermocycling can be accomplished on the microfluidic device, $5\times10^3$ copies of plasmid (prlpGL3) were amplified through 30 cycles using either a Bio-Rad MJ Mini Thermocycler or the thermocycler used in the microfluidic device mounted on the controller. In both cases the appropriate amplicons were obtained, as viewed by agarose gel electrophoresis, indicating that the microfluidic device system was capable of generating the correct amplicons, with virtually no "hands on" effort required (FIG. 21).

Use of the Microfluidic Device System to Detect β-Thalassemia and HPV

Once the general conditions of the nucleic acid extraction and purification, along with the microfluidic device thermocycling have been developed, detection of specific gene targets upon introduction of raw samples is accomplished. In order to demonstrate how quickly a particular prototype microfluidic device could be configured to detect the targets of interest, microfluidic devices were developed that performed bench top protocols academic laboratories have already developed to detect particular targets of interest via PCR analysis. Without any significant optimization of the microfluidic device the system to perform all required preparative and analytical steps (i.e., cell lysis, nucleic acid extraction/purification and PCR amplification) using standard assay conditions and protocols known in the art.

Using this approach, various different clinical specimens have been analyzed. By way of example, whole human blood (50 μL) was introduced into the microfluidic device and by means of the bidirectional flow between the sample reservoir and the lysis buffer reservoir, the cells were lysed. Nucleic acids were flowed through the silica membrane component on the microfluidic device.

Finally, after 30 cycles of PCR two identical samples that were PCR amplified in parallel using either a bench top thermocycler (lanes 4-5) or the microfluidic device system (lanes 2-3) were analyzed on agarose gels (FIG. 24).

Furthermore, lanes 2 and 4 were obtained from one specimen while lanes 3 and 5 were obtained from a second specimen. The apparent discrepancy in signal intensity regarding the stronger signals obtained through the bench-top PCR reaction is most likely due to the different volume of starting material employed for the microfluidic device. The starting volume of the bench top PCR analysis was 200 μL while that used in the microfluidic device was only 50 μL. More importantly, the electrophoretic mobility of both sets of PCR amplicons was virtually identical.

In a similar manner, vaginal swabs were analyzed by PCR for the presence of human papilloma virus (HPV) using the L1 gene degenerate primers MY09/MY11 (Gravitt P E, Peyton C L, Apple R J, Wheeler C M: Genotyping of 27 human papillomavirus types by using L1 consensus PCR products by a single-hybridization, reverse line blot detection method. J Clin Microbiol 1998, 36(10):3020-3027).

Vaginal swabs were placed into PBS buffer and after agitation, the supernatant was analyzed for the presence of HPV using either bench top PCR methods or the microfluidic device system. As shown in FIG. 25, the microfluidic device system provided results that were essentially identical to those obtained using bench top methods.

Three individual vaginal swabs were suspended in PBS and either subjected to "bench top" (right) lysis, DNA extraction/purification and PCR or simply introduced into a microfluidic device (right) and all functions automatically performed. Samples 1, 2 and 3 represent three individual samples that were split into two aliquots and analyzed as described above.

In the case of the bench top method, viral DNA was first isolated and purified and then PCR amplified using a bench top thermocycler. In the case of the microfluidic device system, the PBS supernatant was simply added to the sample well and all functions were automatically performed (including viral lysis, nucleic acid extraction/purification, and PCR).

A microfluidic device that incorporates a reverse dot blot (RDB) module (i.e., a nucleic acid analysis area) to detect human papilloma virus (HPV) was used. HPV was obtained from vaginal swabs and subjected to PCR amplification using primer pairs that can amplify multiple serotypes of HPV. On the microfluidic device, the biotinylated amplicons were denatured and allowed to flow onto the 4×4 array of probes against serotypes HPV-11, HPV-16, HPV-31, and HPV-52, following the protocol schematically described in FIG. 27. HPV-52 (top) and HVP-11 (bottom) were correctly detected in the integrated microfluidic device system (FIG. 26).

To test its utility, we amplified vaginal swab samples with MY09/MY11 degenerate primers (Peyton C L, Wheeler C M: Identification of live novel human papillomavirus sequences in the New Mexico triethnic population. J Infect Dis 1994, 170(5):1089-1092) that can amplify a variety of different HPV serotypes (HPV 11, 16, 31 and 52). Both primers were biotinylated at their 5' ends to generate double stranded, biotinylated amplicons. The RDB module was configured to denature the PCR amplicons and flow them onto the surface of a dot blot array (Immunodyne C, Pall Life Sciences, Ann Arbor Mich.) where the amplicons hybridized with their respective capture probes.

In addition to the above studies, we have successfully used the microfluidic device system to detect HIV-1 in both plasma and saliva, achieving results equivalent to those obtained using "bench top" RT-PCR methods.

Taken together, these preliminary data show that the microfluidic device can be used to achieve fully automated PCR or RT-PCR analysis of clinical samples in an easy-to-use format.

6.6 Example 6

On-Chip Processing of *E. coli* Sample

The embodiment of the microfluidic device used in this example had two functional areas (FIGS. 12-16). DH5a, a derivative of the non-pathogenic K12 strain of *E. coli*, was used as the source of the sample for on-chip processing. The primers were generated based on the genome of DH10b. 16S ribosomal RNA encoded by the rrs gene. "Enterobacterial common antigen" (ECA) is encoded by the wzyE gene. Primers used were: 16S_367 (7X/genome) and ECA_178 (1X/genome) (see Bayardelle P. and Zafarullah M. (2002) Development of oligonucleotide primers for the specific PCR-based detection of the most frequent Enterobacteriaceae species DNA using wec gene templates. Can. J. Microbiol. 48: 113-122).

FIGS. 14-16 are schematic diagrams of the operation of the embodiment of the microfluidic device used in this experiment. The arrows show the progression of the *E. coli* sample as it was processed on the device. In FIG. 14: 1. *E. coli* was incubated with cell lysis buffer and Proteinase K at room temp for 5-10 min in reservoir R1. 2. The sample was then mixed with EtOH/DNA binding buffer from R2 by pumping R1 and R2 alternatively into R3. 3. Mixed sample were transferred from R3 to the filter reservoir and the solution was pulled through a silica membrane located at the bottom of the reservoir.

In FIG. 15: 4. The bonded DNA is washed with washing buffer 1 and the waste transferred to waste reservoir. 5. The bonded DNA is then washed with washing buffer 2, and the waste transferred to the waste reservoir. 6. The air pump is then turned on for a few minutes to draw air through the silica membrane to dry the silica membrane. 7. Elution buffer is pumped to the filter reservoir, incubated and eluted to NA1. At this stage, some DNA can be aliquoted for bench top runs and the remaining is used to progress with the on-chip run.

In FIG. 16: 8. DNA template is transferred from NA1 to PCRMix and mixed. 9. PCR master mix is pulled with DNA template into the PCR reactor. 10. PCR thermal cycling conducted. 11. PCR product pumped into the product reservoir. At this stage, some DNA can be aliquoted for bench top runs and the remaining is used to progress with the on-chip run.

The automation reliability and automation efficiency was assessed, using PCR sensitivity analysis and absorbance studies, by determining the success rate when an automated run was conducted with a "reasonable" ($10^3$ level) *E. coli* loading. 80-90% success rates were obtained using both designs. For many commercially available PCR products, ~90% successful rate is typical.

Automation efficiency was assessed by comparing the NA extraction and PCR results obtained from the microfluidic device versus the bench top result.

There were two sequential on-chip operations: nucleic acid (NA) extraction and PCR amplification. Direct comparison for NA extraction at low *E. coli* loading was difficult because DNA from 20 μl sample of 1000 *E. coli*/μl gives rise to undetectable UV absorbance for conventional UV spectrometer.

FIG. 28 shows a comparison between two chips processing 1,000 *E. coli* loaded into apple juice. The loaded juice was prepared and the DNA purified on-chip then two 1 μl aliquots were removed and amplified on the bench top and the remaining purified DNA was amplified on-chip. The product was removed and analyzed on gel as shown. Lane 1 and Lane 2 of each chip's product represent the aliquot which was amplified on the bench top and Lane 3 in each case represents the on-chip amplified product.

For PCR, DNA extracted on-chip is used as template for both bench top and on-chip PCR runs to determine the on-chip PCR efficiency. FIG. 29 shows a comparison of bench top and on-chip PCR results using on-chip extracted DNA. *E. coli* loading ranges were from $5\times10^3$/μl-$1\times10^4$/μl.

When the loading is sufficient, on-chip and bench top results were very comparable.

6.7 Example 7

Detection of *E. coli* in Food Matrices Using the Microfluidic Device

The main objective of the present study was to demonstrate that an embodiment of the microfluidic device can effectively perform all preparative and analytical steps to detect *E. coli* in food matrices such as apple juice, apple cider and milk using a PCR-based assay.

*E. coli* strain DH5α was grown in culture and introduced into the various matrices used. Two different gene targets were used in this study. A 16s rRNA gene (encoded by rrs gene), a highly conserved gene observed across bacterial families and species, and the enterobacterial common antigen, ECA (encoded by the wyzE gene), common to the Enterobacteriacea family were PCR amplified. The PCR primers used to detect the rRNA and ECA genes were expected to generate amplicons of 367 bp and 178 bp, respectively.

Two separate embodiments of the microfluidic device were evaluated and three separate *E. coli* introduced samples (apple juice, apple cider and milk) were evaluated at loading concentrations ranging from 1000 to 500,000 microbes. Finally, a total of approximately 100 microfluidic device runs were performed during this preliminary study.

Results

Although two different designs were evaluated during this study, this example focuses on only one of the designs evaluated (FIGS. 18-21). This microfluidic device utilizes two functional areas on a single microfluidic device. The first area incorporates all sample preparation (i.e., cell lysis, DNA extraction/purification), and the second is for PCR amplification. Within these areas are located three groups of pumps/valves to accomplish the various functions. Fluids can be transferred between the various reservoirs sharing the same pump diaphragm. In addition, multiple source reservoirs can be combined into a single destination reservoir to accomplish effective mixing, which can also be enhanced by the bi-directional nature of the pumps. Briefly described, the following steps were.

1. Incubate 20 μL *E coli* sample with cell lysis buffer and Proteinase K at room temperature for 5-10 min in R1.
2. Mix R1 with EtOH/DNA binding buffer from R3 by pumping R1 and R3 alternatively into R2.
3. Transfer mixed sample from R2 to the filter reservoir and pull the solution through a silica membrane located at the bottom of the reservoir to bind the extracted DNA to silica.
4. Wash the silica-bound DNA with washing buffer 1 in W1, transfer the waste to waste reservoir.
5. Wash the silica-bound DNA with washing buffer 2 in W2, transfer the waste to waste reservoir.
6. Turn the air pump on for a few minutes to pull air through the silica membrane in order to dry the silica membrane
7. Pump Elution buffer (from reservoir Elu) to Filter reservoir, incubate and elute 25 μl purified DNA to reservoir NA1.
8. Transfer DNA template from NA1 to the PCRMix reservoir and mix template with the PCR reagents in 1:9 ratio (i.e., primer pairs and all other PCR reaction components).
9. Pull PCR master mix with DNA template into the PCR reactor.
10. Conduct PCR thermal cycling within PCR reactor.
11. Pump PCR product into the product reservoir (PCR Prod).

Although approximately 100 separate assays were performed during this preliminary effort, this example describes representative data that was very reproducible from run to run. The data presented in FIGS. 28-37 represent results obtained from the introduction of a known amount of *E. coli* into PBS buffer, apple cider, apple juice and milk.

We found that when Qiagen DNAEasy kit was used to extract DNA, the sample volume may vary from 10-30 μl to no noticeable effect.

After the sample was placed in R1 with cell lysis buffer ATL and Proteinase K, it was then automatically processed as described above and the final volume of the DNA eluted from the silica membrane was 25 μL. To conduct PCR, the DNA template was mixed with PCR master in the ratio of 1:9 before it was introduced into the thermal cycling chamber. Therefore, even if in the unlikely event the DNA recovery was assumed to be 100%, the total amount of DNA that would ultimately be PCR amplified would theoretically represent DNA obtained from no more than $1/25^{th}$ of the total starting number of microbes (e.g., if the starting number of microbes was 1000, the DNA that was finally introduced to the PCR chamber would be no more than 40 microbes).

*E. coli* Suspended in PBS

To help establish assay conditions, initial efforts focused on a known amount (or number) of *E. coli* introduced into PBS. 500,000 organisms were introduced into PBS and DNA isolated/purified on the microfluidic device. A 1 μL aliquot of the 25 μL isolated DNA template was removed and subjected to "bench top" PCR amplification, while another 1 μL aliquot of the 25 μL isolated DNA template was mixed with PCR master mix in 1:9 ratio and further amplified on the microfluidic device. In FIG. 32, comparison of the gel profile of the "bench top" PCR sample (lane 3) with that obtained from fully integrated DNA isolation/purification and PCR on the same microfluidic device (lane 4) revealed indistinguishable results. Lanes 1 and 2 on the same gel represent the negative (water) and positive (DNA from 1000 microbes based on UV absorbance measurement) controls, respectively. Repeat analysis of the same types of sample yielded essentially reproducible results, indicating that the microfluidic device could be used to reliably detect the microbes in question and obtain PCR results that were virtually indistinguishable from "bench top" PCR analysis.

By introducing only 10,000 microbes into the initial 20 μL sample and then processing exactly as described above through three separate microfluidic device devices, essentially identical results were obtained.

DNA Isolation and Purification on Microfluidic Device

By performing several additional experiments similar to the above, the following assay protocol was established:

Reagents were from the Qiagen DNEasy kit and Promaga PCR kit.

| Reagent | Volume (μL) | Comments |
|---|---|---|
| Sample | 20 | |
| ATL | 20 | Cell lysis buffer |
| Proteinase K | 3 | |
| AL | 40 | Si Membrane binding buffer |
| Ethanol | 40 | To assist in drying membrane |
| AW1 | 50 | Wash buffer 1 |
| AW2 | 50 | Wash buffer 2 |
| AE | 50 | DNA elution buffer |

PCR Protocol

Initial 2 minute incubation at 95° C. 25-35 cycles with each cycle being:

5-15 sec at 95° C.

20-30 seconds at 60° C.

20-25 seconds at 72° C.

Final incubation for 3 minutes at 72° C.

*E. coli* Introduced into Apple Cider

In a manner similar to that reported for microbes introduced into PBS, various concentrations of *E. coli* were introduced into commercially obtained apple cider and analyzed in the microfluidic device system. Analysis of 500,000 microbes introduced into apple cider (FIG. 30A) yielded results that were essentially indistinguishable between "bench top" PCR analysis (lane 3) and fully integrated microfluidic device analysis (lane 4). Lanes 1 and 2 represent the negative and positive controls, respectively. The slight band that appears in the negative control lane is likely due to cross contamination in the laboratory. Reducing the number of microbes introduced into the apple cider to 100,000 again revealed good amplification of the target sequences (FIG. 30B). Lanes 1-2 reveal the amplicons generated by a fully integrated microfluidic device run, while lanes 4-5 reveal the amplicons generated by a "bench top" PCR amplification of the same DNA. Lane 3 represents the negative control.

Finally, reducing the number of microbes introduced into apple cider to 2500 (FIG. 31), again excellent correlation between "bench top" PCR analysis (lanes 2-3) and fully integrated microfluidic device analysis (lanes 4-5) were obtained. Lane 1 represents the negative control.

As noted above, due to the manner in which the DNA is extracted, purified and amplified on the microfluidic device (as well on bench top system), the following table represents the number of microbes loaded to the microfluidic device and actually amplified in the PCR chamber: (assuming a 100% recovery of DNA from the microfluidic device purification area The following Table 1 sets forth the loading number of microbes in the sample and in the PCR chamber:

TABLE 1

| Loading number of microbes in 20 μL sample | Loading number of genome equivalents in PCR chamber |
|---|---|
| 500,000 | 20,000 |
| 100,000 | 4,000 |
| 2,500 | 100 |

*E. coli* Introduced into Apple Juice

In a similar manner, various concentrations of microbes were introduced into commercially obtained apple juice. When 10,000 microbes were introduced into the apple juice (FIG. 33), the results obtained from a fully integrated microfluidic device run (lanes 4-5) were indistinguishable from the results obtained by "bench top" PCR analysis of DNA isolated on the same microfluidic device. Lane 1 represents the negative control.

Introducing only 1000 microbes into the apple juice (FIG. 34) again reveals that amplicons resulting from the fully integrated microfluidic device (lanes 4-5) were indistinguishable from the amplicons obtained by bench top PCR of DNA isolated on the same microfluidic device (lanes 2-3). As above, lane 1 represents the negative control. Finally, comparing the amplicons obtained from two different microfluidic device runs (FIG. 35), the fully integrated results (lanes 3 of each microfluidic device) were indistinguishable from the results obtained by "bench top" PCR amplification of DNA obtained from the same microfluidic device.

As described above, due to the dilution of DNA as it is processed through the microfluidic device, the amplicons that result from the isolation/purification and PCR amplification that microbes initially introduced into the microfluidic device represent no more than $1/25^{th}$ of the initial input concentration. Therefore, when 10,000 microbes were introduced, DNA from no more than 400 microbes was actually amplified. Similarly, when only 1000 microbes were introduced, DNA from no more than 40 microbes was actually amplified.

*E. coli* Introduced into Milk

When 1,000,000 *E. coli* was introduced in the milk and tested using the established protocol described above, the situation was more complex than apple juice or apple cider. For skim milk, the protein interference to the test was very limited and the anticipated result was obtained (FIG. 36). However, when whole milk was tested at a 1:1 volume ratio to the cell lysis buffer, no DNA was isolated likely indicating that the fats present in the whole milk suppress the isolation process.

The Whatman FTA filter that was developed for storage and transport, of blood for clinical diagnostic purposes was used during this particular protocol. The most noticeable feature of the Whatman FTA filter was that it comprises reagents sufficient for cell lysis and purification on the filter itself. In this case, there was no need to store other reagents on the microfluidic device except water. However, the Whatman FTA filter entails rather harsh conditions to process. Both bench top and on the microfluidic device FTA elution for purification of DNA from *E. coli* was tested and the results are summarized in Table 2 and in FIG. 37. All tests were performed using 1 million *E. coli* loadings.

TABLE 2

| Lane# | 1 | 2 | 3 | 4 | 5 | 6 | 7 |
|---|---|---|---|---|---|---|---|
| Test | Neg, apple juice | Pos, apple juice | Pos, apple juice | Neg, milk | Pos, milk | Pos, milk | Cider |

Conclusions

This study demonstrated that the microfluidic device system can be used to detect *E. coli* in such food matrices as apple juice, apple cider and milk. These results clearly demonstrate that all preparative and analytical functions can be performed on a single microfluidic device.

6.8 Example 8

Pressure Relief Device for a Closed Nucleic Acid Amplification Reactor

This example describes a pressure relief device that can be used with a closed nucleic acid amplification reactor in the nucleic acid amplification area of a microfluidic device, e.g., with a PCR reactor. A pressure relief (cushioning) device can be installed inside a sealed microfluidic device. The pressure relief device is similar to a valve but with a conduit cut through the diameter (see FIG. 38); fluid can normally flow through the conduit above the diaphragm; when the system pressure is increased, the fluid will push against the cushioning device diaphragm that is pneumatically controlled or left open to atmosphere depending on design and system pressure; the deflection of the diaphragm provides additional space for pressure relief meanwhile keeping the mass inside the closed system.

The pressure relief device can prevent sealed miniaturized reactors such as microfluidic devices from experiencing breaking or leaking from significant temperature changes during thermal cycling. The pressure resulting from liquid thermal expansion is extremely high within a fixed volume. If the temperature is increased from 25° C. to 95° C., the volume of water will increase by 4%. In a conventional reactor design, the pressure might be released by the deformation of reactor wall, compression of trapped gas, inlet/outlet conduit expansion, leakage, etc.

With the cushioning device in line inside the system, when temperature is increased in the area of reactor, the liquid inside the reactor will expand and pressure will increase, deflecting the cushioning diaphragm. As a result, the system pressure is released. When temperature is decreased in the reactor, the liquid will contract, leading to the backflow of the fluid and the diaphragm deflection is reduced. In addition, the pressure cushioning design also facilitates the use of valves to seal the system otherwise a high-pressure valve would be required.

6.9 Example 9

Prevention of PCR Reactor Deformation at Elevated Temperatures

This example describes a rigid structure that, in certain embodiments, can be bonded on top of a nucleic acid amplification reactor, e.g., a PCR reactor, to prevent the reactor from bowing up as a result of thermal effects at elevated temperatures (see FIG. 39). The top of the reactor can undergo "bowing up" deformation at elevated temperatures, e.g., 95° C. when using polystyrene as the microfluidic device material. When cooled down, the pressure inside the chamber can be negative due to the deformation and/or leaking loss of liquid, which leads to bottom film bowing up and losing conformal contact with the heater. As a result, it could be difficult to achieve reproducible and high quality nucleic acid amplification. By using a rigid structure above the reactor, such thermal expansion is directed away from the top of the reactor and to the membrane that is pressing on the heater.

6.10 Example 10

Method for Immobilizing Nucleic Acid Probes for Reverse Dot Blot (RDB)

This example describes a method that can be used to immobilize nucleic acid probes for Reverse Dot Blot (RDB) detection.

A Biodyne C membrane was prepared as follows. The filter was cut to size suitable for soaking in a 10 cm petri dish. The membrane was rinsed in 0.1 N HCl in the petri dish. The membrane was soaked in an aqueous solution of 10% N-Ethyl-N'-(3-dimethylaminopropyl)carbodiimide hydrochloride (EDC) in water for 15 min (making EDC immediately before use) using approximately 5 ml of EDC with agitation. The membrane was rinsed in sterile water and air-dried overnight.

20 μM solutions of amino-terminated probes were generated as follows:

1. mix 50 μl of a 200 μM probe solution from a (0.5 M NaBicarbonate) stock solution
2. into 445 μl of 0.5M NaBicarbonate solution
3. to which then add 5 μl food dye (yellow-For 1; red-Gb) for a total volume of 500 μl
4. dip a pin into the prepared solution and dispense a drop from the pin onto the earlier prepared Biodyne C membrane by contacting the pin to the Biodyne C membrane for 1 second, and repeat for two cycles.

Prepare another solution using the same protocol as above but using different probes. When an array of probes are completed then;

5. Wash the Biodyne C membrane with the probe array for five seconds in 0.1 N NaOH.
6. Then wash a second for 5 seconds in sterile water.
7. Then dry for 35 seconds with convective heat drying.
8. Air dry completely
9. Rinse in 0.1 N NaOH~1 min
10. Rinse in sterile water
11. Air dry completely The present invention is not to be limited in scope by the specific embodiments described herein. Indeed, various modifications of the invention in addition to those described herein will become apparent to those skilled in the art from the foregoing description. Such modifications are intended to fall within the scope of the invention.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A microfluidic device for analyzing a sample of interest comprising:
   - a) a microfluidic device body, wherein the microfluidic device body comprises:
     - i) a sample preparation area,
     - ii) a non-actuated, fixed volume nucleic acid amplification area, and
     - iii) a plurality of fluid channels interconnected in a network, and wherein each of the sample preparation area and the nucleic acid amplification area are fluidly interconnected to the other area by at least one of the plurality of fluid channels in the network, characterized in that the device body further comprises:
     - a single, non-elastomeric substrate layer having upper and lower surfaces, and having one or more microfeatures in the upper surface thereof; and
     - a single, non-elastomeric membrane layer contacting and joined with the upper surface of the substrate and disposed over the one or more microfeatures to form a diaphragm valve, having a relaxed state wherein the non-elastomeric membrane lies substantially against the upper surface of the substrate and an actuated state wherein the membrane is moved away from the upper surface of the substrate, further wherein the device is a two-layer device consisting of the substrate layer and the membrane layer.

2. The microfluidic device of claim 1, further comprising: iv)) a nucleic acid analysis area,
   and wherein the nucleic acid analysis area is fluidly interconnected to at least one of the other two areas by at least one of the plurality of fluid channels in the network.

3. The microfluidic device of claim 2, comprising a differential pressure source capable of exerting a positive pressure or a negative pressure with respect to ambient pressure on a selected area of the microfluidic device body.

4. The microfluidic device of claim 3, comprising a differential pressure delivery system operably connected to the differential pressure source and to the microfluidic device body.

5. The microfluidic device of claim 3, comprising at least one diaphragm disposed in at least two of the plurality of fluid channels for transforming a pressure from the differential pressure source to a desired open or closed position.

6. The microfluidic device of claim 2, wherein the sample preparation area comprises:
   - a sample intake reservoir;
   - a reservoir for a sample preparation reagent; and
   - sample purification media;

wherein the sample intake reservoir, the reservoir for the sample preparation reagent, and the sample purification media are fluidly interconnected.

7. The microfluidic device of claim 6, comprising a sample purification media reservoir, wherein the sample purification media is disposed in the sample purification media reservoir.

8. The microfluidic device of claim 7, wherein the sample purification media is disposed in the bottom of the sample purification media reservoir.

9. The microfluidic device of claim 6 wherein the sample purification media is disposed in one of the plurality of fluidic channels.

10. The microfluidic device of claim 2, wherein the nucleic acid amplification area comprises:
    - a nucleic acid amplification reactor;
    - a nucleic acid amplification reagent reservoir; and
    - a nucleic acid amplification product reservoir;
    - wherein the nucleic acid amplification reactor, the nucleic acid amplification reagent reservoir, and the nucleic acid amplification product reservoir are fluidly interconnected.

11. The microfluidic device of claim 2, comprising a nucleic acid amplification products analysis area.

12. The microfluidic device of claim 11, wherein the nucleic acid amplification products analysis area comprises a nucleic acid analysis reservoir.

13. The microfluidic device of claim 6, wherein the sample purification media is a silica membrane.

14. The microfluidic device of claim 2, wherein the sample of interest is a fluid material, a gaseous material, a solid material substantially dissolved in a liquid material, an emulsion material, a slurry material, or a fluid material with particles suspended therein, and further comprising at least one of a biological material and a suspension of cells in a fluid.

15. The microfluidic device of claim 2, wherein the microfluidic device body comprises a plurality of layers of weak solvent-bonded polystyrene.

16. The microfluidic device of claim 2 wherein the sample preparation area comprises a sample mixing diaphragm fluidly connected to the sample intake reservoir.

17. The microfluidic device of claim 2, wherein the microfluidic device body comprises a means for air-drying the sample purification media.

18. The microfluidic device of claim 2, wherein the sample preparation area comprises at least one of a waste reservoir and an elution reagent reservoir.

19. The microfluidic device of claim 6, wherein the sample preparation reagent comprises magnetic beads.

20. The microfluidic device of claim 6, wherein the sample preparation reagent comprises a lysing reagent.

21. The microfluidic device of claim 10, wherein the nucleic acid amplification reactor is a thermal cycling reactor.

22. The microfluidic device of claim 21, wherein the bottom of the thermal cycling reactor is a thin layer of polystyrene.

23. The microfluidic device of claim 21, wherein the bottom of the thermal cycling reactor is heated during thermal cycling by a heater that is not disposed on or in the microfluidic device body.

24. A method for detecting a nucleic acid of interest comprising the steps of:

obtaining a sample suspected of containing the nucleic acid of interest;

providing the microfluidic device of claim 1;

introducing the sample into the sample preparation area;

preparing the sample for nucleic acid amplification;

introducing the prepared sample into the nucleic acid amplification area;

performing a nucleic acid amplification reaction in the nucleic acid amplification area to amplify the nucleic acid of interest; and detecting the amplified nucleic acid of interest.

25. The microfluidic device of claim 2, wherein the nucleic acid analysis area comprises an area for detecting an interaction between the nucleic acid of interest and a probe for the nucleic acid of interest.

26. The method of claim 24, wherein the nucleic acid amplification is selected from the group consisting of polymerase chain reaction (PCR), reverse-transcriptase (RT-) PCR, Rapid Amplification of cDNA Ends (RACE), rolling circle amplification, nucleic Acid Sequence Based Amplification (NASBA), Transcript Mediated Amplification (TMA), and Ligase Chain Reaction.

27. The method of claim 24, wherein the detecting step comprises detecting an interaction between the amplified nucleic acid of interest and a probe for the nucleic acid of interest.

28. The method of claim 24, wherein the detecting step comprises visualizing color intensity, fluorescence intensity, electrical signal intensity or chemiluminescence intensity.

29. The method of claim 24, wherein the detecting step comprises generating an intensity value corresponding to at least one molecule of interest in the sample.

30. The method of claim 29, wherein the intensity value is selected from the group consisting of color intensity value, fluorescence intensity value and chemiluminescence intensity value, current or voltage.

31. The method of claim 30, wherein generating the color intensity value comprises:

digitizing an image corresponding to the sample to generate a plurality of pixels;

providing a plurality of numerical values for respective ones of the plurality of pixels;

and producing numerical values to provide the color intensity value.

32. The method of claim 30, further comprising computing a threshold value and comparing the color intensity value to the threshold value to detect the molecule of interest.

33. The method of claim 24, further characterized by the step of:

introducing the amplified nucleic acid of interest into the nucleic acid analysis area.

34. A method for determining presence of or predisposition for a disease or disorder of interest in a subject comprising:

a) obtaining a sample from the subject, wherein the sample is suspected of containing a nucleic acid associated with the disease or disorder of interest; and b) detecting the nucleic acid associated with the disease or disorder of interest in the sample, wherein the detecting comprises the steps of:

providing the microfluidic device of claim 1, introducing the sample into the sample preparation area, preparing the sample for nucleic acid amplification, introducing the prepared sample into the nucleic acid amplification area, performing a nucleic acid amplification reaction in the nucleic acid amplification area to amplify the nucleic acid of interest, and detecting the amplified nucleic acid of interest;

wherein detecting the amplified nucleic acid of interest is associated with presence of or predisposition for the disease or disorder of interest.

35. The method of claim 34 wherein the detecting step comprises determining an amount (or level) of the amplified nucleic acid of interest and wherein the method further comprises comparing the amount (or level) with a preselected amount (or level) of the nucleic acid of interest.

36. The method of claim 35 wherein a difference between the amount (or level) with the preselected amount (or level) is indicative of presence or predisposition for the disease or disorder of interest.

* * * * *

```
SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Forward primer

<400> SEQUENCE: 1

acgttgctat ccaggctgtg ctat                                              24


<210> SEQ ID NO 2
<211> LENGTH: 24
<212> TYPE: DNA
<213> ORGANISM: Artificial Sequence
<220> FEATURE:
<223> OTHER INFORMATION: Reverse primer

<400> SEQUENCE: 2

actcctgctt gctgatccac atct                                              24
```